(12) United States Patent
Miki et al.

(10) Patent No.: US 8,758,960 B2
(45) Date of Patent: Jun. 24, 2014

(54) PHOTOREACTIVE COMPOSITION, OPTICAL MATERIAL, COMPOSITION FOR FORMING HOLOGRAPHIC RECORDING LAYER, HOLOGRAPHIC RECORDING MATERIAL, AND HOLOGRAPHIC RECORDING MEDIUM

(75) Inventors: Yasuaki Miki, Kanagawa (JP); Akiko Yabe, Kanagawa (JP); Jun Enda, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 193 days.

(21) Appl. No.: 12/997,364

(22) PCT Filed: Jun. 9, 2009

(86) PCT No.: PCT/JP2009/060555
§ 371 (c)(1),
(2), (4) Date: Dec. 10, 2010

(87) PCT Pub. No.: WO2009/151061
PCT Pub. Date: Dec. 17, 2009

(65) Prior Publication Data
US 2011/0092612 A1    Apr. 21, 2011

(30) Foreign Application Priority Data
Jun. 10, 2008  (JP) ................. 2008-152095

(51) Int. Cl.
*G03H 1/02*   (2006.01)
*G11B 7/244*  (2006.01)
*C07D 333/54* (2006.01)
*C07D 307/91* (2006.01)
*C07D 339/08* (2006.01)
*G11B 7/0065* (2006.01)
*C07D 333/76* (2006.01)

(52) U.S. Cl.
CPC ............. *G03H 1/02* (2013.01); *G03H 2260/12* (2013.01); *G11B 7/244* (2013.01); *G11B 7/0065* (2013.01); *G07D 339/08* (2013.01); *C07D 307/91* (2013.01); *C07D 333/54* (2013.01); *C07D 333/76* (2013.01)
USPC ........ 430/1; 430/2; 359/3; 522/154; 522/153; 549/17; 549/58; 549/461; 549/20; 549/49

(58) Field of Classification Search
None
See application file for complete search history.

(56) References Cited

U.S. PATENT DOCUMENTS

| | | | | |
|---|---|---|---|---|
| 4,917,977 | A * | 4/1990 | Smothers | 430/1 |
| 4,942,112 | A * | 7/1990 | Monroe et al. | 430/282.1 |
| 5,858,614 | A | 1/1999 | Sato et al. | |
| 5,874,187 | A | 2/1999 | Colvin et al. | |
| 6,165,648 | A | 12/2000 | Colvin et al. | |
| 6,304,312 | B1 * | 10/2001 | Tanabe et al. | 349/201 |
| 7,271,283 | B2 * | 9/2007 | Chisholm et al. | 560/152 |
| 7,514,127 | B2 * | 4/2009 | Lietzau et al. | 428/1.1 |
| 2005/0250016 | A1 * | 11/2005 | Takeyama | 430/1 |
| 2006/0057467 | A1 * | 3/2006 | Takizawa | 430/1 |
| 2008/0203356 | A1 * | 8/2008 | Kjellander et al. | 252/299.01 |

FOREIGN PATENT DOCUMENTS

| | | | |
|---|---|---|---|
| JP | 51 36222 | | 3/1976 |
| JP | 61-127712 | * | 6/1986 |
| JP | 02-029401 | * | 1/1990 |
| JP | 03-017107 | * | 1/1991 |
| JP | 05-098252 | * | 4/1993 |
| JP | 6 301322 | | 10/1994 |
| JP | 2002-105444 | * | 4/2002 |
| JP | 3330854 | | 9/2002 |
| JP | 2003-193055 | * | 7/2003 |
| JP | 2003 255543 | | 9/2003 |
| JP | 2004 277581 | | 10/2004 |
| JP | 2005 502918 | | 1/2005 |
| JP | 2005 43507 | | 2/2005 |
| JP | 2005 114848 | | 4/2005 |
| JP | 2005 114849 | | 4/2005 |
| JP | 2006 259508 | | 9/2006 |
| JP | 2006 259509 | | 9/2006 |
| JP | 2009 99253 | | 5/2009 |

OTHER PUBLICATIONS

Xue et al., "Study of optically active methacrylates containing 1,1'binaphthyl side groups . . . " Polym. Inter. vol. 51 pp. 1321-1325 (2002).*

Geczmiel et al., "Polymethacrylates with pendant oxadiazole units synthesis and application in organic LEDs", Macromol., vol. 30 pp. 6042-6046 (1997).*

Jiang et al., "Functional polymers. LV. Photochemical behavior of 2(2-hydroxylphenyl)2H-benzotriazole derivatives . . . ", Poly. Bull., vol. 20 pp. 161-168 (1988).*

Woltman et al., "Holographic diffraction gratings using polymer-dispersed ferroelectric liquid crystals", Opt. Lett., vol. 31(22) pp. 3273-3275 (Nov. 2006).*

International Search Report issued Aug. 11, 2009 in PCT/JP09/060555 filed Jun. 9, 2009.

Takeuchi, Junpei, "Holographic Display", Chapter 2, Published by Sangyo Tosho Publishing Co. Ltd., pp. 210-225, 240-243 and 276, (Dec. 7, 1990) (with partial English Translation).

Office Action issued Apr. 16, 2013 in Japanese Patent Application No. 2009-137734 (with English-language translation).

* cited by examiner

*Primary Examiner* — Martin Angebranndt
(74) *Attorney, Agent, or Firm* — Oblon, Spivak, McClelland, Maier & Neustadt, L.L.P.

(57) ABSTRACT

A novel polymerizable high-refractive index compound which is useful as an optical material, and a holographic recording medium using the same, which has high diffraction efficiency, high light transmittance and small rate of shrinkage, are provided. A composition for forming a holographic recording layer containing a reactive compound represented by the following formula 1, a holograph recording material, and a holographic recording medium provided with a recording layer containing the same, are disclosed.

[Formula 1]

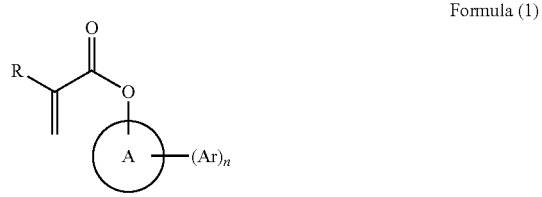

Formula (1)

(In the formula (1),

A is an optionally substituted ring;

Ar is an optionally substituted (hetero)aryl group formed by condensation of two or more rings;

R is hydrogen or a methyl group;

n is an integer of from 1 to 7; and when n is 2 or more, then plural Ars may be the same as or different from each other, provided that when A is an aromatic heterocyclic ring, and Ar is an optionally substituted (hetero)aryl group formed by condensation of two or more rings, then in the structure in which A and Ar are connected with each other, those partial structures that are in the structure of each of A and Ar, and are connected directly with each other, do not contain a heteroatom.)

10 Claims, 2 Drawing Sheets

PHOTOREACTIVE COMPOSITION, OPTICAL MATERIAL, COMPOSITION FOR FORMING HOLOGRAPHIC RECORDING LAYER, HOLOGRAPHIC RECORDING MATERIAL, AND HOLOGRAPHIC RECORDING MEDIUM

CROSS-REFERENCE TO RELATED APPLICATIONS

This application is a US National Stage Application of PCT/JP2009/060555, filed on Jun. 9, 2009, the text of which is incorporated by reference, and claims priority to Japanese Patent Application 2008-152095, filed on Jun. 10, 2008, the text of which is also incorporated by reference.

TECHNICAL FIELD

The present invention relates to a polymerizable novel reactive compound having high diffraction efficiency and high light transmittance and having small shrinkage following crosslinking.

Also, the invention relates to a photoreactive composition, a composition for forming a holographic recording layer and an optical material each containing the subject novel reactive compound and to a holographic recording material comprising the subject optical material and a holographic recording medium comprising the subject holographic recording material.

BACKGROUND ART

In recent years, resins having extensive optical characteristics as compared with conventional optical resins have been demanded in various optical applications. In particular, high-refractive index materials are being energetically studied in view of the extent of their application ranges including various resin lenses for optical data storage for next-generation DVD, camera for mobile phone, etc., liquids for immersion microscope lens, optical recording materials and so forth. Above all, in optical recording materials, especially holographic recording materials, the development of a material capable of attaining high refraction and low shrinkage is of an important issue.

The holography is a terminology meaning the whole of techniques in which a pattern made by an interference fringe formed from two lights (object light or information light and reference light) is recorded on a photosensitive material, and when light is applied thereto at the same angle as in the reference light, a recorded image or information of the object can be read. In view of the fact that by treating light as a plane, recording and reading can be achieved in a wide portion within a short period of time, in recent years, the holography is a technique which is very expected as a high-capacity, high-speed recording material.

Though the holography is classified into several types from the standpoint of a recording mode of interference fringe, it is considered that phase holography (volume holography) is high in performance in view of high diffraction efficiency and wavelength selectivity.

As a material capable of achieving such a technique, an organic material using a monomer polymerizable with light, which is named a so-called photopolymer, is exemplified.

The photopolymer as referred to herein expresses a material composed of at least a matrix resin, a polymerizable reactive compound and a photoinitiator.

At the time of recording a hologram, when a recording layer is present in an area where two lights intersect to become strong, the photoinitiator causes a chemical reaction to convert into an active material, and this acts on the polymerizable reactive compound, whereby the reactive compound is polymerized. On that occasion, when there is a difference in a refractive index among polymers formed from the matrix resin and the polymerizable reactive compound, an interference fringe becomes the difference in a refractive index and is immobilized in the recording layer. Also, on the occasion when the polymerizable reactive compound is polymerized, diffusion of the reactive compound occurs from the surroundings, and concentration distribution of the reactive compound or polymer of the reactive compound is generated in the inside of the photopolymer. Though when only reference light is irradiated, a record on the basis of the object light or information light is reproduced from the interference fringe, in the case of using the reference light having the same wavelength, by irradiating it on the recording layer at the time of reproduction, an unreacted polymerizable reactive compound should be similarly polymerized at the time of recording. However, as described previously, in view of the fact that concentration distribution of the reactive compound or polymer of the reactive compound is generated in the inside of the photopolymer, in an area where the two light intersect to become weak, namely an unrecorded area, since the concentration of the reactive compound relatively decreases, even when the reactive compound is polymerized in this area, the difference in a refractive index from the recorded area still remains. Accordingly, even when the same wavelength is irradiated at the time of reproduction, the record does not vanish (Non-Patent Document 1).

As a representative polymerizable monomer as such a reactive compound for photopolymer, N-vinylcarbazole and tribromophenyl acrylate are investigated (for example, Patent Documents 1 and 2). These compounds are sufficiently large in a refractive index of a polymer formed upon being polymerized as compared with a matrix resin, high in compatibility with the matrix resin in a stage before the polymerization and also high in compatibility with the matrix resin even after the polymerization, since unnecessary scattering is small; and therefore, even when repeatedly recorded, the diffraction efficiency is high, so that these compounds are suitable for holographic recording.

Also, it is reported in Patent Documents 3 to 5 that by using a polymerizable sulfur atom-containing compound or the like, a holographic recording material and a recording medium each having high diffraction efficiency and sensitivity are obtained. However, in general, there is a trade-off relation between diffraction efficiency and rate of shrinkage, and when a concentration of a polymerizable compound is increased for the purpose of enhancing the diffraction efficiency, polymerization shrinkage following recording becomes large. Even polymerizable compounds of the working examples exemplified in these patent documents are insufficient from the standpoints of diffraction efficiency, light transmittance and rate of shrinkage, and creation of further polymerizable compounds is being demanded.

PRIOR ART DOCUMENT

Patent Document

Patent Document 1: Japanese Patent No. 3330854
Patent Document 2: JP-T-2005-502918
Patent Document 3: JP-A-2005-114848
Patent Document 4: JP-A-2005-43507
Patent Document 5: JP-A-2005-114849

Non-Patent Document

Non-Patent Document 1: *Holographic Display*, Chapter 2, edited by TAKEUCHI, Junpei and published by Sangyo Tosho Publishing Co., Ltd.

SUMMARY OF THE INVENTION

Problem to be Solved by the Invention

The invention is one to solve the foregoing problem, and an object thereof is to provide an optical material, especially a novel polymerizable compound as a reactive compound to be used for holographic recording, and a holographic recording medium using the same, which has high diffraction efficiency, high light transmittance and small rate of shrinkage.

The diffraction efficiency of the holographic recording medium is proportional to a recording density per medium surface and is a numerical value which is converted from a difference in a refractive index. Here, the difference in a refractive index means a difference in a refractive index between a recorded area and an unrecorded area. The recorded area is an area polymerized by light, and the unrecorded area is a non-polymerized area.

In the holographic recording medium before recording, a matrix resin and a reactive compound are ensured in a uniform state to an extent that they have transmissivity at the recording wavelength. By irradiating light for recording on this holographic recording medium, the reactive compound is converted into a corresponding polymer due to an influence of an activated initiator.

In general, molecules come close to each other by polymerization, so that the density increases; and therefore, the reactive compound is polymerized due to recording and converted into a corresponding polymer, whereby the refractive index of the recorded area becomes relatively large relative to the refractive index of the unreacted area. Furthermore, on that occasion, movement of the reactive compound from a non-irradiated area to an irradiated area occurs due to a change in the density following polymerization.

Accordingly, in the case where the refractive index of the reactive compound is more than the refractive index of the matrix resin, in the irradiated area, the refractive index further increases in the unreacted area or as compared with that in the state before recording due to formation of the polymer and an increase of the concentration of the reactive compound. On the other hand, in the non-irradiated area, the refractive index further decreases as compared with that before recording due to a reduction of the concentration of the reactive compound. For that reason, the difference in a refractive index between the irradiated area and the non-irradiated area becomes larger. Inversely, in the case where the refractive index of the reactive compound is less than the refractive index of the matrix resin, in the irradiated area, though the refractive index increases in the unrecorded area or as compared with that in the state before recording due to formation of the polymer, an increase of the concentration of the reactive compound works as a decrease of the refractive index, and hence, a width of the increase is suppressed. Furthermore, in the non-irradiated area, since the refractive index increases as compared with that in the state before recording due to a reduction of the concentration of the reactive compound, the difference in a refractive index between the irradiated area and the non-irradiated area becomes small as compared with the case where the reactive compound is higher in a refractive index than the matrix resin.

In consequence, in order to make the difference in a refractive index between the irradiated area (recorded area) and the unirradiated area (unrecorded area) large, it is important that the refractive index of the matrix resin is smaller than the refractive index of the reactive compound; and that a difference therebetween is large. It may be considered that in view of the fact that the difference in a refractive index between the recorded area and the unrecorded area is larger, it is possible to make multiplicity large, and larger diffraction efficiency can be achieved.

In consequence, an object of the invention is to provide a polymerizable reactive compound which is large in a refractive index and small in shrinkage following crosslinking.

Means for Solving the Problem

In general, as means for making a refractive index of an organic material large, there are exemplified introduction of an aromatic ring and substitution of a carbon atom with a heavy atom such as sulfur or bromine. Then, the present inventors have found that by connecting a (hetero)aryl group having a condensed polycyclic structure directly with a ring structure having a (meth)acryloyl group to contrive to improve a refractive index and reduce a rate of shrinkage following crosslinking, especially using a compound of the following formula (1), a high-performance optical medium for holographic recording having high diffractive efficiency and low rate of shrinkage is obtained, leading to accomplishment of the invention.

That is, a gist of the invention is as follows.

(1) A composition for forming a holographic recording layer comprising a photoreactive compound represented by the following formula (1).

[Formula 1]

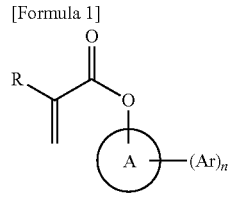

Formula (1)

(In the formula (1),
A is an optionally substituted ring;
Ar is an optionally substituted (hetero)aryl group formed by condensation of two or more rings;
R is hydrogen or a methyl group;
n is an integer of from 1 to 7; and
when n is 2 or more, then plural Ars may be the same as or different from each other,
provided that when A is an aromatic heterocyclic ring, and Ar is an optionally substituted (hetero)aryl group formed by condensation of two or more rings, then in the structure in which A and Ar are connected with each other, those partial structures that are in the structure of each of A and Ar, and are connected directly with each other, do not contain a heteroatom.)

(2) The composition for forming a holographic recording layer as set forth above in (1), wherein a refractive index of Ar estimated according to the Lorentz-Lorenz equation is 1.60 or more.

(3) The composition for forming a holographic recording layer as set forth above in (1) or (2), wherein Ar is an optionally substituted heteroaryl group formed by condensation of two or more rings.

(4) The composition for forming a holographic recording layer as set forth above in any one of (1) to (3), wherein a refractive index of A estimated according to the Lorentz-Lorenz equation is 1.43 or more.

(5) The composition for forming a holographic recording layer as set forth above in any one of (1) to (4), wherein A is an optionally substituted aromatic ring.

(6) The composition for forming a holographic recording layer as set forth above in any one of (1) to (5), wherein the composition for forming a holographic recording layer further comprises a matrix resin and a photoinitiator.

(7) The composition for forming a holographic recording layer as set forth above in (6), wherein the matrix resin is obtained by a reaction of an isocyanate and a polyol.

(8) A holographic recording material comprising the composition for forming a holographic recording layer as set forth above in any one of (1) to (7).

(9) A holographic recording medium comprising a layer containing the holographic recording material as set forth above in (8) as a recording layer.

(10) A compound represented by the following formula (2).

[Formula 2]

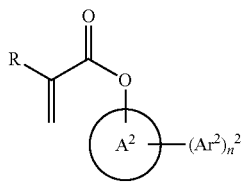

Formula (2)

(In the formula (2), $A^2$ is an optionally substituted ring selected from the group consisting of a benzene ring, a naphthalene ring and a dibenzothiophene ring;

$Ar^2$ is an optionally substituted, spiro carbon-free (hetero)aryl group formed by condensation of two or more rings;

R is hydrogen or a methyl group;

$n^2$ is an integer of from 1 to 7; and when $n^2$ is 2 or more, then plural $Ar^2$s may be the same as or different from each other, provided that when $A^2$ is a dibenzothiophene ring, and $Ar^2$ is an optionally substituted heteroaryl group formed by condensation of two or more rings, then in the structure in which $A^2$ and $Ar^2$ are connected with each other, the thiophene ring in the structure of $A^2$ and the partial structure including the heteroatom in the structure of $Ar^2$ are not connected directly with each other.)

(11) A compound represented by the following formula (2-1).

[Formula 3]

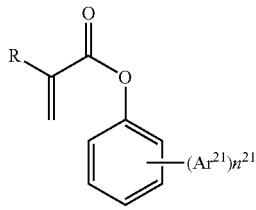

Formula (2-1)

(In the formula (2-1), $Ar^{21}$ is a heteroaryl group having a condensed polycyclic structure which is formed by bicondensation or tricondensation of at least one of a 6-membered ring and a 5-membered ring and has one or more heteroatoms in a skeleton of the condensed polycyclic structure, in which the heteroatom is at least one of oxygen and sulfur;

R is hydrogen or a methyl group;

$n^{21}$ is an integer of from 1 to 5; and when $n^{21}$ is 2 or more, then plural $Ar^{21}$s may be the same as or different from each other, provided that the benzene ring having $Ar^{21}$ in the formula (2-1) may further have a substituent in addition to $Ar^{21}$.)

(12) The compound as set forth above in (11), wherein in the formula (2-1), a heteroatom number which $Ar^{21}$ has in the skeleton of the condensed polycyclic structure is 1 or 2, $n^{21}$ is 1 or 2, and R is hydrogen or a methyl group.

(13) A photoreactive composition comprising the compound as set forth above in any one of (10) to (12).

(14) The photoreactive composition as set forth above in (13), wherein the photoreactive composition further comprising a matrix resin and a photoinitiator.

(15) The photoreactive composition as set forth above in (14), wherein the matrix resin is obtained by a reaction of an isocyanate and a polyol.

(16) An optical material comprising the photoreactive composition as set forth above in any one of (13) to (15).

(17) A holographic recording material comprising the optical material as set forth above in (16).

(18) A holographic recording medium comprising a layer containing the holographic recording material as set forth above in (17) as a recording layer.

Advantage of the Invention

According to the invention, a novel polymerizable high-refractive index compound which is useful as an optical material is provided. The subject compound is especially useful as a reactive compound to be used for holographic recording, and use of this makes it possible to realize a high-performance holographic recording medium which is high in diffraction efficiency, high in a light transmittance and small in a rate of shrinkage.

MODE FOR CARRYING OUT THE INVENTION

Figure 1:
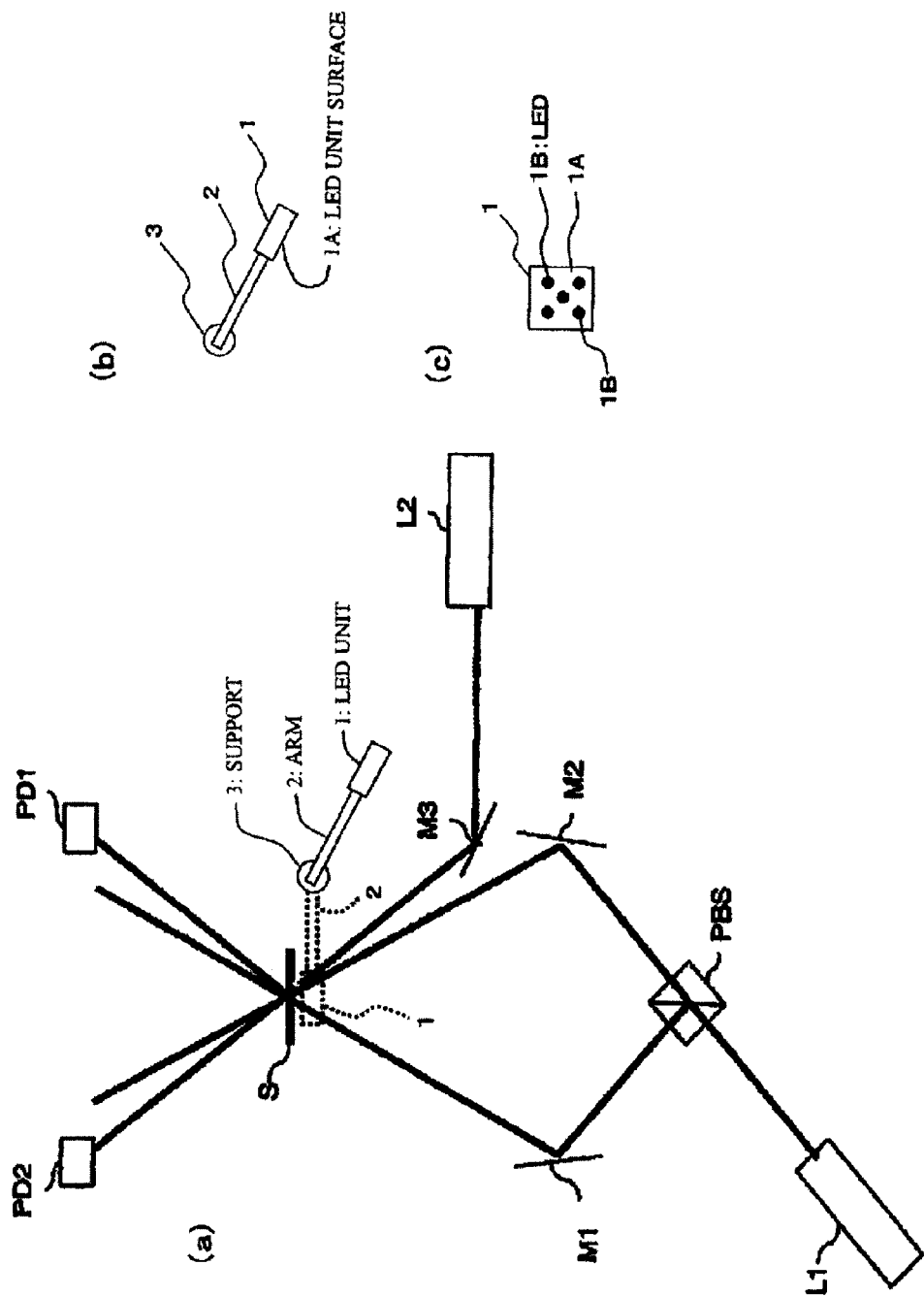
FIG. 1 is a schematic view showing an outline of a configuration of an apparatus used for holographic recording in Example 1, in which (a) is a view showing the whole of the apparatus, (b) is a view showing a surface of an LED unit, and (c) is a view showing an arrangement of LED.

While embodiments of the invention are hereunder specifically described, it should not be construed that the invention is limited the following embodiments, and the invention can be carried out through various modifications within the range of a gist thereof.

I. Composition for Forming Holographic Recording Layer

I-1. Photoreactive Compound

The composition for forming a holographic recording layer comprises a photoreactive compound represented by the following formula (1).

[Formula 4]

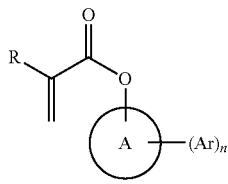

Formula (1)

(In the formula (1),

A is an optionally substituted ring;

Ar is an optionally substituted (hetero)aryl group formed by condensation of two or more rings;

R is hydrogen or a methyl group;

n is an integer of from 1 to 7; and when n is 2 or more, then plural Ars may be the same as or different from each other, provided that when A is an aromatic heterocyclic ring, and Ar is an optionally substituted (hetero)aryl group formed by condensation of two or more rings, then in the structure in which A and each Ar are connected directly with each other, those partial structures in the structure of A and each Ar which are connected directly with each other do not contain a heteroatom.)

[Description of Words and Phrases]

In the invention, the "(hetero)aryl" means both "aryl" and "heteroaryl".

Also, in the invention, the "optionally substituted" means that one or more substituents may be included.

I-1-1. A

A is an optionally substituted ring.

A structure in which A occupies a small proportion in the whole of the molecule and is capable of bearing a plurality of high-refractive index substituent Ars is preferable.

It is preferable that A has a high refractive index. The refractive index as A can be estimated according to the Lorentz-Lorenz equation. Specifically, a method of estimating the refractive index is described in IDE, Fumio, *Optoelectronics and Polymer Materials*, Chapter 2, "2.2 Refractive Index" or the like. According to this, the refractive index can be estimated from a molecular refraction (may also be called "molar refraction") which is expressed as a total sum of atomic refractions and a specific gravity.

The refractive index as A is 1.43 or more, preferably 1.47 or more, more preferably 1.48 or more, and especially preferably 1.50 or more. When the refractive index is excessively low, the refractive index as the whole of the molecule becomes low. Also, the refractive index as A is usually not more than 1.95, and preferably not more than 1.90. This is because when the refractive index is excessively high, an optical path is deviated due to an effect of refraction, and scattering becomes large, so that a defective such as crosstalk of an inputted value or the like is generated.

Examples of the ring of A include 3- to 8-membered, preferably 5- to 6-membered aromatic hydrocarbon rings, aromatic heterocyclic rings, aliphatic hydrocarbon rings and aliphatic heterocyclic rings. The ring of A may be either a monocyclic structure or a condensed ring structure. A ring number for constituting the ring of A is from 1 to 4, preferably from 1 to 3, and more preferably from 1 to 2. Though the ring of A is not always required to have aromaticity, it is preferable that an unsaturated bond is contained for the purpose of maintaining a high refractive index while keeping the proportion of A occupying in the whole of the molecule small; and it is more preferable that the ring of A is an aromatic hydrocarbon ring or an aromatic heterocyclic ring. Also, in order to ensure light transmissivity at the time of recording/reproducing a hologram, it is preferable that coloration is small, and from this standpoint, the ring of A is more preferably an aromatic hydrocarbon ring.

<Aromatic Hydrocarbon Ring>

Examples of the aromatic hydrocarbon ring include aromatic hydrocarbon rings having from 6 to 14 carbon atoms, and preferably from 6 to 12 carbon atoms, such as a benzene ring, an indene ring, a naphthalene ring, an azulene ring, a fluorene ring, an acenaphthylene group, an anthracene ring, a phenanthrene ring, a pyrene ring, etc. From the standpoints of avoiding coloration and ensuring solubility, those having from 6 to 10 carbon atoms including a benzene ring and a naphthalene ring are especially preferable.

<Aromatic Heterocyclic Ring>

The heteroatom is not particularly limited, and each atom of S, O, N, P or the like can be used. From the standpoint of ensuring compatibility, each atom of S, O or N is preferable, and each atom of S or O is especially preferable. Also, from the standpoints of avoiding coloration and ensuring solubility, the heteroatom number is preferably from 1 to 2 in the molecule.

Specific examples thereof include aromatic hydrocarbon rings having from 8 to 18 carbon atoms, and preferably from 8 to 12 carbon atoms, such as a benzofuran ring, a benzothiophene ring, a dibenzofuran ring, a dibenzothiophene ring, a thianthrene ring, a dibenzothioxane ring, a benzothiophene ring, etc. Of these, a dibenzothiophene ring and a thianthrene ring are preferable from the standpoints of compatibility and coloration.

<Aliphatic Hydrocarbon Ring>

Examples of the aliphatic hydrocarbon ring include cycloalkanes having from 5 to 14 carbon atoms, and preferably from 6 to 14 carbon atoms, such as a cyclopentane ring, a cyclohexane ring, a norbornene ring, a decalin ring, a perhydroanthracene ring, a perhydropyrene ring, etc.; cycloalkenes having from 5 to 14 carbon atoms, and preferably from 6 to 14 carbon atoms, such as a cyclopentene ring, a cyclohexene ring, a norbornene ring, a dodecahydroanthracene ring, etc.; cycloalkadienes having from 5 to 10 carbon atoms, and preferably from 7 to 10 carbon atoms, such as a cyclopentadiene ring, a norbornadiene ring, a cyclooctadiene ring, a dicyclopentadiene ring, etc.; and so forth.

Of these, a decalin ring, a perhydroanthracene ring, a dicyclopentadiene ring and so forth are preferable from the standpoint of compatibility.

<Aliphatic Heterocyclic Ring>

The heteroatom is not particularly limited, and each atom of S, O, N, P or the like can be used. From the standpoint of ensuring the refractive index, each atom of S, O or N is preferable, and each atom of S or O is especially preferable. Also, from the standpoints of avoiding coloration and ensuring solubility, the heteroatom number is preferably from 1 to 2 in the molecule. Specific examples thereof include aliphatic heterocyclic rings having from 3 to 5 carbon atoms, and preferably from 3 to 4 carbon atoms, such as a dioxolane ring, a dithiolane ring, a tetrahydrofuran ring, a tetrahydrothiophene ring, a dithiane ring, a dihydropyrane ring, etc. Of these, a dithiolane ring and a dithiane ring are preferable from the standpoint of refractive index.

<Substituent which A May have>

A may further have a substituent in addition to Ar. For example, for the purpose of enhancing the solubility, an alkyl group, an alkoxy group, an alkoxyalkyl group, an alkoxycarbonyl group, an alkoxyalkoxy group or an alkanoyloxy group may be substituted thereon; and for the purpose of increasing the refractive index, an aryl group, an alkylthioalkyl group, an aryloxy group or an arylalkoxyl group may be substituted thereon. However, for the purpose of achieving economic synthesis, it is preferable that A is unsubstituted.

Here, the alkyl group is preferably a chain alkyl group having from 1 to 4 carbon atoms, and specific examples thereof include a methyl group, an ethyl group, a propyl group, an isopropyl group, a butyl group, an isobutyl group, a sec-butyl group, etc.

The alkoxy group is preferably an alkoxy group having from 1 to 4 carbon atoms, and specific examples thereof include a methoxy group, an ethoxy group, etc.

The alkoxyalkyl group is preferably an alkoxyalkyl group having from 2 to 6 carbon atoms, and specific examples thereof include a methoxymethyl group, an ethoxymethyl group, a propoxymethyl group, a butoxymethyl group, a methoxyethyl group, an ethoxyethyl group, a propoxyethyl group, a butoxyethyl group, etc.

The alkoxycarbonyl group is preferably an alkoxycarbonyl group having from 2 to 5 carbon atoms, and specific examples thereof include a methoxycarbonyl group, an ethoxycarbonyl group, a propoxycarbonyl group, a butoxycarbonyl group, etc.

The alkoxyalkoxy group is preferably an alkoxyalkoxy group having from 3 to 6 carbon atoms, and specific examples thereof include a methoxyethoxy group, an ethoxyethoxy group, a propoxyethoxy group, a butoxyethoxy group, etc.

The alkanoyloxy group is preferably an alkanoyloxy group having from 2 to 5 carbon atoms, and specific examples thereof include an acetoxy group, a propionoxy group, a butyloxy group, a valeroxy group, etc.

The aryl group is preferably a monocyclic or condensed-ring aryl group having from 6 to 14 carbon atoms, and specific examples thereof include a phenyl group, a naphthyl group, an anthranyl group, etc.

The alkylthioalkyl group is preferably is preferably an alkylthioalkyl group having from 2 to 4 carbon atoms, and specific examples thereof include a methylthiomethyl group, a methylthioethyl group, an ethylthiomethyl group, an ethylthioethyl group, etc.

The aryloxy group is preferably a monocyclic or condensed-ring aryloxy group having from 6 to 14 carbon atoms, and specific examples thereof include a phenoxy group, etc.

The arylalkoxy group is preferably an arylalkoxy group having from 7 to 5 carbon atoms, and specific examples thereof include a benzyloxy group, etc.

I-1-2. Ar

Ar is an optionally substituted (hetero)aryl group formed by condensation of two or more rings. Ar is a group working as the linchpin for the purpose of realizing a high refractive index of the molecule represented by the formula (1), and a structure in which the refractive index as Ar is high is preferable. Here, similar to the foregoing A, the refractive index as Ar can be estimated according to the Lorentz-Lorenz equation.

The refractive index as Ar is usually 1.60 or more, preferably 1.65 or more, more preferably 1.70 or more, and especially preferably 1.75 or more. Also, the refractive index as Ar is usually not more than 1.95, and preferably not more than 1.90. This is because when the refractive index is excessively high, an optical path is deviated due to an effect of refraction, and scattering becomes large, so that a defective such as crosstalk of an inputted value or the like is generated.

Furthermore, from the viewpoint of reduction of the rate of shrinkage following crosslinking at the time of light irradiation, it is preferable that Ar has a high molecular weight to some extent, and the molecular weight of the Ar moiety is usually 50 or more, and preferably 70 or more. Also, from the viewpoint of ensuring the monomer mobility at the time of optical recording, the molecular weight of the Ar moiety is usually not more than 300, and preferably not more than 250.

As the (hetero)aryl group of Ar, there is exemplified a group formed by condensation of two or more of a 3- to 8-membered, preferably 5- to 6-membered aromatic hydrocarbon ring and/or a heterocyclic ring having one or more unsaturated bonds. A ring number for constituting the (hetero)acryl group of Ar is usually from 2 to 5, and preferably from 2 to 3.

<Aryl Group Formed by Condensation of Two or More Rings>

Specific examples of the aryl group formed by condensation of two or more rings include groups having from 6 to 14 carbon atoms, and preferably from 6 to 12 carbon atoms, such as an indene ring, a naphthalene ring, an azulene ring, a fluorene ring, an acenaphthylene ring, an anthracene ring, a phenanthrene ring, a pyrene ring, etc. Of these, from the standpoint of refractive index, it is preferable that the ring number is as large as possible. However, in view of the fact that a structure in which conjugation extends long is easy to connect with coloration, a twisted structure is more preferable.

<Heteroaryl Group Formed by Condensation of Two or More Rings>

The heteroaryl group formed by condensation of two or more rings is a group which includes at least a heterocyclic structure having one or more heteroatoms and one or more unsaturated bonds in a ring and in which one or more aromatic hydrocarbon rings and/or heterocyclic rings having one or more unsaturated bonds are condensed. Delocalization of a π-electron is not always required to be high, and it may be considered that the facts that an unsaturated bond number is large and that the heteroatom is contained greatly contribute to a high refractive index.

The heteroatom contained in the ring is not particularly limited, and each atom of S, O, N, P or the like can be used. From the standpoint of ensuring the refractive index, each atom of S, O or N is preferable, and each atom of S or O is especially preferable. Also, from the standpoints of avoiding coloration and ensuring solubility, the heteroatom number is preferably from 1 to 2 in the molecule.

In view of the fact that there may be the case where if the structural regularity of Ar is high, coloration or lowering of dissolution is caused due to stacking, a heteroaryl group formed by condensation of two or more rings is especially more preferable.

Also, it is preferable that Ar does not contain spiro carbon from a reason that the refractive index is decreased.

<Specific Examples of Ar>

Specific examples of Ar are given below, but it should not be construed that the invention is limited to thereto so far as the gist thereof is not deviated.

[Formula 5]

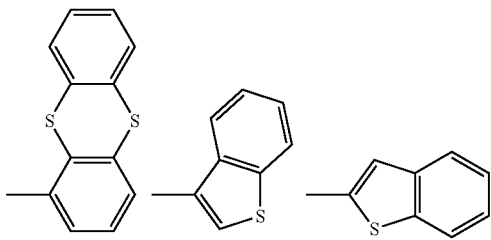

[Formula 6]

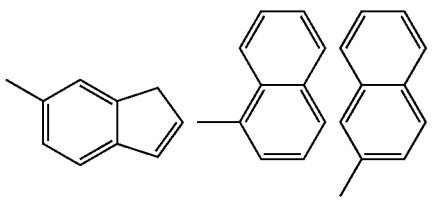

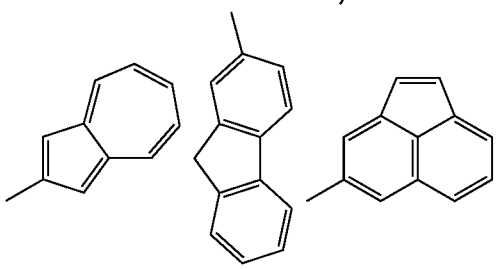

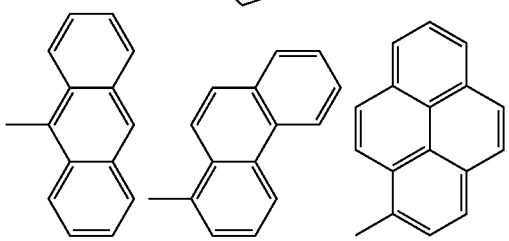

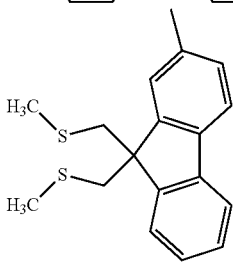

Besides, there are exemplified benzothioxane, benzothioxine, dibenzothioxine, benzodioxane, benzodioxine, benzodioxine and so forth.

Of these, from the standpoint of refractive index, thianthrene, dibenzothiophene and benzothiophene are preferable, and thianthrene and dibenzothiophene are more preferable.

<Substituent which Ar May have>

Ar may further have a substituent. The substituent which Ar may have is not particularly limited so far as the compatibility is not lowered, or the refractive index is not decreased. Specific examples thereof include an alkylthio group having from 1 to 3 carbon atoms, such as a methylthio group, etc.; and an alkylthioalkyl group having from 2 to 6 carbon atoms, such as a methylthiomethyl group, etc.

I-1-3. Bonding Position Between A and Ar

Incidentally, as to a preferred substitution position of Ar relative to A, when it is 1, any substitution position is applicable; and when it is 2 or more, it is preferable that the substitution positions are not adjacent to each other from a reason that a synthesis yield is high.

However, when A is a heteroaryl ring, and Ar is an optionally substituted heteroaryl group formed by condensation of two or more rings, then in the structure in which A and each Ar are connected with each other, those partial structures in the structure of A and each Ar which are connected directly with each other do not contain a heteroatom. In other words, in the structure in which A and Ar are connected with each other, those partial structures containing a heteroatom in the structures of A and Ar are not connected directly with each other. The structure in which those partial structures containing a heteroatom in the structures of A and Ar are connected directly with each other is not preferable because it is easy to have absorption in a visible light region, and a possibility that light transmission at the time of recording/reproduction is disturbed by this coloration is high.

I-1-4. n n is an integer of from 1 to 7, and when n is 2 or more, then plural Ars may be the same as or different from each other. In order to obtain good solubility in a solvent or a matrix, n is preferably from 1 to 5, more preferably from 1 to 3, and especially preferably 1 or 2.

I-1-5. Preferred Embodiments

The photoreactive compound represented by the general formula (1) is more preferably represented by the following formula (1-1).

[Formula 7]

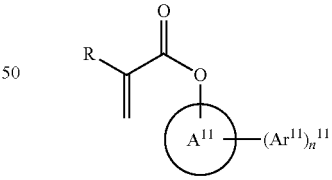

Formula (1-1)

(In the formula (1-1), $A^{11}$ is an optionally substituted ring selected from the group consisting of a benzene ring, a naphthalene ring and a dibenzothiophene group;

$Ar^{11}$ is an optionally substituted, spiro carbon-free (hetero) aryl group formed by condensation of two or more rings;

R is hydrogen or a methyl group;

$n^{11}$ is an integer of from 1 to 7; and when $n^{11}$ is 2 or more, then plural $Ar^{11}$s may be the same as or different from each other, provided that when $A^{11}$ is a dibenzothiophene ring, and $Ar^{11}$ is an optionally substituted heteroaryl group formed by condensation of two or more rings, then in the structure in which $A^{11}$ and each $Ar^{11}$ are connected with each other, those partial structures including the thiophene ring in the structure of $A^{11}$ and the heteroatom in the structure of $Ar^{11}$ are not connected directly with each other.)

<$A^{11}$>

In the formula (1-1), $A^{11}$ is an optionally substituted ring selected from the group consisting of a benzene ring, a naphthalene ring and a dibenzothiophene group, and preferably a benzene ring or a naphthalene ring. $A^{11}$ may further have a substituent in addition to $Ar^{11}$. The substituent which $A^{11}$ may have is not particularly limited so far as the compatibility is not lowered, or the refractive index is not decreased, and examples thereof include those described previously as the specific examples of the substituent which A may have in addition to Ar, and so forth.

<$Ar^{11}$>

In the formula (1-1), $Ar^{11}$ is an optionally substituted, spiro carbon-free (hetero)aryl group formed by condensation of two or more rings. As specific examples of Ar, among the groups described previously as the specific examples of Ar, those which do not contain spiro carbon are exemplified. Suitable examples are also the same as those in Ar.

<$n^{11}$>

In the formula (1-1), $n^{11}$ is an integer of from 1 to 7, and when $n^{11}$ is 2 or more, then plural Ars may be the same as or different from each other. In order to obtain good solubility in a solvent or a matrix, $n^{11}$ is preferably from 1 to 5, more preferably from 1 to 3, and especially preferably 1 or 2.

A more preferable compound of the photoreactive compound represented by the formula (1-1) is further represented by the following formula (1-2).

[Formula 8]

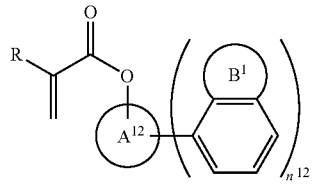

Formula (1-2)

(In the formula (1-2), $A^{12}$ is an optionally substituted ring selected from the group consisting of a benzene ring, a naphthalene ring and a dibenzothiophene group;

the ring $B^1$ is a heteroaryl group which is a 6-membered and/or 5-membered monocycle or two-condensed ring and which has one or more heteroatoms in a skeleton thereof, with the heteroatom being an oxygen atom and/or a sulfur atom;

$n^{12}$ is an integer of from 1 to 7;

when $n^{12}$ is 2 or more, then plural Bs may be the same as or different from each other; and R is hydrogen or a methyl group.)

<$A^{12}$>

In the formula (1-2), $A^{12}$ is an optionally substituted ring selected from the group consisting of a benzene ring, a naphthalene ring and a dibenzothiophene group, and preferably a benzene ring or a naphthalene ring. $A^{12}$ may further have a substituent in addition to the heteroaryl group containing the ring $B^1$. The substituent which $A^{12}$ may have is not particularly limited so far as the compatibility is not lowered, or the refractive index is not decreased, and examples thereof include those described previously as the specific examples of the substituent which A may have in addition to Ar, and so forth.

<$B^1$>

In the formula (1-2), $B^1$ is a heteroaryl group which is a 6-membered and/or 5-membered monocycle or two-condensed ring and which has one or more heteroatoms in a skeleton thereof, with the heteroatom being an oxygen atom and/or a sulfur atom. Specific examples thereof include corresponding portions of $B^1$ described previously as the specific examples of Ar are exemplified. Suitable examples thereof are also the same as those in Ar.

<$n^{12}$>

In the formula (1-2), $n^{12}$ is an integer of from 1 to 7, and when $n^{12}$ is 2 or more, plural $B^1$s may be the same as or different from each other. In order to obtain good solubility in a solvent or a matrix, $n^{12}$ is preferably from 1 to 5, more preferably from 1 to 3, and especially preferably 1 or 2.

I-1-6. Molecular Weight and Water Solubility

From the standpoint of reduction of the rate of shrinkage following crosslinking at the time of light irradiation or recording sensitivity, a molecular weight of the above-described photoreactive compound represented by the formula (1), preferably the formula (1-1), and more preferably the formula (1-2) is usually not more than 1,500, preferably not more than 1,000, further preferably not more than 850, and especially preferably not more than 750. Above all, the molecular weight is not more than 600 and usually 300 or more, preferably 350 or more and especially preferably 400 or more.

Also, from the reason of enhancing the storage stability of a recording medium or the like, in general, it is preferable that the photoreactive compound represented by the formula (1) is insoluble in water. Here, the term "insoluble in water" means that a solubility in water under a condition at 25° C. and 1 atm. is usually not more than 0.1% by weight, and preferably not more than 0.01% by weight.

I-1-7. Refractive Index

A refractive index or apparent refractive index at an irradiation light wavelength (recording wavelength or the like) of the photoreactive compound represented by the formula (1), preferably the formula (1-1), and more preferably the formula (1-2) is usually in the range of 1.62 or more and not more than 1.78, and preferably not more than 1.77. In the case of using the photoreactive compound represented by the formula (1), preferably the formula (1-1), and more preferably the formula (1-2) as a holographic recording material, when the refractive index is excessively small, the diffraction efficiency is not large, and the multiplicity is not sufficient. Also, when the refractive index is excessively large, a difference in the refractive index from the matrix resin becomes excessively large, so that scattering becomes large; and thus, the transmittance is lowered, thereby requiring larger energy during recording or reproduction.

Incidentally, when the refractive index is evaluated at a short wavelength, it exhibits a large value; however, a sample exhibiting a relatively large refractive index at a short wavelength also exhibits a relatively large refractive index even at a long wavelength, so that its relation is not reversed. In consequence, it is possible to evaluate a refractive index or apparent refractive index at a wavelength other than the recording wavelength, thereby predicting a refractive index at the recording wavelength.

Here, a value at the recording wavelength of 589 nm was made a basis.

In the case where the subject compound is a solid, the refractive index cannot be measured as it is. Thereafter, the apparent refractive index as referred to herein means a value obtained by, as described in Synthesis Example 1 as described later, dissolving the compound in an appropriate solvent to form a solution, measuring a refractive index of this solution and determining a refractive index in the case where the compound is 100% by means of extrapolation.

I-1-8. Illustrative Compounds

Specific examples of the compounds represented by the foregoing formula (1), formula (1-1) and formula (1-2) are given below, but it should not be construed that the invention is limited to thereto so far as the gist thereof is not deviated.

[Formula 9]

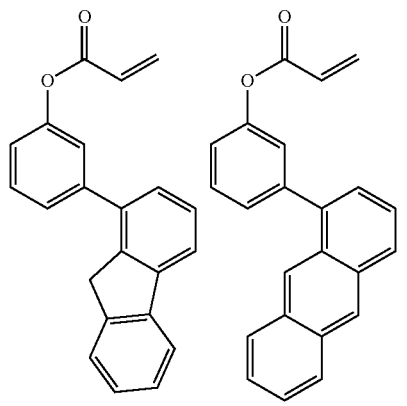

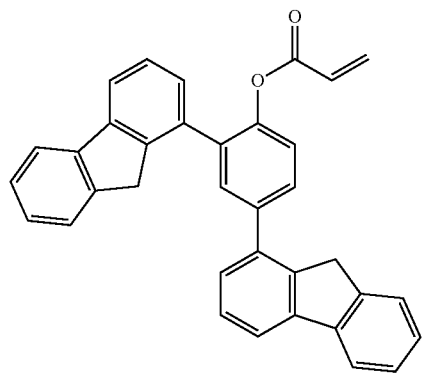

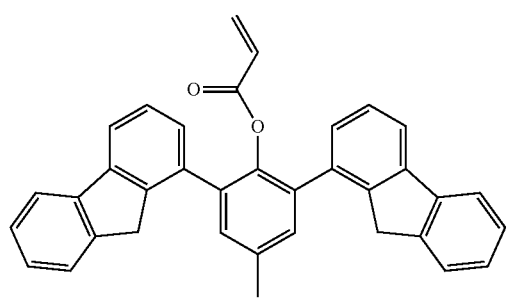

-continued

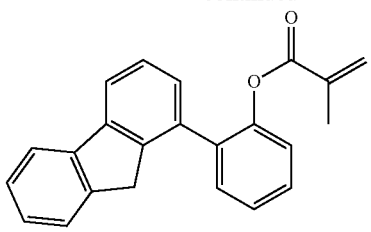

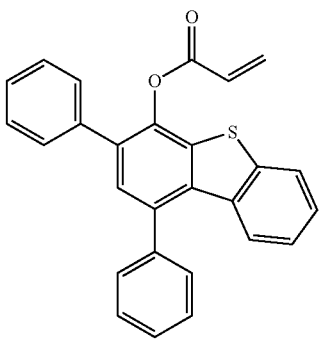

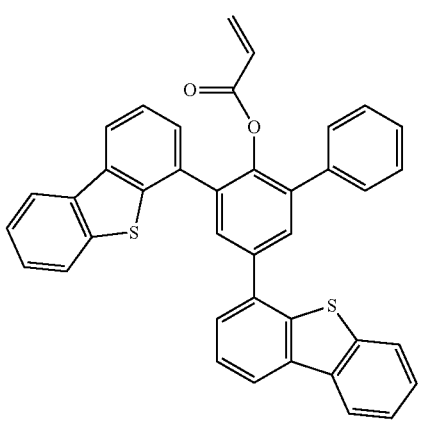

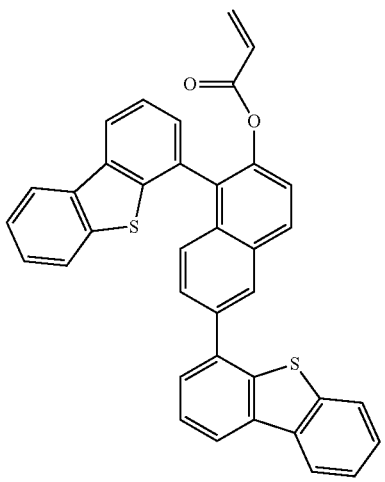

[Formula 10]
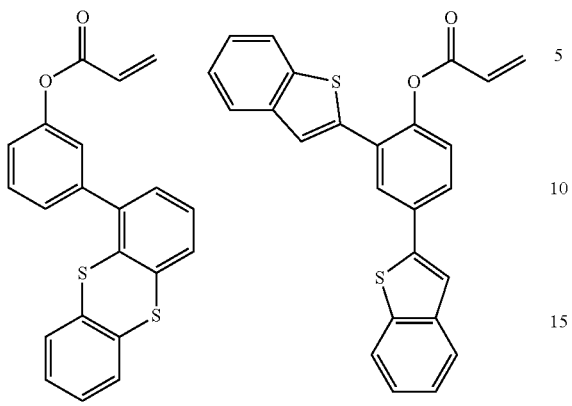
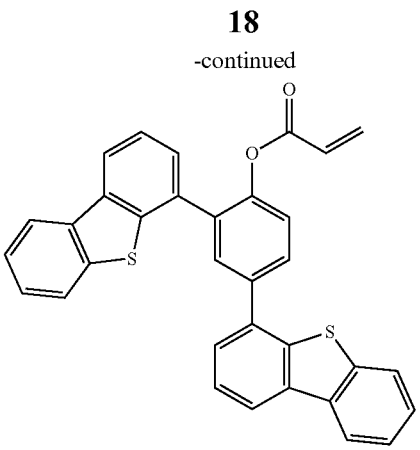
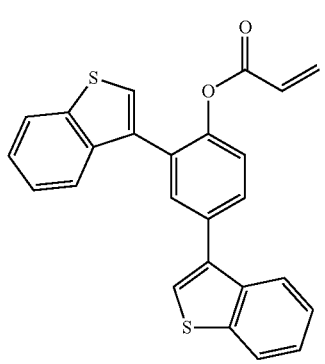
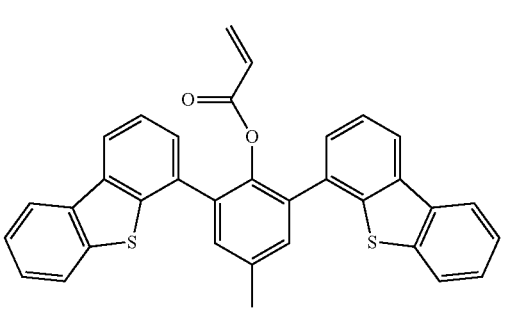
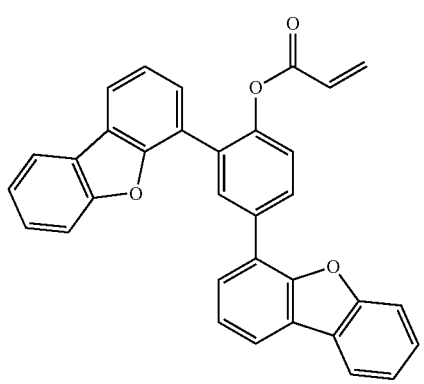
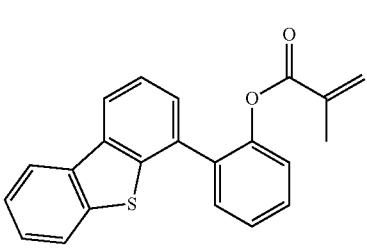
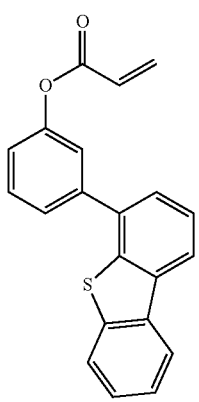
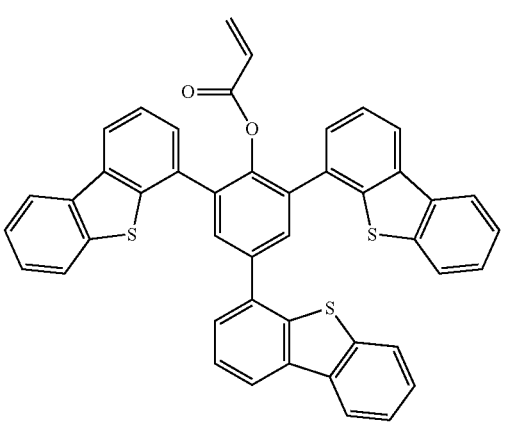

19
-continued
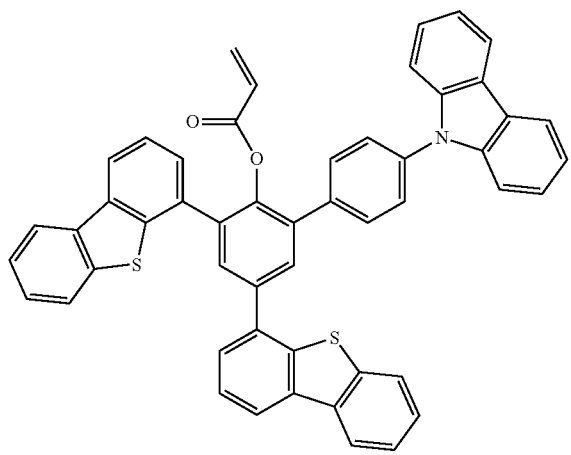
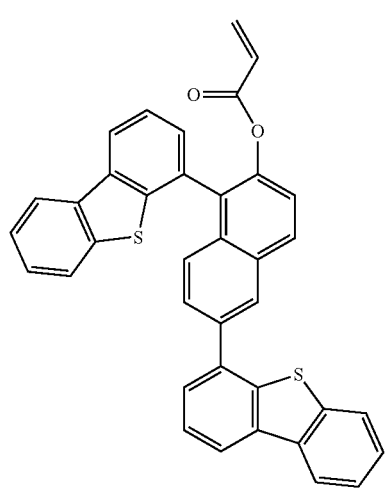
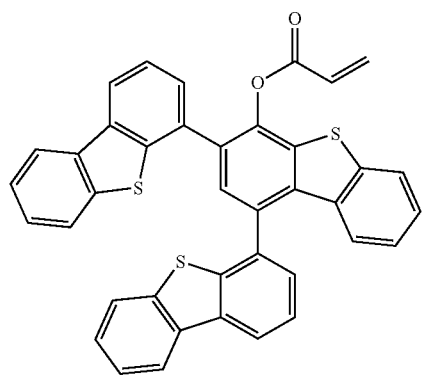
20
-continued
[Formula 11]
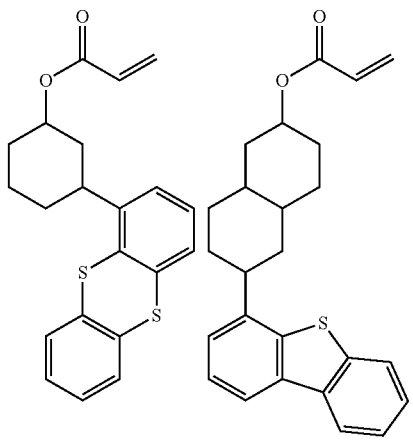
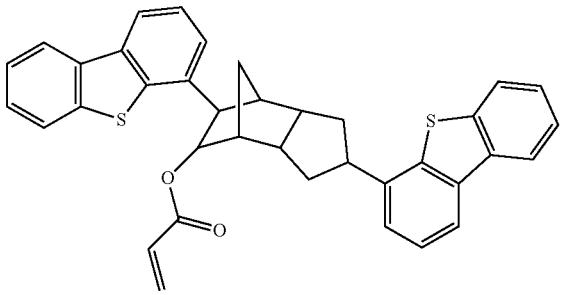
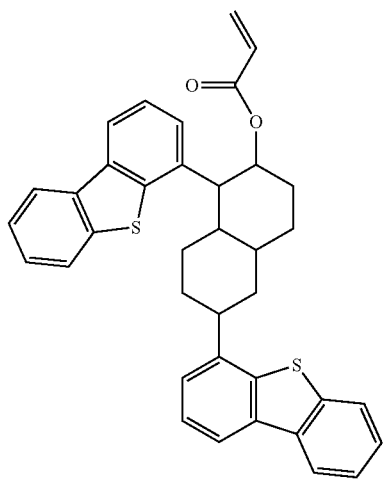

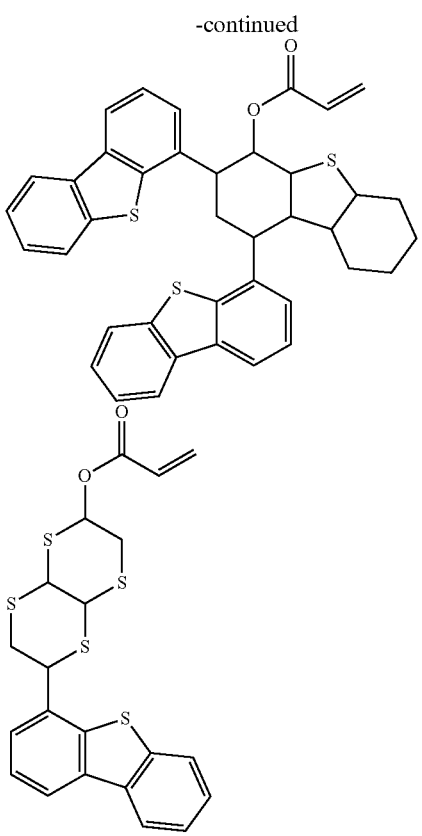

2-(1-thianthrenyl)-1-phenyl acrylate, 2-(2-benzothiophenyl)-1-phenyl acrylate, 2-(3-benzothiophenyl)-1-phenyl acrylate, 2-(4-dibenzofuranyl)-1-phenyl acrylate, 2-(4-dibenzothiophenyl)-1-phenyl acrylate, 3-(1-thianthenyl)-1-phenyl acrylate, 3-(2-benzothiophenyl)-1-phenyl acrylate, 3-(3-benzothiophenyl)-1-phenyl acrylate, 3-(4-dibenzofuranyl)-1-phenyl acrylate, 3-(4-dibenzothiophenyl)-1-phenyl acrylate, 4-(1-thiantherenyl)-1-phenyl acrylate, 4-(2-benzothiophenyl)-1-phenyl acrylate, 4-(3-benzothiophenyl)-1-phenyl acrylate, 4-(4-dibenzofuranyl)-1-phenyl acrylate, 4-(4-dibenzothiophenyl)-1-phenyl acrylate, 2,4-bis(1-thianthrenyl)-1-phenyl acrylate, 2,4-bis(2-benzothiophenyl)-1-phenyl acrylate, 2,4-bis(3-benzothiophenyl)-1-phenyl acrylate, 2,4-bis(4-dibenzofuranyl)-1-phenyl acrylate, 2,4-bis(4-dibenzothiophenyl)-1-phenyl acrylate, 4-methyl-2,6-bis(1-thiathrenyl)-1-phenyl acrylate, 4-methyl-2,6-bis(2-benzothiophenyl)-1-phenyl acrylate, 4-methyl-2,6-bis(3-benzothiophenyl)-1-phenyl acrylate, 4-methyl-2,6-bis(4-dibenzofuranyl)-1-phenyl acrylate, 4-methyl-2,6-bis(4-dibenzothiophenyl)-1-phenyl acrylate, 2-(1-thianthrenyl)-1-phenyl methacrylate, 2-(2-benzothiophenyl)-1-phenyl methacrylate, 2-(3-benzothiophenyl)-1-phenyl methacrylate, 2-(4-dibenzofuranyl)-1-phenyl methacrylate, 2-(4-dibenzothiophenyl)-1-phenyl methacrylate, 3-(1-thianthrenyl)-1-phenyl methacrylate, 3-(2-benzothiophenyl)-1-phenyl methacrylate, 3-(3-benzothiophenyl)-1-phenyl methacrylate, 3-(4-dibenzofuranyl)-1-phenyl methacrylate, 3-(4-dibenzothiophenyl)-1-phenyl methacrylate, 4-(1-thianthrenyl)-1-phenyl methacrylate, 4-(2-benzothiophenyl)-1-phenyl methacrylate, 4-(3-benzothiophenyl)-1-phenyl methacrylate, 4-(4-dibenzofuranyl)-1-phenyl methacrylate, 4-(4-dibenzothiophenyl)-1-phenyl methacrylate, 2,4-bis(1-thianthrenyl)-1-phenyl methacrylate, 2,4-bis(2-benzothiophenyl)-1-phenyl methacrylate, 2,4-bis(3-benzothiophenyl)-1-phenyl methacrylate, 2,4-bis(4-dibenzofuranyl)-1-phenyl methacrylate, 2,4-bis(4-dibenzothiophenyl)-1-phenyl methacrylate, 4-methyl-2,6-bis(1-thiathrenyl)-1-phenyl methacrylate, 4-methyl-2,6-bis(2-benzothiophenyl)-1-phenyl methacrylate, 4-methyl-2,6-bis(3-benzothiophenyl)-1-phenyl methacrylate, 4-methyl-2,6-bis(4-dibenzofuranyl)-1-phenyl methacrylate, 4-methyl-2,6-bis(4-dibenzothiophenyl)-1-phenyl methacrylate, and so forth.

I-1-9. Synthesis Method

The compound represented by the formula (1), preferably the formula (1-1), and more preferably the formula (1-2) can be synthesized by a combination of various known methods.

That is, the compound is obtained by subjecting a compound (a) having a hydroxyl group at the (meth)acryloyl group-introducing position and X at each of the Ar group-introducing positions having an n number on the ring A and a borated Ar compound (b) to an appropriate coupling reaction at a position to be introduced, thereby synthesizing a precursor (c). In the following scheme, X is a halogen atom, and though it is preferably bromine or iodine, it does not matter that X is chlorine.

Also, all of A, Ar and n are synonymous with those in the general formula (1).

[Formula 12]

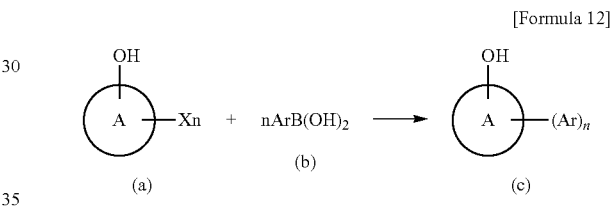

(1) The borated Ar compound (b) can be synthesized by lithiating the Ar compound with butyllithium and trapping the lithiated Ar compound with a boric acid ester, followed by hydrolysis.

(2) The precursor (c) can be synthesized by dissolving the obtained borated Ar compound (b) and the compound (a) having a hydroxyl group at the (meth)acryloyl group-introducing position and X at each of the Ar group-introducing positions on the ring A in an appropriate organic solvent and subjecting the solution to a coupling reaction with appropriate base and metal catalyst.

Incidentally, the foregoing compound (a) can be obtained by purchasing a commercially available product or by halogenating a hydroxyl group-containing compound. The halogenation is achieved by, for example, chlorine, bromine, iodine, N-bromosuccinic acid imide or iodine chloride. Further, the hydroxyl group-containing compound can be obtained from a corresponding halide, sulfate, nitrate or borate.

As the organic solvent, dimethoxyethane, tetrahydrofuran, methanol, ethanol, toluene, water or the like can be used singly or in combinations.

As the base, triethylamine, pyridine, sodium hydrogencarbonate, sodium carbonate, potassium carbonate or the like can be used singly or in combinations.

As the metal catalyst, palladium chloride, palladium acetate, tetrakis(triphenylphosphine)palladium or the like can be used.

For the purpose of improving solubility of the catalyst to reduce a use amount thereof, diazabicyclooctane which is a tertiary amine compound, tributylphosphine which is a tertiary phosphine compound, or 1-methylimidazole which is an imidazole compound may be used jointly.

Also, by again halogenating the foregoing precursor (c), an Ar-substituted compound corresponding to the compound (a) can be obtained, and hence, according to this, it is possible to obtain the precursor (c) having a different Ar. Similar to the foregoing, the halogenation is achieved by, for example, chlorine, bromine, iodine, N-bromosuccinic acid imide or iodine chloride.

By allowing acryloyl chloride (the case where R is hydrogen) or methacryloyl chloride (the case where R is a methyl group) to act on the thus obtained precursor (c) in the copresence of a base such as a tertiary amine, pyridine, an imidazole, etc., the compound represented by the formula (1) can be obtained.

I-1-10. Content

The composition for forming a holographic recording layer of the invention may contain any one kind of the reactive compound represented by the foregoing formula (1) alone, or may contain two or more kinds thereof in arbitrary combination and ratio.

A content of the subject reactive compound in the composition for forming a holographic recording layer of the invention is preferably 0.5% by weight or more and not more than 15% by weight, and especially preferably 1% by weight or more and not more than 10% by weight in terms of a ratio to the whole of solids of the composition for forming a holographic recording layer. When the content of the reactive compound is excessively small, there may be the case where the change in a refractive index is small, so that the recording efficiency becomes low. On the other hand, when the content of the reactive compound is excessively large, there may be the case where a large amount of an unreacted reactive compound remains to cause bleed-out at the time of forming into a recording material. In the case of jointly using two or more reactive compounds, the total sum thereof is regulated so as to satisfy the foregoing range.

Though the composition for forming a holographic recording layer of the invention has the photoreactive compound represented by the foregoing formula (1), it may also contain other polymerizable compound than the foregoing photoreactive compound.

Also, it is preferable that the composition for forming a holographic recording layer of the invention further contains a matrix resin and a photoinitiator.

I-2. Other Polymerizable Compound

The composition for forming a holographic recording layer of the invention may contain other polymerizable compound to an extent that the optical performance of the foregoing photoreactive compound is not conspicuously deteriorated. Examples of this polymerizable compound include cationic polymerizable monomers, anionic polymerizable monomers, radical polymerizable monomers and so forth. Any one kind of such a polymerizable compound may be used alone, or two or more kinds thereof may be jointly used in arbitrary combination and ratio.

A content of other polymerizable compound which the subject photoreactive composition further contains is preferably 0.1% by weight or more and not more than 10% by weight, and especially preferably 0.3% by weight or more and not more than 5% by weight in terms of a ratio to the whole of solids of the subject composition for forming a holographic recording layer.

Furthermore, the total sum with the content of the reactive compound represented by the foregoing formula (1) is regulated so as to satisfy the range described previously in the section of I-1-10.

I-2-1. Cationic Polymerizable Monomer

Examples of the cationic polymerizable monomer include oxirane ring-containing compounds, styrene and derivatives thereof, vinylnaphthalene and derivatives thereof, vinyl ethers, N-vinyl compounds, oxetane ring-containing compounds and so forth.

Above all, it is preferable to use at least an oxetane ring-containing compound; and it is more preferable to use an oxirane ring-containing compound together with an oxetane ring-containing compound.

Examples of the oxirane ring-containing compound include prepolymers containing two or more oxirane rings in one molecule.

Examples of such a prepolymer include alicyclic polyepoxys; polyglycidyl esters of a polybasic acid; polyglycidyl ethers of a polyhydric alcohol; polyglycidyl ethers of a polyoxyalkylene glycol; polyglycidyl ethers of an aromatic polyol; hydrogenated compounds of a polyglycidyl ether of an aromatic polyol; urethane polyepoxy compounds; epoxidated polybutadienes; and so forth.

Examples of styrene and its derivatives include styrene, p-methylstyrene, p-methoxystyrene, β-methylstyrene, p-methyl-β-methylstyrene, α-methylstyrene, p-methoxy-β-methylstyrene, divinylbenzene and so forth.

Examples of vinylnaphthalene and its derivatives include 1-vinylnaphthalene, α-methyl-1-vinylnaphthalene, β-methyl-1-vinylnaphthalene, 4-methyl-1-vinylnaphthalene, 4-methoxy-1-vinylnapthalene and so forth.

Examples of the vinyl ether include isobutyl ether, ethyl vinyl ether, phenyl vinyl ether, p-methylphenyl vinyl ether, p-methoxyphenyl vinyl ether and so forth.

Examples of the N-vinyl compound include N-vinylcarbazole, N-vinylpyrrolidone, N-vinylindole, N-vinylpyrrole, N-vinylphenothiazine and so forth.

Examples of the oxetane ring-containing compound include various known oxetane compounds disclosed in JP-A-2001-220526, JP-A-2001-310937 and so forth.

Any one kind of the above-exemplified cationic polymerizable monomers may be used alone, or two or more kinds thereof may be jointly used in arbitrary combination and ratio.

I-2-2. Anionic Polymerizable Monomer

Examples of the anionic polymerizable monomer include hydrocarbon monomers, polar monomers and so forth.

Examples of the hydrocarbon monomer include styrene, α-methylstyrene, butadiene, isoprene, vinylpyridine, vinylanthracene and derivatives thereof, and so forth.

Examples of the polar monomer include methacrylic acid esters (for example, methyl methacrylate, ethyl methacrylate, isopropyl methacrylate, etc.); acrylic acid esters (for example, methyl acrylate, ethyl acrylate, etc.); vinyl ketones (for example, methyl vinyl ketone, isopropyl vinyl ketone, cyclohexyl vinyl ketone, phenyl vinyl ketone, etc.); isopropenyl ketones (for example, methyl isopropenyl ketone, phenyl isopropenyl ketone, etc.); other polar monomers (for example, acrylonitrile, acrylamide, nitroethylene, methylene malonic acid ester, cyanoacrylic acid ester, vinylidene cyanide, etc.); and so forth.

Any one kind of the above-exemplified anionic polymerizable monomers may be used alone, or two or more kinds thereof may be jointly used in arbitrary combination and ratio.

The radical polymerizable monomer as referred to herein is a compound having one or more ethylenically unsaturated double bonds in one molecule, and examples thereof include (meth)acrylic acid esters, (meth)acrylamides, vinyl esters, styrenes and so forth.

Examples of the (meth)acrylic acid ester include methyl (meth)acrylate, ethyl (meth)acrylate, (n- or i-)propyl (meth)acrylate, (n-, i-, sec- or t-)butyl (meth)acrylate, amyl (meth)acrylate, adamantyl (meth)acrylate, chloroethyl (meth)acrylate, 2-hydroxyethyl (meth)acrylate, 2-hydroxypropyl (meth)acrylate, 2-hydroxypentyl (meth)acrylate, cyclohexyl (meth)acrylate, allyl (meth)acrylate, trimethylolpropane mono(meth)acrylate, pentaerythritol mono(meth)acrylate, benzyl (meth)acrylate, methoxybenzyl (meth)acrylate, chlorobenzyl (meth)acrylate, hydroxybenzyl (meth)acrylate, hydroxyphenethyl (meth)acrylate, dihydroxyphenethyl (meth)acrylate, furfuryl (meth)acrylate, tetrahydrofurfuryl (meth)acrylate, phenyl (meth)acrylate, hydroxyphenyl (meth)acrylate, chlorophenyl (meth)acrylate, sulfamoylphenyl (meth)acrylate, 2-phenoxyethyl (meth)acrylate, 2-(hydroxyphenylcarbonyloxy)ethyl (meth)acrylate, phenol EO-modified (meth)acrylate, p-cumylphenol EO-modified (meth)acrylate, nonylphenol EO-modified (meth)acrylate, N-acryloyloxyethyl hexahydrophthalimide, bisphenol F, EO-modified diacrylate, bisphenol A, EO-modified diacrylate, dibromophenyl (meth)acrylate, tribromophenyl (meth)acrylate, dicyclopentenyloxyethyl (meth)acrylate, dicyclopentanyl acrylate, tricyclodecanedimethylol (meth)acrylate, bisphenoxyethanolfluorene (meth)acrylate and so forth. (Incidentally, the "(meth)acrylic acid" as referred to herein is a general term for "acrylic acid" and "methacrylic acid", and the "(meth)acrylate" is also the same. Also, "EO" means "ethylene oxide".)

Examples of the (meth)acrylamide include (meth)acrylamide, N-methyl (meth)acrylamide, N-ethyl (meth)acrylamide, N-propyl (meth)acrylamide, N-butyl (meth)acrylamide, N-benzyl (meth)acrylamide, N-hydroxyethyl (meth)acrylamide, N-phenyl (meth)acrylamide, N-tolyl (meth)acrylamide, N-(hydroxyphenyl) (meth)acrylamide, N-(sulfamoylphenyl) (meth)acrylamide, N-(phenylsulfonyl) (meth)acrylamide, N-(tolylsulfonyl) (meth)acrylamide, N,N-dimethyl (meth)acrylamide, N-methyl-N-phenyl (meth)acrylamide, N-hydroxyethyl-N-methyl (meth)acrylamide and so forth.

Examples of the vinyl ester include vinyl acetate, vinyl butyrate, vinyl benzoate, benzoic acid vinyl, vinyl t-butylbenzoate, vinyl chlorobenzoate, vinyl 4-ethoxybenzoate, vinyl 4-ethylbenzoate, vinyl 4-methylbenzoate, vinyl 3-methylbenzoate, vinyl 2-methylbenzoate, vinyl 4-phenylbenzoate, vinyl pivalate and so forth.

Examples of the styrene include styrene, p-acetylstyrene, p-benzoylstyrene, 2-butoxymethylstyrene, 4-butylstyrene, 4-sec-butylstyrene, 4-tert-butylstyrene, 2-chlorostyrene, 3-chlorostyrene, 4-chlorostyrene, dichlorostyrene, 2,4-diisopropylstyrene, dimethylstyrene, p-ethoxystyrene, 2-ethylstyrene, 2-methoxystyrene, 4-methoxystyrene, 2-methylstyrene, 3-methylstyrene, 4-methylstyrene, p-methylstyrene, p-phenoxystyrene, p-phenylstyrene and so forth.

Any one kind of the above-exemplified radial polymerizable monomers may be used alone, or two or more kinds thereof may be jointly used in arbitrary combination and ratio.

Any of the above-exemplified cationic polymerizable monomer, anionic polymerizable monomer or radical polymerizable monomer can be used, and two or more kinds thereof may be used jointly. However, from the reason that the reaction for forming a resin matrix is hardly impaired, for forming a holographic recording layer, it is preferable to use a radical polymerizable monomer as other polymerizable reactive compound to be jointly used with the compound represented by the formula (1).

I-3. Matrix Resin

It is preferable that the composition for forming a holographic recording film of the invention contains a matrix resin. The matrix resin for constituting a recording layer of a holographic recording medium is an organic material which is not largely changed chemically and physically by light irradiation and is mainly constituted of an organic polymer.

The matrix resin is strongly required to have compatibility with the foregoing polymerizable reactive compound, keep a film form, have a role bearing adhesion with a substrate while keeping and reinforcing a recording layer and keeping it in a plate-like shape and have excellent compatibility with the polymerizable reactive compound, the photoinitiator and the like. When the compatibility of the matrix resin with these components is low, an interface is formed between the materials, and light is refracted or reflected at the interface, so that the light leaks into an unnecessary area. Thus, an interference fringe is warped or cut, so that an unsuitable area is recorded, resulting in deterioration of information. The compatibility of the matrix resin with other components can be evaluated on the basis of an intensity of scattered light obtained by placing a detector relative to a sample while providing an angle against transmitted light, as disclosed in, for example, Japanese Patent No. 3737306, etc.

As the matrix resin of the composition for forming a holographic recording layer of the invention, a resin which is soluble in a solvent may be used, or a three-dimensionally crosslinked resin may be used. Examples thereof include thermoplastic resins, thermosetting resins and photo-setting resins described below.

The three-dimensionally crosslinked resin is insoluble in a solvent and includes a reaction-cured material between a polymerizable compound which is liquid at ordinary temperature and a compound which is reactive with the polymerizable compound. Since the three-dimensionally crosslinked resin becomes a physical hazard, it suppresses a volumetric change at the time of recording. That is, in a recording layer after recording, a bright part is expanded, whereas a dark part is shrunk, so that irregularities are generated on the surface of a volume holographic optical recording medium. In order to suppress this volumetric change, it is more preferable to use a three-dimensionally crosslinked resin matrix for the recording layer.

Above all, from the viewpoints of compatibility and adhesion with the substrate, a thermosetting resin is preferable as the matrix resin, and a polyurethane resin obtained by a reaction of an isocyanate and a polyol is especially preferable.

I-3-1. Thermoplastic Resin

In the case of using a thermoplastic resin as the matrix resin, the recording layer of the holograph recording medium can be formed in a thermal processing process such as pressing, injection molding, etc. after mixing all of the materials and uniformly dispersing them. On that occasion, since it is necessary to melt the resin by heat, high temperatures are generally required, and there is a concern of deterioration of the polymerizable reactive compound.

Also, the recording layer of the holographic recording medium can also be formed by feeding a solution of the thermoplastic resin dissolved in a solvent onto a substrate, controlling the thickness by rotation or mechanical work, removing the solvent and then superimposing and sticking another substrate thereon. Also, the recording layer of the holographic recording medium can be formed by, after forming on a different substrate in the foregoing manner, once peeling off the resulting film from the substrate and transferring it onto another substrate, followed by interposing and sticking by another substrate. In any way, the solvent must be removed, it is difficult to prepare a thick film by one operation, and multiple works are required; and hence, there is a fear from the economical standpoint.

Examples of the specific material of the thermoplastic resin include chlorinated polyethylene, a polymethyl methacrylate resin (PMMA), a copolymer of methyl methacrylate and other alkyl acrylate, a copolymer of vinyl chloride and acrylonitrile, a polyvinyl acetate resin (PVAC), polyvinyl alcohol, polyvinyl formal, polyvinylpyrrolidone, a cellulose fiber such as ethyl cellulose, nitrocellulose, etc., a polystyrene resin, a polycarbonate resin and so forth. Any one kind of such a material may be used alone, or two or more kinds thereof may be used jointly.

A solvent for such a thermoplastic resin is not particularly limited so far as it is able to dissolve the thermoplastic resin therein. Examples thereof include ketones such as acetone or methyl ethyl ketone; esters such as butyl acetate or propylene glycol methyl ether acetate; aromatic hydrocarbons such as toluene or xylene; ethers such as tetrahydrofuran or 1,2-dimethoxyethane; amides such as N,N-dimethylacetamide or N-methylpyrrolidone; and so forth. Only one kind of such a solvent may be used alone, or a mixture of two or more kinds thereof may be used.

I-3-2. Thermosetting Resin

In the case of using a thermosetting resin as the matrix resin, the setting temperature is variable depending upon the kind of a crosslinking agent or a catalyst.

As an example of a combination of functional groups which is set at room temperature, an epoxy and an amine, an epoxy and a thiol, and an isocyanate and an amine are representative. Also, as an example of using a catalyst, an epoxy and phenol, an epoxy and an acid anhydride, and an isocyanate and a polyol are representative.

Since the former reacts immediately after mixing, it is simple and easy; however, when accompanied by molding as in a medium, the adjustment is difficult because there is no time to spare. On the other hand, the latter is suitable for setting accompanied by molding as in an optical medium because by properly choosing the kind and use amount of a catalyst, a setting temperature or a setting time can be freely chosen. Such a material can be chosen while keeping compatibility with the polymerizable reactive compound or the photoinitiator or adhesion with the substrate, or the like because resin raw materials of various kinds including low-molecular weight materials to high-molecular weight materials are commercially available.

Though the respective raw materials are hereunder described, any one kind of the raw materials may be used alone, or two or more kinds thereof may be used jointly.

<Epoxy>

Examples of the epoxy include polyglycidyl ether compounds of a polyol such as (poly)ethylene glycol, (poly)propylene glycol, (poly)tetramethylene glycol, trimethylolpropane, glycerin, etc.; alicyclic epoxy compounds having a 4- to 7-membered ring cyclic aliphatic group, such as 3,4-epoxycyclohexylmethyl-3,4-epoxycyclohexanecarboxylate, 3,4-epoxy-1-methylcyclohexyl-3,4-epoxy-1-methylhexanecarboxylate, etc.; bisphenol A type epoxy compounds; hydrogenated bisphenol A type epoxy compounds; bisphenol F type epoxy compounds; phenol or cresol novolak type epoxy compounds; and so forth.

Though the epoxy is preferably one having two or more epoxy groups in one molecule, its kind is not particularly limited. When the epoxy group number is small, there may be the case where hardness needed as the matrix is not obtained. Though an upper limit of the epoxy group number in one molecule is not particularly limited, it is usually not more than 8, and especially preferably not more than 4. When the epoxy group number is excessively large, there may be the case where a lot of time is required for consumption of the epoxy group, so that it takes too much a time for forming a matrix.

<Amine>

As the amine, those containing a primary amine group or a secondary amine group can be used. Examples of such an amine include aliphatic polyamines such as ethylenediamine, diethylenetriamine or derivatives thereof, etc.; alicyclic polyamines such as isophoronediamine, methanediamine, N-aminoethylpiperazine or derivatives thereof, etc.; aromatic polyamines such as m-xylylenediamine, diaminodiphenylmethane or derivatives thereof, etc.; polyamides such as a condensate between a dicarboxylic acid such as dimer acid, etc. and each of the foregoing polyamine, etc.; imidazole compounds such as 2-methylimidazole, etc. or derivatives thereof, etc.; and besides, dicyandiamide, adipic acid dihydrazide; and so forth.

<Thiol>

Examples of the thiol include dithiols such as 1,3-butanedithiol, 1,4-butanedithiol, 2,3-butanedithiol, 1,2-benzenedithiol, 1,3-benzenedithiol, 1,4-benzenedithiol, 1,10-decanedithiol, 1,2-ethanedithiol, 1,6-hexanedithiol, 1,9-nonanedithiol, etc. and also, EPOMATE QX10 (manufactured by Japan Epoxy Resin Co., Ltd.), EPOMATE QX11 (manufactured by Japan Epoxy Resin Co., Ltd.), etc.; polythiols such as THIOKOL (manufactured by Toray Fine Chemicals Co., Ltd.), CAPCURE 3-800 (manufactured by Japan Epoxy Resin Co., Ltd.), EPICURE QX40 (manufactured by Japan Epoxy Resin Co., Ltd.), etc.; and so forth. Of these, commercially available fast-setting polythiols such as EPOMATE QX10, EPOMATE QX11, CAPCURE 3-800, EPICURE QX40, etc. are suitably used.

<Phenol>

Examples of the phenol include phenol resins such as bisphenol A, a novolak type phenol resin, a resol type phenol resin, etc.

<Acid Anhydride>

As the acid anhydride, examples of a monofunctional acid anhydride include phthalic anhydride, tetrahydrophthalic anhydride or derivatives thereof, etc.; and examples of a difunctional acid anhydride include such as pyromellitic anhydride, benzophenonetetracarboxylic anhydride or derivatives thereof, etc.

<Use Amount of Amine, Thiol, Phenol or Acid Anhydride>

The use amount of the amine, thiol, phenol or acid anhydride is usually in the range of 0.1 equivalents or more, and especially preferably 0.7 equivalents or more, and usually not more than 2.0 equivalents, and especially preferably not more than 1.5 equivalents in terms of a proportion relative to a molar number of the epoxy group. Even when the use amount of the amine, thiol, phenol or acid anhydride is excessively small or excessively large, there may be the case where the unreacted functional group number is large, so that the storage stability is impaired.

<Polymerization Initiator>

An anionic polymerization initiator and a cationic polymerization initiator can be used as the catalyst depending upon the setting temperature or setting time.

The anionic polymerization initiator is one capable of generating an anion by light or active energy irradiation, and examples thereof include amines and so forth. Examples of the amine include amino group-containing compounds such as dimethylbenzylamine, dimethylaminomethylphenol, 1,8-diazabicyclo[5.4.0]undecene-7, etc. and derivatives thereof; imidazole compounds such as imidazole, 2-methylimidazole, 2-ethyl-4-methylimidazole, etc. and derivatives thereof; and so forth. One kind or plural kinds of such a material may be used depending upon the setting temperature or setting time.

The cationic polymerization initiator is one capable of generating a cation by light or active energy irradiation, and examples thereof include aromatic onium salts and so forth. Specific examples thereof include compounds composed of an anionic component such as $SbF_6^-$, $BF_4^-$, $AsF_6^-$, $PF_6^-$, $CF_3SO_3^-$, $B(C_6F_5)_4^-$, etc. and an aromatic cationic component containing an atom such as iodine, sulfur, nitrogen, phosphorus, etc. Of these, diaryl iodonium salts, triaryl sulfonium salts and so forth are preferable. One kind or plural kinds of such a material may be used depending upon the setting temperature or setting time.

The use amount of such an initiator is usually in the range of 0.001% by weight or more, and especially preferably 0.01% by weight or more, and usually not more than 50% by weight, and especially preferably not more than 10% by weight relative to the matrix resin. When the use amount of such an initiator is excessively small, there may be the case where the concentration of the initiator is excessively low, so that it takes too much a time for the polymerization reaction. On the other hand, when the use amount of the initiator is excessively large, there may be the case where a continuous ring-opening reaction as the polymerization reaction does not occur.

<Isocyanate>

Though the isocyanate is preferably one having two or more isocyanate groups in one molecule, its kind is not particularly limited. When the isocyanate group number in one molecule is small, there may be the case where hardness needed as the matrix resin is not obtained. Though an upper limit of the isocyanate group number in one molecule is not particularly limited, it is usually not more than 8, and especially preferably not more than 4. When the isocyanate group number in one molecule is excessively large, there may be the case where a lot of time is required for consumption of the isocyanate group, so that it takes too much a time for forming a matrix. The kind of the isocyanate is not particularly limited, so far as it has two or more isocyanate groups in one molecule. Though an upper limit of the isocyanate group number in one molecule is not particularly limited, it is usually not more than about 20.

Examples of the isocyanate which is used in the present embodiment include aliphatic isocyanates such as hexamethylene diisocyanate, lysine methyl ester diisocyanate, 2,4,4-trimethylhexamethylene diisocyanate, etc.; alicyclic isocyanates such as isophorone diisocyanate, 4,4'-methylenebis (cyclohexyl isocyanate), etc.; aromatic isocyanates such as tolylene diisocyanate, 4,4'-diphenylmethane diisocyanate, xylylene diisocyanate, naphthalene-1,5'-diisocyanate, etc.; polymers thereof; and so forth. Of these, trimers to heptamers are preferable.

Also, other examples include reaction products between water or a polyhydric alcohol such as trimethylolethane, trimethylolpropane, etc. and each of the foregoing isocyanates; polymers of hexamethylene diisocyanate; and derivatives thereof.

A molecular weight of the isocyanate which is used in the present embodiment is preferably 100 or more and not more than 50,000, more preferably 150 or more and not more than 10,000, and further preferably 150 or more and not more than 5,000 in terms of a number average molecular weight. When the number average molecular weight is excessively small, there is a possibility that since the crosslinking density increases, the hardness of the matrix resin becomes excessively high, so that the recording speed decreases. Also, when the number average molecular weight is excessively large, there may be the case where since the compatibility with other components is lowered, or the crosslinking density decreases, the hardness of the matrix resin becomes excessively low, so that the recording contents vanish.

<Polyol>

Examples of the polyol include polypropylene polyols, polycaprolactone polyols, polyester polyols, polycarbonate polyols and so forth.

(Polypropylene Polyol)

The polypropylene polyol is obtained by a reaction between propylene oxide and a diol or a polyhydric alcohol. Examples of the diol or polyhydric alcohol include ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, polyethylene glycol, polytetramethylene glycol and so forth. Examples of the polypropylene polyol which is commercially available include NEW POLE GP400 and GP1000 (all of which are a trade name, manufactured by Sanyo Chemical Industries, Ltd.); ADEKA POLYETHER G400, G700 and G1500 (all of which are a trade name, manufactured by Adeka Corporation); and so forth.

(Polycaprolactone Polyol)

The polycaprolactone polyol is obtained by a reaction between a lactone and a diol or a polyhydric alcohol. Examples of the lactone include α-caprolactone, β-caprolactone, γ-caprolactone, ε-caprolactone, α-methyl-ε-caprolactone, β-methyl-ε-caprolactone and so forth.

Examples of the diol or polyhydric alcohol include ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, polyethylene glycol, polytetramethylene glycol and so forth.

Examples of the polycaprolactone polyol which is obtained by the reaction of ε-caprolactone and which is commercially available include PLACCEL 205, PLACCEL 210, PLACCEL 220, PLACCEL 230, PLACCEL 240, PLACCEL 303, PLACCEL 305, PLACCEL 308, PLACCEL 312 and PLACCEL 320 (all of which are a trade name, manufactured by Daicel Chemical Industries, Ltd.).

(Polyester Polyol)

Examples of the polyester polyol include those obtained by polycondensation between a dicarboxylic acid or an anhydride thereof and a polyol.

Examples of the dicarboxylic acid include succinic acid, adipic acid, sebacic acid, azelaic acid, dimer acid, maleic anhydride, isophthalic acid, terephthalic acid, trimellitic acid and so forth.

Examples of the polyol include ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, polyethylene glycol, polytetramethylene glycol and so forth.

Examples of such a polyester polyol include polyethylene adipate, polybutylene adipate, polyhexamethylene adipate and so forth. Examples of the polyester polyol which is commercially available include ADEKA NEW ACE F-Series, ADEKA NEW ACE Y-Series and ADEKA NEW ACE NS-Series (all of which are a trade name, manufactured by Adeka Corporation), etc.; KURARAY POLYOL N-2010, P-4011 and P-1020 (all of which are a trade name, manufactured by Kuraray Co., Ltd.), etc.; and C-1000, C-1066, U-21, U-24, U-53, U-253, U-502 and U-118A (all of which are a trade name, manufactured by Mitsui Chemicals Polyurethane, Inc.), etc.

(Polycarbonate Polyol)

Examples of the polycarbonate polyol include those obtained by a dealcoholization condensation reaction between a glycol and a dialkyl carbonate (for example, dimethyl carbonate, diethyl carbonate, etc.); those obtained by a dephenolization condensation reaction between a glycol and a diphenyl carbonate; those obtained by a deglycolization condensation reaction between a glycol and a carbonate (for example, ethylene carbonate, diethyl carbonate, etc.); and so forth.

Examples of the glycol include aliphatic diols such as 1,6-hexanediol, diethylene glycol, propylene glycol, 1,4-butanediol, 3-methyl-1,5-pentanediol, neopentyl glycol, etc.; and alicyclic diols such as 1,4-cyclohexanediol, 1,4-cyclohexanedimetahnol, etc.

For example, there are exemplified poly(hexamethylene carbonate) polyol obtained by a condensation reaction between 1,6-hexanediol and diethyl carbonate; poly(pentylene carbonate) obtained by a condensation reaction between pentanediol and diethyl carbonate; poly(butylene carbonate) obtained by a condensation reaction between 1,4-butanedil and diethyl carbonate; and so forth.

Examples of a polycarbonate polyol which is commercially available include PLACCEL CD CD205, PLACCEL CD CD210 and PLACCEL CD CD220 (all of which are a trade name, manufactured by Daicel Chemical Industries, Ltd.); PCDL T5651, PCDL T5652 and PCDL T5650J (all of which are a trade name, manufactured by Asahi Kasei Corporation); and so forth.

(Molecular Weight of Polyol)

A molecular weight of the polyol which has been described is preferably 100 or more and not more than 50,000, more preferably 150 or more and not more than 10,000, and further preferably 150 or more and not more than 5,000 in terms of a number average molecular weight. When the number average molecular weight is excessively small, there is a possibility that since the crosslinking density increases, the hardness of the matrix resin becomes excessively high, so that the recording speed decreases. Also, when the number average molecular weight is excessively large, there may be the case where since the compatibility with other components is lowered, or the crosslinking density decreases, the hardness of the matrix resin becomes excessively low, so that the recording contents vanish.

<Other Components>

The matrix resin in the present embodiment may contain other components in addition to the foregoing respective components so far as the gist of the invention is not deviated.

Examples of such other components include hydroxyl group-containing compounds which are used for the purpose of changing physical properties of the matrix resin, such as ethylene glycol, propylene glycol, 1,4-butanediol, 1,5-pentanediol, 3-methyl-1,5-pentanediol, 1,6-hexanediol, neopentyl glycol, diethylene glycol, 1,4-cyclohexanediol, 1,4-cyclohexanedimethanol, decamethylene glycol, trimethylolpropane, polyethylene glycol, polytetramethylene glycol, etc.

Furthermore, as other components, for example, a catalyst or an additive can be blended. Though by using the catalyst, the composition can be set at room temperature, it may be set by applying a temperature. At that time, the temperature is preferably from 40° C. to 90° C.

Examples of the catalyst include usual urethane-forming reaction catalysts, for example, tin based catalysts such as dibutyltin dilaurate, dioctyltin dilaurate, dibutyltin dioctoate, etc.; and tertiary amine based catalysts such as triethylamine, triethylenedianine, etc. Of these, the tine compound is balanced in solubility and performances as the medium, and dioctyltin dilaurate is especially preferable.

The use amount of the catalyst is usually in the range of 0.0001% by weight or more, and especially preferably 0.001% by weight or more, and usually not more than 10% by weight, and especially preferably not more than 5% by weight relative to the matrix resin. When the use amount of the catalyst is excessively small, there may be the case where it takes too much a time for setting. On the other hand, when the use amount of the catalyst is excessively large, there may be the case where it becomes difficult to control the setting reaction.

I-3-3. Photo-Setting Resin

In the case of using a photo-setting resin as the matrix resin, it is necessary to achieve setting using a photoinitiator adaptive to the used wavelength. In view of the fact that when setting occurs during the light irradiation, molding or bonding is impaired, it is desirable that the setting reaction is stable in the vicinity of room temperature which is a temperature at which the operation is mainly carried out. Taking into consideration this matter, it may be said that catalytic setting with an initiator is a desirable choice.

The case where any active substrate of a radical, a cation such as a proton, etc., or an anion is formed by light irradiation is general. Accordingly, it may be considered that it would be better to choose a resin which causes setting by such an active substrate and use it as the matrix resin.

Examples of a functional group which is reactive with a radical include a vinyl group, a styryl group, an acryl group and a methacryl group. As to specific examples of a compound having such a group, examples of those having a vinyl group include vinyl butyl ether, vinyl cyclohexyl ether, etc.; examples of those having a styryl group include styrene, divinylbenzene, etc.; examples of those having an acryl group include isobornyl acrylate. 1,4-butane diacrylate, etc.; and examples of those having a methacryl group include methyl methacrylate, phenoxyethyl methacrylate, etc.

Examples of a functional group which is reactive with a cation such as a proton, etc. include an epoxy group and an oxetanyl group. As to specific examples of a compound having such a group, examples of those having an epoxy group include polyglycidyl ether compounds of a polyol such as (poly)ethylene glycol, (poly)propylene glycol, (poly)tetramethylene glycol, trimethylolpropane, glycerin, etc.; alicyclic epoxy compounds having a 4- to 7-membered ring cyclic aliphatic group, such as 3,4-epoxycyclohexylmethyl-3,4-epoxycyclohexanecarboxylate, 3,4-epoxy-1-methylcyclohexyl-3,4-epoxy-1-methylhexanecarboxylate, etc.; bisphenol A type epoxy compounds; hydrogenated bisphenol A type epoxy compounds; bisphenol F type epoxy compounds; phenol or cresol novolak type epoxy compounds; and so forth. Examples of those having an oxetanyl group include 2-ethyl-2-oxetanyl ether of bisphenol A, 1,6-bis(2-ethyl-2-oxetanyl) hexane and so forth. (Incidentally, the term "(poly)ethylene glycol" or the like means both "ethylene glycol" and "polyethylene glycol" as its polymer).

Examples of a functional group which is reactive with an anion include an epoxy group and an episulfide group. Specific examples of an episulfide group-containing compound include phenyl episulfide, diepisulfide methyl ether of bisphenol A and so forth.

Also, examples of an initiator capable of forming a radical as the active substrate include peroxides such as tert-butyl peroxide, etc.; and diazo compounds such as azoisobutyronitrile, etc.

The use amount of the photoinitiator which is used in the case of photo-setting the foregoing matrix resin is usually in the range of 0.01% by weight or more, and especially preferably 0.1% by weight or more, and usually not more than 1% by weight, and especially preferably not more than 30% by weight in terms of a ratio to the polymerizable compound. When the use amount of the initiator is excessively small, there may be the case where it takes too much a time for setting. On the other hand, when the use amount of the initiator is excessively large, there may be the case where it becomes difficult to control the setting reaction.

Also, since when recorded, light is also irradiated, it is important that the wavelength at the time of setting is different from the wavelength at the time of recording, and a difference of the wavelength is at least 10 nm, and preferably 30 nm. The choice of the initiator can be generally expected from the absorption wavelength of the initiator.

I-4. Photoinitiator

Any photoinitiator can be used so far as it is a known photo-radical polymerization initiator. Examples thereof include azo based compounds, azide based compounds, organic peroxides, organic boronic acid salts, onium salts, bisimidazole derivatives, titanocene compounds, iodonium salts, organic thiol compounds, halogenated hydrocarbon derivatives and so forth. Any one kind of such a compound may be used alone, or two or more kinds thereof may be jointly used in arbitrary combination and ratio. Of these, from the reason that a polymerization reaction occurs in a visible light region, titanocene compounds, acylphosphine oxide compounds, oxime ester compounds and so forth are preferable as the photoinitiator.

I-4-1. Titanocene Compound

In the case of using a titanocene compound as the photoinitiator, though it is not particularly limited with respect to a kind thereof, it can be properly chosen and used among various titanocene compounds disclosed in, for example, JP-A-59-152396, JP-A-61-151197, etc.

Specific examples of the titanocene compound include dicyclopentadienyl-Ti-dichloride, dicyclopentadienyl-Ti-bisphenyl, dicyclopentadienyl-Ti-bis-2,3,4,5,6-pentafluorophen-1-yl, dicyclopentadienyl-Ti-bis-2,3,5,6-tetrafluorophen-1-yl, dicyclopentadienyl-Ti-bis-2,4,6-trifluorophen-1-yl, dicyclopentadienyl-Ti-bis-2,6-difluorophen-1-yl, dicyclopentadienyl-Ti-bis-2,4-difluorophen-1-yl, dimethylcyclopentadienyl-Ti-bis-2,3,4,5,6-pentafluorophen-1-yl, dimethylcyclopentadienyl-Ti-bis-2,3,5,6-tetrafluorophen-1-yl, dimethylcyclopentadienyl-Ti-bis-2,6-difluorophen-1-yl, dicyclopentadienyl-Ti-bis-2,6-difluoro-3-(pyr-1-yl)-pheny-1-yl and so forth.

I-4-2. Acylphosphine Oxide Compound

Specific examples of the acylphosphine oxide compound include monofunctional initiators having only one cleavage point by light in one molecule and bifunctional initiators having two cleavage points in one molecule.

Examples of such a monofunctional initiator include triphenylphosphine oxide, 2,4,6-trimethylbenzoyldiphenylphosphine oxide, 2,6-dicyclobenzoyldiphenylphosphine oxide and so forth.

Examples of such a bifunctional initiator include bis(2,4,6-trimethylbenzoyl)-phenylphosphine oxide, bis(2,6-dimethoxybenzoyl)-2,4,4-trimethylpentylphosphine oxide, bis(2,6-dichlorobenzoyl)-4-propylphenylphosphine oxide, bis(2,6-dichlorobenzoyl)-2,5-dimethylphenylphosphine oxide and so forth.

I-4-3. Oxime Ester Based Compound

Specific examples of the oxime ester based compound include those having the following structure.

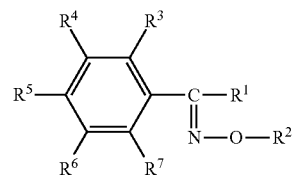

[Formula 13]

Specific examples thereof include 1-[4-(phenylthio)-2-(O-benzoyloxime)]-1,2-octanedione, 1-[9-ethyl-6-(2-methylbenzoyl)-9H-carbazol-3-yl]-1-(O-acetyloxime)ethanone and so forth.

I-4-4. Use Amount of Photoinitiator

Any one kind of the foregoing every photoinitiator may be used alone, or two or more kinds thereof may be jointly used in arbitrary combination and ratio.

A content of the photoinitiator in the composition for forming a holographic recording layer of the invention is usually in the range of 0.1% by weight or more, and especially preferably 0.5% by weight or more, and usually not more than 20% by weight, and especially preferably not more than 15% by weight in terms of a ratio to the whole of solids of the composition for forming a holographic recording layer. When the content of the photoinitiator is excessively small, there may be the case where since the generation amount of a radical is small, the speed of photopolymerization becomes slow, so that the holographic recording sensitivity becomes low. On the other hand, when the content of the photoinitiator is excessively large, there may be the case where since the radicals generated by light irradiation are recoupled with each other, or disproportionation is caused, the photoinitiator less contributes to the photopolymerization, so that the holographic recording sensitivity becomes low, too. In the case of jointly using two or more photoinitiators, the total sum thereof is regulated so as to satisfy the foregoing range.

I-5. Other Components

The composition for forming a holographic recording layer of the invention may contain other components in addition to the foregoing components so far as the gist of the invention is not deviated.

For example, an arbitrary additive can be blended depending upon control of excitation wavelength or excitation energy of a sensitizer, control of the reaction, improvements of characteristics and so forth.

Examples of the additive include the following compounds.

For example, a compound capable of controlling excitation of a sensitizer can be added. In that case, examples thereof include a sensitizing agent, a sensitization auxiliary and so forth.

The sensitizing agent can be arbitrarily chosen and used among various known sensitizing agents. In general, in many cases, a colored compound such as a coloring matter, etc. is used as the sensitizing agent for the purpose of absorbing visible and ultraviolet laser lights. Though the sensitizing agent varies depending upon the wavelength of laser light and the kind of the initiator to be used, specific examples of the preferred sensitizing agent include compounds disclosed in JP-A-5-241338, JP-A-2-69, JP-B-2-55446, etc. in the case of a system using green laser; and compounds disclosed in JP-A-2000-10277, JP-A-2004-198446, etc. in the case of a system using blue laser. Any one kind of the above-exemplified every sensitizing agent may be used alone, or two or more kinds thereof may be jointly used in arbitrary combination and ratio.

Incidentally, in the case where colorless transparency is required for the obtained holographic recording medium or holographic recording material, it is preferable to use a cyanine based coloring matter as the sensitizing agent. That is, since in general, the cyanine based coloring matter is easily decomposed by light, by performing post exposure, namely allowing it to stand under room light or sunlight for from several hours to several days, the cyanine based coloring matter in the holographic recording medium or holographic recording material is decomposed to have no absorption in a visible light region, thereby obtaining a colorless transparent holographic recording medium or holographic recording material.

Though the amount of the sensitizing agent must be increased or decreased depending upon the thickness of the recording layer to be formed, it is usually in the range of 0.01% by weight or more, and especially preferably 0.1% by weight or more, and usually not more than 10% by weight, and especially preferably not more than 5% by weight in terms of a ratio to the photoinitiator of II-4. When the use amount of the sensitizing agent is excessively small, there may be the case where the initiation efficiency becomes low, so that it takes too much a time for recording. On the other hand, when the use amount of the sensitizing agent is excessively large, there may be the case where the absorption of light to be used for recording or reproduction becomes large, so that the light hardly reaches the depth direction. In the case of jointly using two or more sensitizing agents, the total sum thereof is regulated so as to satisfy the foregoing range.

A plasticizer for enhancing the reaction efficiency or regulating physical properties of the recording layer, an additive for controlling the water absorption of the recording layer or the like, and so forth can be used as other additives than those described above.

Examples of the plasticizer include phthalic acid esters such as dioctyl phthalate, diisononyl phthalate, diisodecyl phthalate, diundecyl phthalate, etc.; adipic acid esters such as bis(2-ethylhexyl) adipate, diisononyl adipate, di-n-butyl adipate, etc.; sebacic acid esters such as dioctyl sebacate, dibutyl sebacate, etc.; phosphoric acid esters such as tricresyl phosphate, etc.; citric acid esters such as tributyl acetylcitrate, etc.; trimellitic acid esters such as trioctyl trimellitate, etc.; epoxidized soybean oil; chlorinated paraffin; alkoxylated (poly)alkylene glycol esters such as acetoxymethoxypropane, etc.; alkoxy-terminated polyalkylene glycols such as dimethoxypolyethylene glycol, etc.; and so forth.

Such a plasticizer is used in an amount usually in the range of from 0.01% by weight or more and not more than 50% by weight, and preferably of from 0.05% by weight or more and not more than 20% by weight in terms of a ratio to the whole of solids of the composition for forming a holographic recording layer. When the use amount of the plasticizer is smaller than this range, the effects for enhancing the reaction efficiency and regulating the physical properties are not exhibited, whereas when it is more than this range, the transparency of the recording layer becomes low, or bleed-out of the plasticizer becomes conspicuous, and hence, such is not preferable.

Furthermore, a compound which is used for controlling the reaction can also be added. In that case, examples thereof include a polymerization initiator, a chain transfer agent, a polymerization inhibitor, a compatibilizing agent, a reaction auxiliary and so forth.

Besides, examples of additives which may be needed for improving characteristics include a dispersant, a defoaming agent, a plasticizer, an antiseptic, a stabilizer, an antioxidant, an ultraviolet light absorber and so forth.

Any one kind of such an additive may be used alone, or two or more kinds thereof may be jointly used in arbitrary combination and ratio.

The use amount of such an additive is usually in the range of 0.001% by weight or more, and especially preferably 0.01% by weight or more, and usually not more than 30% by weight, and especially preferably not more than 10% by weight relative to the whole of solids of the composition for forming a holographic recording layer of the present embodiment. In the case of jointly using two or more additives, the total sum thereof is regulated so as to satisfy the foregoing range.

II. Holographic Recording Material of the Invention

The holographic recording material of the invention comprises the foregoing composition for forming a holographic recording layer of the invention.

The holographic recording material of the invention may be composed only of the composition for forming a holographic recording layer of the invention, or may contain other component. Also, any one kind of the composition for forming a holographic recording layer of the invention may be used alone, or two or more kinds thereof may be jointly used in arbitrary combination and ratio. In the case where the holographic recording material of the invention contains other component, a content of the reactive compound in the holographic recording material of the invention is preferably 0.5% by weight or more and not more than 15% by weight, and especially preferably 1% by weight or more and not more than 10% by weight in terms of a ratio to the whole of solids of the holographic recording materials. In the case of jointly using two or more compositions for forming a holographic recording layer, the total sum of the reactive compounds contained in the respective compositions for forming a holographic recording layer is regulated so as to fall within the foregoing range. Also, though other component is not particularly limited, examples thereof include various additives such as an optical dispersant, a coloring material, etc. A content of other component is arbitrary so far as the effects of the present embodiment are not conspicuously impaired.

III. Holographic Recording Medium of the Invention

The holographic recording medium of the invention comprises a recording layer containing one or two or more kinds of the reactive compound represented by the foregoing formula (1) and optionally, a support and other layer, wherein a rate of shrinkage of the recording layer by batch exposure is not more than 0.25%.

Also, in the recording layer of this holographic recording medium, a value of M/# is preferably 10 or more, and a value of (M/#)/(rate of shrinkage by batch exposure) is preferably 100 or more.

Incidentally, as described in detail in the section of recording method as described later, the reactive compound represented by the foregoing formula (1) of the invention, which is contained in the subject recording layer, is a compound, a part of which causes a chemical change such as polymerization, etc. by holographic recording or the like. In consequence, in the holographic recording medium after recording, a part of the reactive compound represented by the foregoing formula (1) of the invention is consumed and exists as a compound after the reaction, such as a polymer, etc. Though it may be considered that a consumption amount of the subject reactive compound also fluctuates depending upon the recording information amount, in the case of undergoing a step of so-called "post exposure", in which after recording a data, a recorded portion is uniformly irradiated with light, thereby venturing the remaining reactive compound to consume, the majority of the subject reactive compound is converted to a compound after the reaction.

The recording layer of the holographic recording medium of the invention is preferably formed of the composition for forming a holographic recording layer or holographic recording material of the invention.

In general, the holographic recording medium has a support, and a recording layer and other layer are laminated on this support, thereby configuring the holographic recording medium. However, in the case of the recording layer or other layer has strength or durability needed for the medium, the holographic recording medium may not have a support.

Examples of other layer include a protective layer, a reflection layer, an antireflection layer (antireflection film) and so forth.

III-1. Recording Layer

The recording layer of the holographic recording medium of the invention is preferably formed of the composition for forming a holographic recording layer or holographic recording material of the invention. The recording layer is a layer on which information is recorded. In general, the information is recorded as a hologram. As described in detail in the section of recording method as described later, the reactive compound contained in the subject recording layer is a compound, a part of which causes a chemical change such as polymerization, etc. by holographic recording or the like. In consequence, in the holographic recording medium after recording, a part of the reactive compound is consumed and exists as a compound after the reaction, such as a polymer, etc. In consequence, the reactive compound represented by the foregoing formula (1) and after holographic recording, also the compound after the reaction are usually contained in a total amount of 0.5% by weight or more and not more than 15% by weight, and preferably 1% by weight or more and not more than 10% by weight in the recording layer of the holographic recording medium of the invention. In the case where other reactive compound than the reactive compound represented by the foregoing formula (1) is contained in the recording layer of the holographic recording medium of the invention, the total sum thereof including other reactive compound than the reactive compound represented by the foregoing formula (1) and the compound after the reaction is regulated so as to satisfy the foregoing range.

A thickness of the recording layer is not particularly limited, and it may be properly determined while taking into consideration the recording method or the like. In general, the thickness of the recording layer is usually in the range of 1 μm or more, and preferably 10 μm or more, and usually not more than 1 cm, and preferably not more than 2,000 μm. When the recording layer is excessively thick, there may be the case where during multiplex recording in the holographic recording medium, selectivity of each hologram becomes low, so that the degree of multiplex recording becomes low. Also, when the recording layer is excessively thin, there may be the case where it is difficult to uniformly mold the whole of the recording layer, so that it becomes difficult to achieve multiplex recording with uniform diffraction efficiency and high S/N ratio in each hologram.

III-2. Support

The support is not particularly limited regarding its details so far as it has strength and durability needed for the medium, and an arbitrary support can be used. Also, though the support is not limited regarding its shape, it is usually formed in a plate shape or film shape.

Also, a material constituting the support is not limited, and it may be either transparent or opaque. Examples of a transparent material of the support include organic materials such as an acrylic resin, polyethylene terephthalate, polyethylene naphthoate, polycarbonate, polyethylene, polypropylene, an amorphous polyolefin, polystyrene, cellulose acetate, etc.; and inorganic materials such as glass, silicon, quartz, etc. Of these, polycarbonate, an acrylic resin, a polyester, an amorphous polyolefin, glass and so forth are preferable; and in particular, polycarbonate, an acrylic resin, an amorphous polyolefin and glass are more preferable.

On the other hand, examples of an opaque material on the support include metals such as aluminum, etc.; and those obtained by coating a metal such as gold, silver, aluminum, etc. or a dielectric such as magnesium fluoride, zirconium oxide, etc. on the foregoing transparent support.

Though a thickness of the support is not particularly limited, it is usually in the range of 0.1 mm or more and not more than 1 mm. When the support is excessively thin, there may be the case where the mechanical strength of the holographic recording medium is insufficient, so that the substrate warps, whereas when it is excessively thick, there may be the case where the transmission amount of light decreases, so that the cost becomes higher.

Also, the surface of the support may be subjected to a surface treatment. This is usually performed for the purpose of enhancing adhesiveness between the support and the recording layer. Examples of the surface treatment include a corona discharge treatment on the support and previous formation of an undercoat layer on the support. Here, examples of a composition for the undercoat layer include a halogenated phenol or partially hydrolyzed vinyl chloride/vinyl acetate copolymer, a polyurethane resin and so forth.

Furthermore, the surface treatment may be performed for other purpose than an enhancement of the adhesiveness. Examples thereof include a reflection coating treatment of forming a reflection coating layer made of, as a raw material, a metal such as gold, silver, aluminum, etc.; and a dielectric coating treatment of forming a dielectric layer made of magnesium fluoride, zirconium oxide, etc. Also, such a layer may be formed of a single layer, or may be formed of two or more layers.

Also, such a surface treatment may be conducted for the purpose of controlling transmissivity of the substrate against a gas or moisture. By bearing a work to suppress transmissivity against a gas or moisture on the support interposing the recording layer, reliability of the medium can be enhanced much more.

Also, the support is provided on either one or both of an upper side and a lower side of the recording layer of the holographic recording medium of the present embodiment. However, in the case where the support is provided on both of the upper and lower sides of the recording layer, at least one of the supports is constructed to be transparent so as to transmit active energy rays (excitation light, reference light, reproduction light, etc.) therethrough.

In the case of the holographic recording medium having a support on one side or both sides of the recording layer, a transmission type or reflection type hologram can be recorded. Also, in the case of using a support having reflection characteristics on one side of the recording layer, a reflection type hologram can be recorded.

Furthermore, a patterning for data address may be provided on the support. In that case, though the patterning method is not limited, for example, irregularities may be formed on the support per se; a pattern may be formed on a reflection layer (as described later); or a pattern may be formed by a combination of these methods.

III-3. Protective Layer

The protective layer is a layer for preventing adverse influences such as reduction in sensitivity or deterioration in storage stability due to oxygen or moisture, etc. A specific configuration of the protective layer is not limited, and known configurations can be arbitrarily applied. For example, a layer made of a water-soluble polymer, an organic/inorganic material or the like can be formed as the protective layer.

III-4. Reflection Layer

The reflection layer is formed during constructing the holographic recording medium in a reflection type. In the case of a holographic recording medium of a reflection type, the reflection layer may be formed between the support and the recording layer, or may be formed on the outer surface of the support. In general, the reflection layer is preferably located between the support and the recording layer.

III-5. Antireflection Film

With respect to all of holographic recording media of a transmission type or a reflection type, an antireflection film may be provided on the side on which object light and reading light come in and outgo, or between the recording layer and the support. The antireflection film works to enhance the use efficiency of light and suppress the generation of a ghost image.

III-6. Manufacturing Method

A method for manufacturing the holographic recording medium of the invention is not limited.

For example, the holographic recording medium of the invention can be manufactured by coating the photoreactive composition of the invention on a support in the absence of a solvent to form a recording layer. On that occasion, an arbitrary method can be used as the coating method. Specific examples thereof include a spraying method, a spin coating method, a wire bar method, a dipping method, an air knife coating method, a roll coating method, a blade coating method, a doctor roll coating method and so forth.

Also, in the formation of a recording layer, in particular, in the case of forming a thick recording layer, a method of charging the composition in a die and molding it, or a method of coating the composition on a mold release film and subjecting it to die punching can also be adopted.

Also, the holographic recording medium of the invention may also be manufactured by mixing the photoreactive composition of the invention and a solvent or an additive to prepare a coating solution, coating this on a support and then drying it to form a recording layer. In that case, an arbitrary method can be used as the coating method, and for example, the same method as that described above can be adopted.

Also, though the solvent is not limited, in general, it is preferable to use a solvent which has a sufficient solubility against the components to be used, is able to give good coating film properties and does not affect a support such as a resin substrate, etc.

Examples of the solvent include ketone based solvents such as acetone, methyl ethyl ketone, methyl isobutyl ketone, cyclohexanone, methyl amyl ketone, etc.; aromatic solvents such as toluene, xylene, etc.; alcohol based solvents such as methanol, ethanol, propanol, n-butanol, heptanol, hexanol, diacetone alcohol, furfuryl alcohol, etc.; ketone alcohol based solvents such as diacetone alcohol, 3-hydroxy-3-methyl-2-butanone, etc.; ether based solvents such as tetrahydrofuran, dioxane, etc.; halogen based solvents such as dichloromethane, dichloroethane, chloroform, etc.; cellosolve based solvents such as methyl cellosolve, ethyl cellosolve, butyl cellosolve, methyl cellosolve acetate, ethyl cellosolve acetate, etc.; propylene glycol based solvents such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, dipropylene glycol dimethyl ether, etc.; ester based solvents such as ethyl acetate, butyl acetate, amyl acetate, butyl acetate, ethylene glycol diacetate, diethyl oxalate, ethyl pyruvate, ethyl-2-hydroxybutyrate, ethyl acetoacetate, methyl lactate, ethyl lactate, methyl 2-hydroxyisobutyrate, methyl 3-methoxypropionate, etc.; perfluoroalkyl alcohol based solvents such as tetrafluoropropanol, octafluoropentanol, hexafluorobutanol, etc.; highly polar solvents such as dimethylformamide, dimethylacetamide, N-methylpyrrolidone, dimethyl sulfoxide, etc.; chain hydrocarbon based solvents such as n-hexane, n-octane, etc.; cyclic hydrocarbon based solvents such as cyclohexane, methylcyclohexane, ethylcyclohexane, dimethylcyclohexane, n-butylcyclohexane, tert-butylcyclohexane, cyclooctane, etc.; mixed solvents thereof; and so forth.

Any one kind of such a solvent may be used alone, or two or more kinds thereof may be jointly used in arbitrary combination and ratio.

Also, the use amount of the solvent is not limited. However, from the standpoints of coating efficiency and handling properties, it is preferable to prepare a coating solution having a solids concentration of from about 1% to 1,000% by weight.

Furthermore, in the case where the photoreactive composition of the invention is thermoplastic, the recording layer can be manufactured by molding the photoreactive composition of the invention by, for example, an injection molding method, a sheet molding method, a hot press method, etc.; and in the case where the photoreactive composition of the invention is (photo)thermosetting and has a small content of a volatile component, the recording layer can be manufactured by molding the photoreactive composition of the invention by, for example, a reactive injection molding method or a liquid injection molding method. In that case, so far as a molded product has sufficient thickness, rigidity and strength, etc., the subject molded product can be formed into an optical recording medium as it is.

Also, examples of the method for manufacturing an optical recording medium include a method for manufacturing an optical recording medium by coating the photoreactive composition fused by heat on a support and solidifying it by cooling to form a recording layer; a method for manufacturing an optical recording medium by coating the liquid photoreactive composition on a support and setting it by heat polymerization to form a recording layer; a method for manufacturing an optical recording medium by coating the liquid photoreactive composition on a support and setting it by photopolymerization; and so forth.

The thus manufactured optical recording medium can take a form of a self-supporting slab or disc and can be used for three-dimensional image display apparatuses, diffraction optical devices, large-capacity memories and others.

III-7. Recording/Reproducing Method of Information

All of writing (recording) and reading (reproduction) of information on the holographic recording medium of the present embodiment are conducted by light irradiation.

First of all, at the time of recording the information, light capable of generating a chemical change of the polymerizable reactive compound, for example, polymerization and concentration change in the case of a polymerizable monomer, is used as object light (also called recording light).

In particular, in the holographic recording medium of the present embodiment, since the information is recorded as a volume hologram, the object light is irradiated on the recording layer together with reference light, thereby allowing the object light and the reference light to interfere with each other. According to this, its interference light causes a change (for example, polymerization and concentration change) in the polymerizable reactive compound within the recording layer, and as a result, an interference fringe causes a difference in a refractive index within the recording layer, and a hologram is recorded on the recording layer due to the interference fringe recorded within the recording layer.

On the other hand, in the case of reproducing a volume hologram recorded on the recording layer, prescribed reproduction light (usually, reference light) is irradiated on the recording layer. The irradiated reproduction light causes diffraction depending upon the foregoing interference fringe. Since this diffracted light includes the same information as in the foregoing recording layer, by reading the foregoing diffracted light by a detector, the information recorded on the recording layer can be reproduced.

Incidentally, the wavelength region of each of the object light, reproduction light and reference light is arbitrary depending upon an application thereof, and it may be either a visible light region or an ultraviolet light region. Of these lights, for example, lasers with excellent monochromaticity and directivity such as solid lasers such as ruby, glass, Nd—YAG, Nd—$YVO_4$, etc.; diode lasers such as GaAs, InGaAs, GaN, etc.; gas lasers such as helium-neon, argon, krypton, excimer, $CO_2$, etc.; dye lasers having a coloring matter; etc. are suitable.

Also, an irradiation dose of each of the object light, reproduction light and reference light is not limited, and the irradiation dose is arbitrary so far as it falls within the range where recording and reproduction can be achieved. However, in the case where the irradiation dose is extremely small, the chemical change of the polymerizable reactive compound becomes too incomplete, so that there is a concern that the heat resistance or mechanical characteristic of the recording layer is not sufficiently revealed; whereas in the case where it is extremely large, there is a concern that the component of the recording layer (the volume holographic recording material of the invention) causes deterioration.

In consequence, each of the object light, reproduction light and reference light is usually irradiated at a dose in the range of 0.1 $J/cm^2$ or more and not more than 20 $J/cm^2$ in conformity with the composition of the volume holographic recording material of the invention, which is used for forming a recording layer, and the kind and blending amount of the photo initiator, etc.

Also, the holographic recording mode includes a polarized collinear holographic recording mode, a reference light incidence angle multiplexing holographic recording mode, etc. In the case of using the holographic recording medium or volume holographic recording material of the present embodiment as a recording medium, it is possible to provide a good recording quality in any of the recording modes.

III-8. Performance

The holographic recording medium of the present embodiment has such a characteristic feature that the diffraction efficiency and light transmittance are high and that the rate of shrinkage is small.

III-8-1. M/# (M Number)

A difference in a refractive index between a recorded area and an unrecorded area generated by holographic recording is measured as a diffraction efficiency at every exposure energy to be applied. The exposure energy to be applied is measured according to procedures for multiplex recording. The multiplexing method is carried out by a method, for example, angle multiplexing with intersecting lights at a fixed angle while changing an incidence angle, shift multiplexing while shifting the place without changing an incidence angle, or wavelength multiplexing while changing the wavelength. However, the angle multiplexing is simple and easy, and according to this, performances of the material and each of the components can be grasped.

In multiplex recording, since M/# (M number) which is a sum of the diffraction efficiencies is a numerical value which is a standard of the recording capacity, it may be said that when M/# (M number) is large, a good performance as the medium is revealed.

In general, the higher the content of the photoreactive compound, the larger the diffraction efficiency is, and the larger the M/# is.

In the case where the recording layer of the holographic recording medium of the present embodiment is evaluated as a 500 μm-thick recording layer, its M/# is usually 10 or more, preferably 12 or more, and especially preferably 15 or more.

Incidentally, as described previously, it is preferable that the M/# value is large as far as possible, and there is no distinct upper limit. For example, in order to attain a recording capacity of 1 TB, an M/# value of about 100 is needed.

Incidentally, as described previously, M/# (M number) of the recording layer according to the invention is a value evaluated regarding the 500 μm-thick recording layer.

That is, so far as a medium for evaluation as shown in the section of working examples as described later is fabricated in the same manner, except that a recording layer provided regarding a certain holographic recording medium is regulated to have a thickness of 500 μm, and this medium for evaluation has an M/# (M number) of 10 or more, especially 12 or more, and more especially 15 or more, it may be said that this medium for evaluation is suitable as the holographic recording medium in the invention.

This M/# (M number) is measured by the method in the section of working examples as described later.

Alternatively, in the case of a recording medium in which a recording layer thickness is not 500 μm, so far as this medium is evaluated regarding M/# in the same manner, and the result obtained by converting the M/# value into a value at a recording layer thickness of 500 μm reveals 10 or more, especially 12 or more, and more especially 15 or more, it may be said that this medium is suitable as the holographic recording medium in the invention.

In general, there is a tendency that when the recording layer thickness increases, the M/# value also increases.

In the recording layer thickness of from 200 to 700 μm, the recording layer thickness and M/# are substantially in proportion to each other. Thus, it is possible to compare results obtained by evaluating media having a recording layer falling within this thickness range by correcting the thickness through proportional conversion.

On the other hand, in the range where the recording layer thickness exceeds 1,000 μm, an increase of M/# relative to the recording layer thickness becomes gentle, and it is difficult to make comparison by correcting the thickness through simple proportional calculation. In that case, it is possible to choose a composition of a recording layer in which it has been previously known that M/# falls within the foregoing numerical value range in a thickness of 500 μm, fabricate a 500 μm-thick medium and a medium having a thickness corresponding to a recording layer thickness of an actual medium which is an object to the evaluation and convert an M/# value of the actual medium into an M/# value in a thickness of 500 μm on the basis of correlation of the both.

Also, since other layers than the recording layer configuring the holographic recording medium, such as a substrate, a protective layer, a reflection layer, etc., do not largely influence the M/# value, it is also possible to make direct comparison of M/# with respect to media having a different layer configuration except for the recording layer.

III-8-2. Light Transmittance

The measurement of light transmittance is an important index in achieving recording with light. It may be said that the fact that the light transmittance is high before recording is a good performance in enhancing the capacity by achieving recording to a deeper recording layer. Similarly, it may be said that the fact that the light transmittance is high even after recording is a good performance because an error can be minimized in reproducing the record.

It is desirable that the light which is used for measuring this light transmittance has a wavelength the same as that to be recorded or in the vicinity thereof. However, since the chemical change of the photoinitiator within the recording layer before recording becomes conspicuous, and the degree of transmission changes with time, the light transmittance must be measured within a sufficiently short time. If only attention is paid to this point, the light transmittance can be measured without problem, and a measured value with reliability and reproducibility can be obtained. The "sufficiently short time" as referred to herein is generally not more than about one second. So far as the measurement is performed after recording, since the photoinitiator does not cause a change with time upon being consumed, the measurement time need not be kept in mind.

In general, though this light transmittance is preferably close to 100%, it is generally 60% or more, and especially preferably 80% or more. So far as the holographic recording medium of the present embodiment is concerned, in the case where the evaluation is achieved in the recording layer thickness of 500 μm, a value of usually 60% or more, and preferably 70% or more can be attained as the light transmittance before recording, and a value of usually 60% or more, and preferably 70% or more can be attained as the light transmittance after recording. Incidentally, this light transmittance is specifically measured by the method described in the section of working examples as described later.

Also, in the case of a recording medium in which a recording layer thickness is not 500 μm, so far as this medium is evaluated regarding the light transmittance in the same manner, and the result obtained by converting the light transmittance into a value at a recording layer thickness of 500 μm reveals 60% or more, and preferably 70% or more, it may be said that this medium is suitable as the holographic recording medium in the invention.

In general, the light transmittance is influenced by the recording layer thickness, and exclusive of the case where the light transmittance is 100%, there is a tendency that the thicker the recording layer thickness, the lower the light transmittance becomes. In the recording layer thickness of from 200 to 700 μm, the recording layer thickness and the light transmittance are substantially in inverse proportion to each other. Thus, it is possible to compare results obtained by evaluating media having a recording layer falling within this thickness range by correcting the thickness through inverse-proportional conversion. On the other hand, in the range where the recording layer thickness exceeds 1,000 μm, exclusive of the case where the light transmittance is 100%, a reduction of the light transmittance relative to the recording layer thickness abruptly decreases as compared with that in the inverse proportion relation in the recording layer thickness of from 200 to 700 μm, and it is difficult to make simple conversion.

Incidentally, the transparent layers other than the recording layer configuring the holographic recording medium, such as the substrate, the protective layer, etc., usually have a sufficiently large light transmittance relative to the recording layer, and a value of the light transmittance as the medium can be regarded substantially as a transmittance of the recording layer. In the case of a recording medium having an opaque layer such as a reflection layer, etc., the thickness of the reflection layer is sufficiently thin as not more than 1/10 as compared with that of the recording layer, the substrate or the like, and therefore, an influence of the light transmittance against the medium can be neglected. In this way, it is also possible to make direct comparison of the light transmittance with respect to media having a different layer configuration except for the recording layer.

III-8-3. Rate of Shrinkage

When after less angle multiplex recording, the remaining reactive compound is consumed by allowing it to react by a method such as batch exposure, etc., a rate of shrinkage by batch exposure can be measured by again measuring the angle. It may be said that when a change of the angle is small, namely the rate of shrinkage is small, a good performance is revealed as the medium.

In the recording layer provided in the holographic recording medium of the present embodiment, for example, in the case where the evaluation is achieved in the recording layer thickness of 500 μm, the rate of shrinkage by batch exposure (hereinafter also referred to simply as "rate of shrinkage") is usually not more than 0.25%, preferably not more than 0.20%, and especially preferably not more than 0.15%. Also, in the case where when a monomer is polymerized with high packing properties, expansion inversely occurs, or in the case where the reaction is accompanied with expansion as in a ring-opening reaction, it is also expected that the rate of shrinkage inversely exhibits a minus value. However, in that case, it is also assumed that the performance as a medium is not good as in the case of shrinkage. Accordingly, the value of the rate of shrinkage is preferably close to zero as far as possible, and most preferably zero. This rate of shrinkage is specifically measured by the method in the section of working examples as described later.

In general, even when the recording layer thickness becomes thick, the rate of shrinkage by batch exposure should not change, and in the recording layer thickness of from 200 to 700 μm, the rate of shrinkage generally exhibits the same value. In consequence, so far as the rate of shrinkage falls within this range, it is also possible to make direct comparison of the rate of shrinkage with respect to media whose recording layer thickness is not 500 μm.

On the other hand, similar to the light transmittance, with respect to the range where the recording layer thickness exceeds 1,000 μm, the rate of shrinkage is smaller than that in the recording layer thickness of from 200 to 700 μm, exclusive of the case that the light transmittance relative to the recording layer thickness is 100%.

Incidentally, since so far as the evaluation is performed in the foregoing method, other layers than the recording layer configuring the holographic recording medium, such as a substrate, a protective layer, a reflection layer, etc., do not largely influence the value of the rate of shrinkage, it is also possible to make direct comparison of the rate of shrinkage with respect to media having a different layer configuration except for the recording layer.

III-8-4. (M/#)/(Rate of Shrinkage)

Though the foregoing rate of shrinkage is suitably low, since it is an index for the change before and after recording, even by exposure, in an unrecorded area, the rage of shrinkage does not change and becomes zero, and it is not sufficient to evaluate the recording performance with a size of this value.

As described previously, since M/# strongly depends upon the addition amount of the photoreactive compound, it may be said that assuming that a balance with this can be taken, a high-performance medium can be obtained. However, in general, there is a trade-off relation between M/# and the rate of shrinkage, and when the addition amount of the photoreactive compound is increased for the purpose of making M/# large, the rate of shrinkage tends to increase. Accordingly, it may be said that a value obtained by dividing M/# by the rate of shrinkage is an index expressing good or bad of the performance.

In the light of the above, it may be said that what the value obtained by dividing M/# by the rate of shrinkage is large is excellent, whereas what the value obtained by dividing M/# by the rate of shrinkage is small is inferior.

The holographic recording medium of the present embodiment realizes a low rate of shrinkage while keeping high M/#, and in the case where the evaluation is performed on a medium having a recording layer thickness of 500 μm, a ratio of M/# to the rate of shrinkage of usually 100 or more, preferably 150 or more, and especially preferably 200 or more is attained.

While it may be said that a medium having a large capacity and a less error rate or noise has a high performance, in general, it may not be said definitely that the performance as a medium relies upon only the material. Thus, it becomes possible to efficiently develop a material by changing the wording into a performance as the material. It may be said that M/# and the rate of shrinkage are meaningful as indexes therefor.

IV. Polymerizable Reactive Compound According to the Invention

Of the polymerizable reactive compounds according to the invention, a compound represented by the following formula (2) is a novel compound.

[Formula 14]

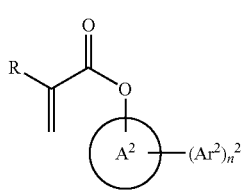

Formula (2)

(In the formula (2), $A^2$ is an optionally substituted ring selected from the group consisting of a benzene ring, a naphthalene ring and a dibenzothiophene group; $Ar^2$ is an optionally substituted, spiro carbon-free (hetero)aryl group formed by condensation of two or more rings; R is hydrogen or a methyl group; $n^2$ is an integer of from 1 to 7; and when $n^2$ is 2 or more, then plural $Ar^2$s may be the same as or different from each other.)

IV-2. Respective Components of Formula (2)

The reactive compound represented by the formula 2 is hereunder described in detail.

IV-1-1. $A^2$

In the formula (2), $A^2$ is an optionally substituted ring selected from the group consisting of a benzene ring, a naphthalene ring and a dibenzothiophene group. $A^2$ may further have a substituent in addition to $Ar^2$. The substituent which $A^2$ may have is not particularly limited so far as the compatibility is not lowered, or the refractive index is not decreased. Examples thereof include those described previously as specific example of the substituent which A in the formula (1) may have in addition to Ar.

IV-1-2. $Ar^2$

In the formula (2), $Ar^2$ is an optionally substituted, spiro carbon-free (hetero)aryl group formed by condensation of two or more rings. Specific examples thereof include those groups described previously as specific examples of Ar in the formula (1) but not containing spiro carbon. Preferred examples are also the same as those of Ar.

IV-1-3. $n^2$

In the formula (2), $n^2$ is an integer of from 1 to 7, and when $n^2$ is 2 or more, then plural $Ar^2$s may be the same as or different from each other. In order to obtain good solubility in a solvent or a matrix, $n^2$ is preferably from 1 to 5, more preferably from 1 to 3, and especially preferably 1 or 2.

The compound represented by the foregoing formula (2) is preferably represented by the following formula (2-1).

[Formula 15]

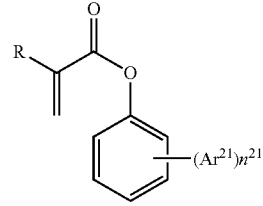

Formula (2-1)

(In the formula (2-1), $Ar^{21}$ is a heteroaryl group having a condensed polycyclic structure formed by bicondensation or tricondensation of a 6-membered ring and/or a 5-membered ring and having one or more heteroatoms in a skeleton of the condensed polycyclic structure, with the heteroatom being oxygen and/or sulfur; R is hydrogen or a methyl group; $n^{21}$ is an integer of from 1 to 5; and when $n^{21}$ is 2 or more, then plural $Ar^{21}$s may be the same as or different from each other. Incidentally, the benzene ring having $Ar^{21}$ may further have a substituent in addition to $Ar^{21}$.)

The reactive compound represented by the formula (2-1) is hereunder described in detail.

IV-2. Respective Components of Formula (2-1)

<$Ar^{21}$>

In the formula 1, $Ar^{21}$ is a heteroaryl group having a condensed polycyclic structure formed by bicondensation or tricondensation of a 6-membered ring and/or a 5-membered ring and having one or more heteroatoms in a skeleton of the condensed polycyclic structure, with the heteroatom being oxygen and/or sulfur. Though $Ar^{21}$ is not particularly limited so far as it is a heteroaryl group which satisfies the foregoing condition, from the reasons of solubility and coloration, the heteroatom number in the skeleton of the foregoing condensed polycyclic structure is preferably 1 or 2; and the heteroatom is preferably oxygen and/or sulfur from the viewpoint of refractive index. Also, with respect to a preferred substitution position of $Ar^{21}$, in the case where it is 1, any position is applicable, and in the case where it is 2 or more, from the reason that a synthesis yield is high, it is preferable that the positions are not adjacent to each other.

Specific examples of $Ar^{21}$ are given below, but it should not be construed that the invention is limited to thereto so far as the gist thereof is not deviated.

[Formula 16]

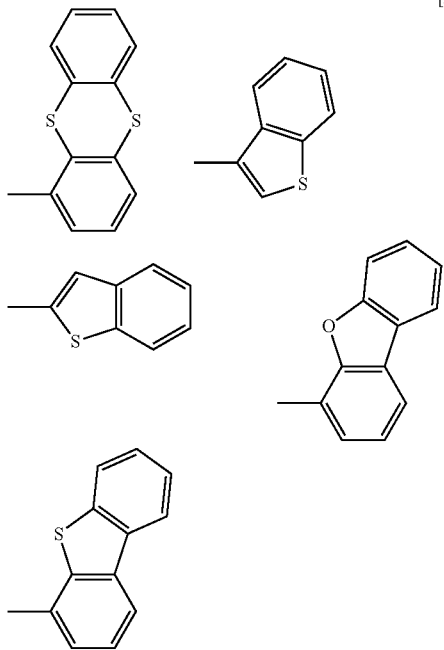

Besides, there are exemplified benzothioxane, benzothioxine, dibenzothioxine, benzodioxane, benzodioxine, benzodioxine and so forth.

Of these, from the standpoint of refractive index, thianthrene, dibenzothiophene and benzothiophene are preferable, and thianthrene and dibenzothiophene are more preferable.

<$n^{21}$>

In the formula (2-1), $n^{21}$ is an integer of from 1 to 7, and when n is 2 or more, then plural $Ar^{21}$s may be the same as or different from each other. In order to obtain good solubility in a solvent or a matrix, $n^{21}$ is preferably from 1 to 5, more preferably from 1 to 3, and especially preferably 1 or 2.

<Substituent which May be Contained in Addition to $Ar^{21}$>

The benzene ring having $Ar^{21}$ may further have a substituent in addition to $Ar^{21}$. For example, for the purpose of enhancing the solubility, an alkyl group, an alkoxy group, an alkoxyalkyl group, an alkoxycarbonyl group, an alkoxyalkoxy group or an alkanoyloxy group may be substituted thereon; and for the purpose of increasing the refractive index, an aryl group, an alkylthioalkyl group, an aryloxy group or an arylalkoxyl group may be substituted thereon. However, for the purpose of achieving economic synthesis, it is preferable that such a substituent is not contained.

Here, the alkyl group is preferably a chain alkyl group having from 1 to 4 carbon atoms, and specific examples thereof include a methyl group, an ethyl group, a propyl group, an isopropyl group, a butyl group, an isobutyl group, a sec-butyl group, etc.

The alkoxy group is preferably an alkoxy group having from 1 to 4 carbon atoms, and specific examples thereof include a methoxy group, an ethoxy group, etc.

The alkoxyalkyl group is preferably an alkoxyalkyl group having from 2 to 6 carbon atoms, and specific examples thereof include a methoxymethyl group, an ethoxymethyl group, a propoxymethyl group, a butoxymethyl group, a methoxyethyl group, an ethoxyethyl group, a propoxyethyl group, a butoxyethyl group, etc.

The alkoxycarbonyl group is preferably an alkoxycarbonyl group having from 2 to 5 carbon atoms, and specific examples thereof include a methoxycarbonyl group, an ethoxycarbonyl group, a propoxycarbonyl group, a butoxycarbonyl group, etc.

The alkoxyalkoxy group is preferably an alkoxyalkoxy group having from 3 to 6 carbon atoms, and specific examples thereof include a methoxyethoxy group, an ethoxyethoxy group, a propoxyethoxy group, a butoxyethoxy group, etc.

The alkanoyloxy group is preferably an alkanoyloxy group having from 2 to 5 carbon atoms, and specific examples thereof include an acetoxy group, a propionoxy group, a butyloxy group, a valeroxy group, etc.

The aryl group is preferably a monocyclic or condensed-ring aryl group having from 6 to 14 carbon atoms, and specific examples thereof include a phenyl group, a naphthyl group, an anthranyl group, etc.

The alkylthioalkyl group is preferably an alkylthioalkyl group having from 2 to 4 carbon atoms, and specific examples thereof include a methylthiomethyl group, a methylthioethyl group, an ethylthiomethyl group, an ethylthioethyl group, etc.

The aryloxy group is preferably a monocyclic or condensed-ring aryloxy group having from 6 to 14 carbon atoms, and specific examples thereof include a phenoxy group, etc.

The arylalkoxy group is preferably an arylalkoxy group having from 7 to 5 carbon atoms, and specific examples thereof include a benzyloxy group, etc.

Incidentally, a compound represented by the following formula (2-2) is more preferable as the compound represented by the formula (2-1).

[Formula 17]

Formula (2-2)

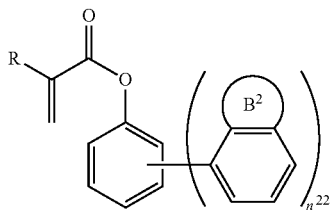

(In the formula (2-2), $B^2$ is a heteroaryl group which is a 6-membered and/or a 5-membered, monocyclic or bicyclic ring and which has one or more heteroatoms in a skeleton thereof, with the heteroatom being oxygen and/or sulfur; R is hydrogen or a methyl group; $n^{22}$ is an integer of from 1 to 5; and when $n^{22}$ is 2 or more, then plural $B^2$s may be the same as or different from each other. Incidentally, the compound represented by the formula (2-2) may further have a substituent in addition to the heteroaryl group containing the ring $B^2$.)

IV-3. Respective Components of Formula 2

<Ring $B^2$>

In the formula (2-2), the ring $B^2$ is a heteroaryl group which is a 6-membered and/or a 5-membered, monocyclic or bicyclic ring and which has one or more heteroatoms in a skeleton thereof, with the heteroatom being oxygen and/or sulfur. Though the ring $B^2$ is not particularly limited so far as it is a heteroaryl group which satisfies the foregoing condition, from the reasons of solubility and coloration, the heteroatom number in the skeleton of the foregoing condensed polycyclic structure is preferably 1 or 2; and the heteroatom is preferably oxygen and/or sulfur from the viewpoint of refractive index. Also, with respect to a preferred substitution position of the heteroaryl group containing the ring $B^2$, namely, the heteroaryl group having a condensed polycyclic structure which the ring $B^2$ forms together with the benzene ring, in the case where it is 1, any position is applicable, and in the case where it is 2 or more, from the reason that a synthesis yield is high, it is preferable that the positions are not adjacent to each other.

Examples of the heteroaryl group containing the ring $B^2$ include those corresponding to the structure of the formula (2-2) among the heteroaryl groups exemplified as Ar of the formula (1). However, it should not be construed that the invention is limited to thereto so far as the gist thereof is not deviated.

<$n^{22}$>

$n^{22}$ in the formula (2-2) is synonymous with n in the formula 1.

<Substituent which May be Contained in Addition to the Heteroaryl Group Containing the Ring $B^2$>

The compound represented by the formula (2-2) may further have a substituent in addition to the heteroaryl group containing the ring $B^2$. The "substituent which may be further contained in addition to the heteroaryl group containing the ring $B^2$" in the formula (2-2) is synonymous with the "substituent which may be further contained in addition to Ar".

IV-4. Molecular Weight and Water Solubility

From the standpoint of reduction of the rate of shrinkage following crosslinking at the time of light irradiation, a molecular weight of the above-described reactive compound represented by the formula (2), preferably the formula (2-1), and more preferably the formula (2-2) is usually not more than 1,500, preferably not more than 1,000, further preferably not more than 850, and especially preferably not more than 750. Above all, the molecular weight is not more than 600 and usually 300 or more, preferably 350 or more and especially preferably 400 or more.

Also, from the reason of enhancing the storage stability of a recording medium or the like, in general, it is preferable that the reactive compound represented by the formula (2) is insoluble in water. Here, the term "insoluble in water" means that a solubility in water under a condition at 25° C. and 1 atm. is usually not more than 0.1% by weight, and preferably not more than 0.01% by weight.

IV-5. Refractive Index

A refractive index or apparent refractive index at an irradiation light wavelength (recording wavelength or the like) of the reactive compound represented by the formula (2), preferably the formula (2-1), and more preferably the formula (2-2) is usually in the range of from 1.600 to 1.780, and preferably from 1.620 to 1.770. For example, in the case of using the reactive compound represented by the formula 1, and preferably the formula 2 as a holographic recording material, when the refractive index is smaller than 1.600, the diffraction efficiency is not large, and the multiplicity is not sufficient. Also, when the refractive index is larger than 1.780, a difference in the refractive index from the matrix resin becomes excessively large, so that scattering becomes large; and thus, the transmittance is lowered, thereby requiring larger energy during recording or reproduction.

Incidentally, when the refractive index is evaluated at a short wavelength, it exhibits a large value; however, a sample exhibiting a relatively large refractive index at a short wavelength also exhibits a relatively large refractive index even at a long wavelength, so that its relation is not reversed. In consequence, it is possible to evaluate a refractive index or apparent refractive index at a wavelength other than the recording wavelength, thereby predicting a refractive index at the recording wavelength.

Here, a value at the recording wavelength of 589 nm was made a basis.

In the case where the subject compound is a solid, the refractive index cannot be measured as it is. Thereafter, the apparent refractive index as referred to herein means a value obtained by, as described in Synthesis Example 1 as described later, dissolving the compound in an appropriate solvent to form a solution, measuring a refractive index of this solution and determining a refractive index in the case where the compound is 100% by means of extrapolation.

IV-6. Illustrative Compounds

Specific examples of the reactive compound represented by the formula (2), preferably the formula (2-1), and more preferably the formula (2-2) are given below, but it should not be construed that the invention is limited to thereto so far as the gist thereof is not deviated.

[Formula 18]

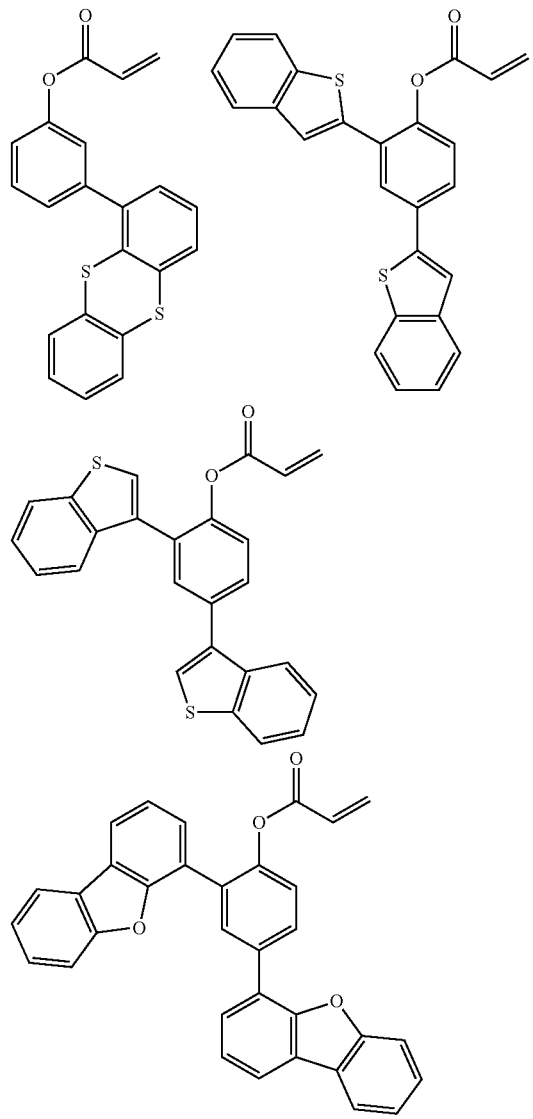

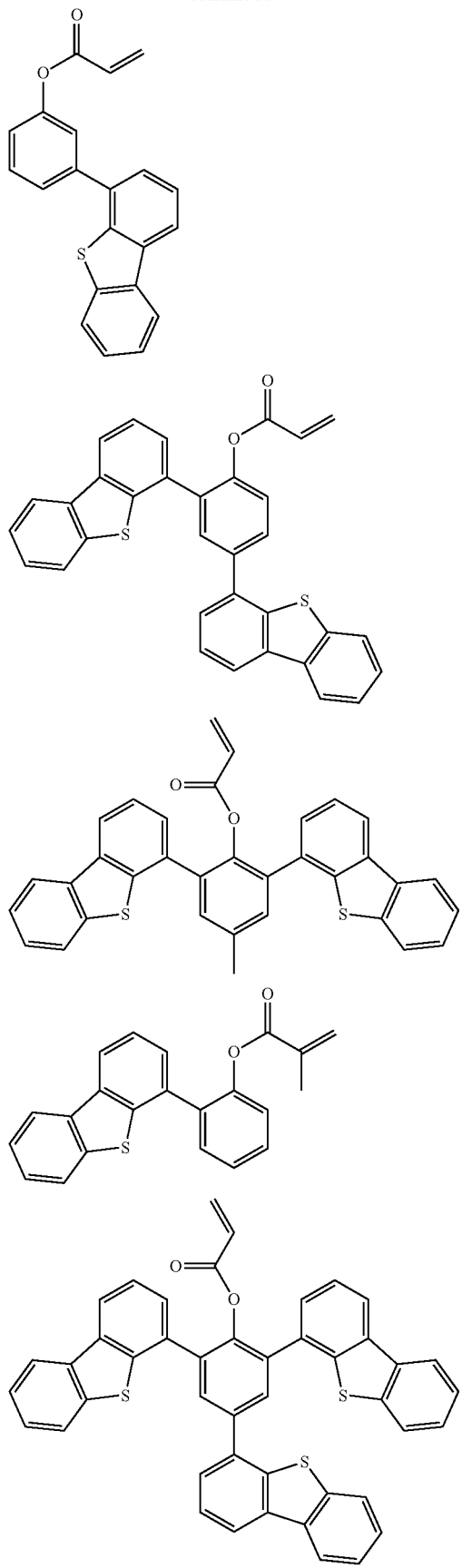
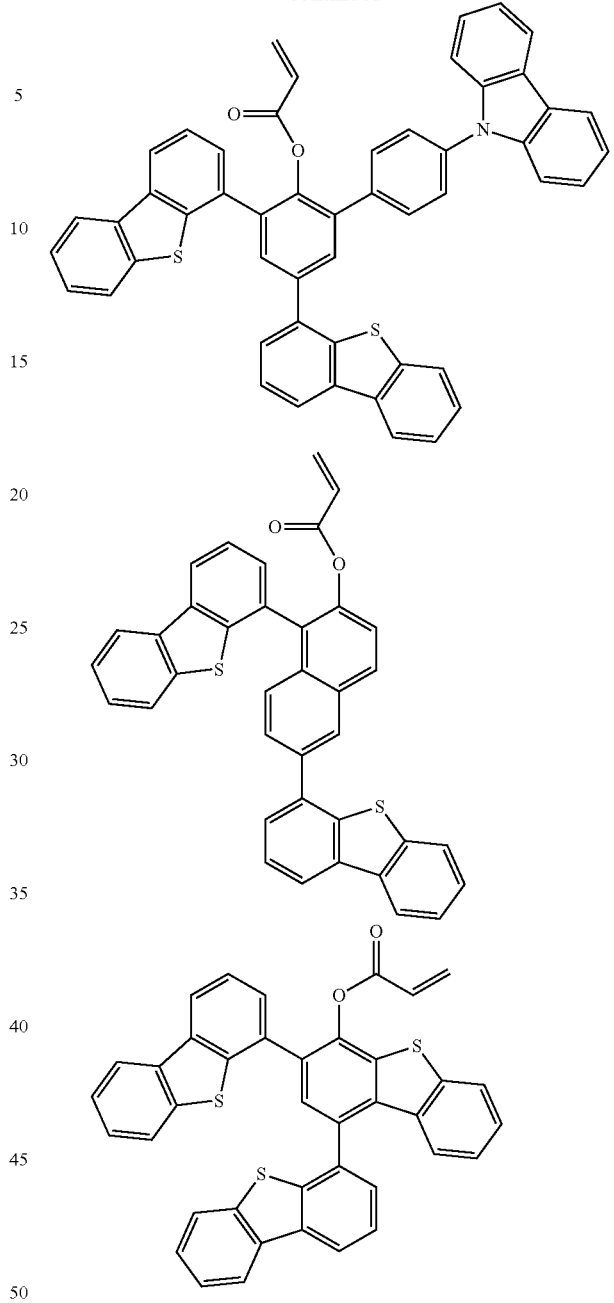

2-(1-thianthrenyl)-1-phenyl acrylate, 2-(2-benzothiophenyl)-1-phenyl acrylate, 2-(3-benzothiophenyl)-1-phenyl acrylate, 2-(4-dibenzofuranyl)-1-phenyl acrylate, 2-(4-dibenzothiophenyl)-1-phenyl acrylate, 3-(1-thianthenyl)-1-phenyl acrylate, 3-(2-benzothiophenyl)-1-phenyl acrylate, 3-(3-benzothiophenyl)-1-phenyl acrylate, 3-(4-dibenzofuranyl)-1-phenyl acrylate, 3-(4-dibenzothiophenyl)-1-phenyl acrylate, 4-(1-thiantherenyl)-1-phenyl acrylate, 4-(2-benzothiophenyl)-1-phenyl acrylate, 4-(3-benzothiophenyl)-1-phenyl acrylate, 4-(4-dibenzofuranyl)-1-phenyl acrylate, 4-(4-dibenzothiophenyl)-1-phenyl acrylate, 2,4-bis(1-thianthrenyl)-1-phenyl acrylate, 2,4-bis(2-benzothiophenyl)-1-phenyl acrylate, 2,4-bis(3-benzothiophenyl)-1-phenyl acrylate, 2,4-bis(4-dibenzofuranyl)-1-phenyl acrylate, 2,4-bis(4-dibenzothiophenyl)-1-phenyl acrylate, 4-methyl-2,6-bis(1-thiathrenyl)-1-phenyl acrylate, 4-methyl-2,6-bis(2- benzothiophenyl)-1-phenyl acrylate, 4-methyl-2,6-bis(3-benzothiophenyl)-1-phenyl acrylate, 4-methyl-2,6-bis(4-dibenzofuranyl)-1 phenyl acrylate, 4-methyl-2,6-bis(4-dibenzothiophenyl)-1-phenyl acrylate, 2-(1-thianthrenyl)-1-phenyl methacrylate, 2-(2-benzothiophenyl)-1-phenyl methacrylate, 2-(3-benzothiophenyl)-1-phenyl methacrylate, 2-(4-dibenzofuranyl)-1-phenyl methacrylate, 2-(4-dibenzothiophenyl)-1-phenyl methacrylate, 3-(1-thianthrenyl)-1-phenyl methacrylate, 3-(2-benzothiophenyl)-1-phenyl methacrylate, 3-(3-benzothiophenyl)-1-phenyl methacrylate, 3-(4-dibenzofuranyl)-1-phenyl methacrylate, 3-(4-dibenzothiophenyl)-1-phenyl methacrylate, 4-(1-thiantherenyl)-1-phenyl methacrylate, 4-(2-benzothiophenyl)-1-phenyl methacrylate, 4-(3-benzothiophenyl)-1-phenyl methacrylate, 4-(4-dibenzofuranyl)-1-phenyl methacrylate, 4-(4-dibenzothiophenyl)-1-phenyl methacrylate, 2,4-bis(1-thianthrenyl)-1-phenyl methacrylate, 2,4-bis(2-benzothiophenyl)-1-phenyl methacrylate, 2,4-bis(3-benzothiophenyl)-1-phenyl methacrylate, 2,4-bis(4-dibenzofuranyl)-1-phenyl methacrylate, 2,4-bis(4-dibenzothiophenyl)-1-phenyl methacrylate, 4-methyl-2,6-bis(1-thiathrenyl)-1-phenyl methacrylate, 4-methyl-2,6-bis(2-benzothiophenyl)-1-phenyl methacrylate, 4-methyl-2,6-bis(3-benzothiophenyl)-1-phenyl methacrylate, 4-methyl-2,6-bis(4-dibenzofuranyl)-1 phenyl methacrylate, 4-methyl-2,6-bis(4-dibenzothiophenyl)-1-phenyl methacrylate, and so forth.

IV-7. Synthesis Method

The compound represented by the formula (2), preferably the formula (2-1), and more preferably the formula (2-2) can be synthesized by a combination of various known methods.

That is, the compound is obtained by subjecting a compound ($a^2$) having a hydroxyl group at the (meth)acryloyl group-introducing position and X at each of the $Ar^2$ group-introducing positions having an n number on the ring $A^2$ and a borated $Ar^2$ compound ($b^2$) to an appropriate coupling reaction at a position to be introduced, thereby synthesizing a precursor ($c^2$). In the following scheme, X is a halogen atom, and though it is preferably bromine or iodine, it does not matter that X is chlorine.

Also, all of $A^2$, $Ar^2$ and $n^2$ are synonymous with those in the general formula (2).

[Formula 19]

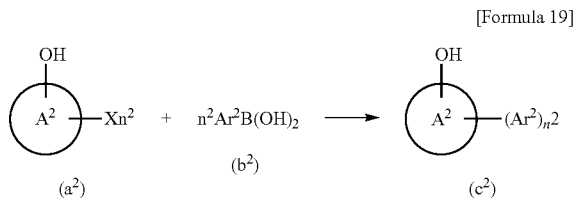

(1) The borated $Ar^2$ compound ($b^2$) can be synthesized by lithiating the $Ar^2$ compound with butyllithium and trapping the lithiated $Ar^2$ compound with a boric acid ester, followed by hydrolysis.

(2) The precursor ($c^2$) can be synthesized by dissolving the obtained borated $Ar^2$ compound ($b^2$) and the compound ($a^2$) having a hydroxyl group at the (meth)acryloyl group-introducing position and X at each of the $Ar^2$ group-introducing positions on the ring $A^2$ in an appropriate organic solvent and subjecting the solution to a coupling reaction with appropriate base and metal catalyst.

Incidentally, the foregoing compound ($a^2$) can be obtained by purchasing a commercially available product or by halogenating a hydroxyl group-containing compound. The halogenation is achieved by, for example, chlorine, bromine, iodine, N-bromosuccinic acid imide or iodine chloride. Further, the hydroxyl group-containing compound can be obtained from a corresponding halide, sulfate, nitrate or borate.

As the organic solvent, dimethoxyethane, tetrahydrofuran, methanol, ethanol, toluene, water or the like can be used singly or in combinations.

As the base, triethylamine, pyridine, sodium hydrogencarbonate, sodium carbonate, potassium carbonate or the like can be used singly or in combinations.

As the metal catalyst, palladium chloride, palladium acetate, tetrakis(triphenylphosphine)palladium or the like can be used.

For the purpose of improving solubility of the catalyst to reduce a use amount thereof, diazabicyclooctane which is a tertiary amine compound, tributylphosphine which is a tertiary phosphine compound, or 1-methylimidazole which is an imidazole compound may be used jointly.

Also, by again halogenating the foregoing precursor ($c^2$), an Ar-substituted compound corresponding to the compound ($a^2$) can be obtained, and hence, according to this, it is possible to obtain the precursor ($c^2$) having a different Ar. Similar to the foregoing, the halogenation is achieved by, for example, chlorine, bromine, iodine, N-bromosuccinic acid imide or iodine chloride.

By allowing acryloyl chloride (the case where R is hydrogen) or methacryloyl chloride (the case where R is a methyl group) to act on the thus obtained precursor ($c^2$) in the copresence of a base such as a tertiary amine, pyridine, an imidazole, etc., the compound represented by the formula (2) can be obtained.

V. Photoreactive Composition of the Invention

Though the photoreactive composition of the invention has the reactive compound represented by the foregoing formula (2), it may contain other polymerizable compound than the foregoing reactive compound.

The reactive compound, the photoreactive composition and the optical material using the same according to the invention are applicable to various optical products. They have excellent characteristics from the standpoints of high diffraction efficiency and low rate of shrinkage and can be suitably used for lens, optical recording, photofabrication, optical relief printing and so forth. Above all, they can be especially suitably used for applications of recording layer formation in the holographic recording medium as described previously in III and so forth.

A preferred embodiment of the case of using the photoreactive composition of the invention as a composition for forming a holographic recording layer is described previously in the section of I.

VI. Optical Material of the Invention

The optical material of the invention comprises the foregoing photoreactive composition of the invention.

The optical material of the invention is applicable to the foregoing various applications and is especially suitable for applications of recording layer formation in a holographic recording medium and so forth. A preferred embodiment in the case of using the optical material of the invention as a holographic recording material is described previously in the section of II.

Also, details of the case of applying each of the reactive compound, the photoreactive composition and the optical material using the same according to the invention as a holographic recording material to an application of recording layer formation in a holographic recording medium are described previously in the section of III.

EXAMPLES

Next, the invention is more specifically described with reference to the following Examples, but it should not be construed that the invention is limited to the following Examples so far as the gist thereof is not deviated. Incidentally, all "parts" in the following description are a "part by weight" unless otherwise indicated.

Synthesis Example 1

Synthesis of 3-(1-thianthrenyl)phenyl acrylate (i) Synthesis of 3-(1-thiathrenyl)phenol A four-necked flask is provided with a reflux condenser, a thermometer and a TEFLON (a registered trademark) bar including magnet therein; 2.5 g of 1-thianthreneboric acid, 0.31 g of tetrakis(triphenylphosphine)palladium and 1.65 g of 3-iodobenzene are placed therein; after adding 80 mL of dimethoxyethane, the mixture is stirred; 11 mL of 1M sodium bicarbonate water is further added thereto; and the flask is put in an oil bath at 80° C. and heated for 6 hours. After cooling to room temperature, the reaction mixture is concentrated by an evaporator until it is separated into two layers; and 50 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=70/30 (volume ratio)) to concentrate a component having an Rf of 0.42, thereby obtaining 1.95 g (yield: 84%) of the foregoing white solid. $^1$H NMR (CDCl$_3$, 400 MHz): δ (ppm) 5.6 (s, 1H), 7.20 to 7.51 (m, 11H)

(ii) Synthesis of 3-(1-thianthrenyl)phenyl acrylate 1.95 g of the thus obtained 3-(1-thiathrenyl)phenol is placed in a round bottom flask and dissolved in 10 mL of methylene chloride; after ice cooling the flask, 0.77 g of triethylamine is added; 0.68 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.50, thereby obtaining 1.5 g (yield: 66%) of the foregoing white solid. $^1$H NMR (CDCl$_3$, 400 MHz): δ (ppm) 6.00 (dd=1.2 & 10.4 Hz, 1H), 6.33 (dd= 10.4 & 17.2 Hz, 1H), 6.62 (dd=1.2 & 17.2 Hz, 1H), 7.20 to 7.51 (m, 11H)

Synthesis Example 2

Synthesis of 2,4-bis(2-benzothiophenyl)phenyl acrylate (i) Synthesis of 2,4-bis(2-benzothiophenyl)phenol Similar to Example 1-(i), 2.5 g of 2-benzothiopheneboric acid, 0.48 g of tetrakis(triphenylphosphine)palladium and 1.41 g of 2,4-dibromophenol are placed; after adding 70 mL of dimethoxyethane, the mixture is stirred; 16 mL of 1M sodium bicarbonate water is further added thereto; and the flask is put in an oil bath at 80° C. and heated for 4 hours. After cooling to room temperature, the reaction mixture is concentrated by an evaporator until it is separated into two layers; and 50 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.21, thereby obtaining 1.31 g (yield: 65%) of the foregoing white solid. $^1$H NMR (CDCl$_3$, 400 MHz): δ (ppm) 5.6 (s, 1H), 7.31 to 7.40 (m, 5H), 7.59 (s, 2H), 7.70 to 7.85 (m, 5H), 8.05 (d=2.4 Hz, 1H)

(ii) Synthesis of 2,4-bis(2-benzothiophenyl)phenyl acrylate 1.31 g of the thus obtained 2,4-bis(2-benzothiophenyl) phenol is placed in a round bottom flask; 20 mL of methylene chloride and 2 mL of tetrahydrofuran are added to form a transparent solution; after ice cooling the flask, 0.44 g of triethylamine is added; 0.39 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and gathered with the original methylene chloride solution; and the mixture is dried upon application of magnesium sulfate. The resulting mixture is concentrated by filtration with a filter paper; and the concentrate is separated by a silica gel column (eluate: hexane/ ethyl acetate=90/10 (volume ratio)) to concentrate a component having an Rf of 0.20, thereby obtaining 1.0 g (yield: 66%) of the foregoing white solid. $^1$H NMR (CDCl$_3$, 400 MHz): δ (ppm) 6.06 (dd=1.2 & 10.8 Hz, 1H), 6.38 (dd= 10.8 & 17.2 Hz, 1H), 6.64 (dd=1.2 & 17.2 Hz, 1H), 7.31 to 7.40 (m, 5H), 7.59 (s, 2H), 7.70 to 7.85 (m, 5H), 8.05 (d=2.4 Hz, 1H)

Synthesis Example 3

Synthesis of 2,4-bis(3-benzothiophenyl)phenyl acrylate (i) Synthesis of 2,4-bis(3-benzothiophenyl)phenol Similar to Example 1-(i), 2.5 g of 3-benzothiopheneboric acid, 0.48 g of tetrakis(triphenylphosphine)palladium and 1.41 g of 2,4-dibromophenol are placed; after adding 80 mL of dimethoxyethane, the mixture is stirred; 16 mL of 1M sodium bicarbonate water is further added thereto; and the flask is put in an oil bath at 80° C. and heated for 4 hours. After cooling to room temperature, the reaction mixture is concentrated by an evaporator until it is separated into two layers; and 50 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.25, thereby obtaining 1.96 g (yield: 97%) of the foregoing white solid. $^1$H NMR (CDCl$_3$, 400 MHz): δ (ppm) 5.6 (s, 1H), 7.38 to 7.47 (m, 7H), 7.65 to 7.75 (m, 3H), 7.88 to 7.96 (m, 3H)

(ii) Synthesis of 2,4-bis(3-benzothiophenyl)phenyl acrylate 1.96 g of the thus obtained 2,4-bis(3-benzothiophenyl)phenol is placed in a round bottom flask; 10 mL of methylene chloride is added to form a transparent solution; after ice cooling the flask, 0.66 g of triethylamine is added; 0.59 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=90/10 (volume ratio)) to concentrate a component having an Rf of 0.20, thereby obtaining 1.43 g (yield: 63%) of the foregoing white solid. $^1$H NMR (CDCl$_3$, 400 MHz): δ (ppm) 5.78 (dd=1.2 & 10.8 Hz, 1H), 6.01 (dd=10.8 & 17.2 Hz, 1H), 6.26 (dd=1.2 & 17.2 Hz, 1H), 7.38 to 7.47 (m, 7H), 7.65 to 7.75 (m, 3H), 7.88 to 7.96 (m, 3H)

Synthesis Example 4

Synthesis of 2,4-bis(4-dibenzofuranyl)phenyl acrylate (i) Synthesis of 2,4-bis(4-dibenzofurany)phenol Similar to Example 1-(i), 3.0 g of 4-benzofuranboric acid, 0.46 g of tetrakis(triphenylphosphine)palladium and 1.69 g of 2,4-dibromophenol are placed; after adding 80 mL of dimethoxyethane, the mixture is stirred; 16 mL of 1M sodium bicarbonate water is further added thereto; and the flask is put in an oil bath at 80° C. and heated for 3 hours. After cooling to room temperature, the reaction mixture is concentrated by an evaporator until it is separated into two layers; and 50 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.20, thereby obtaining 1.89 g (yield: 66%) of the foregoing white solid. $^1$H NMR (CDCl$_3$, 400 MHz): δ (ppm) 5.6 (s, 1H), 7.34 to 7.38 (m, 2H), 7.41 to 7.46 (m, 4H), 7.51 to 7.61 (m, 4H), 7.66 to 7.68 (m, 1H), 7.95 to 7.98 (m, 4H), 7.99 to 8.00 (m, 1H), 8.05 to 8.06 (m, 1H)

(ii) Synthesis of 2,4-bis(4-dibenzofuranyl)phenyl acrylate 1.89 g of the thus obtained 2,4-bis(4-dibenzofuranyl)phenol is placed in a round bottom flask; 20 mL of methylene chloride is added to form a transparent solution; after ice cooling the flask, 0.54 g of triethylamine is added; 0.48 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=90/10 (volume ratio)) to concentrate a component having an Rf of 0.20, thereby obtaining 1.69 g (yield: 79%) of the foregoing white solid. $^1$H NMR (CDCl$_3$, 400 MHz): δ (ppm) 5.66 (dd=1.2 & 10.8 Hz, 1H), 5.98 (dd=10.8 & 17.2 Hz, 1H), 6.28 (dd=1.2 & 17.2 Hz, 1H), 7.34 to 7.38 (m, 2H), 7.41 to 7.46 (m, 4H), 7.51 to 7.61 (m, 4H), 7.66 to 7.68 (m, 1H), 7.95 to 7.98 (m, 4H), 7.99 to 8.00 (m, 1H), 8.05 to 8.06 (m, 1H)

Synthesis Example 5

Synthesis of 3-(4-dibenzothiophenyl)phenyl acrylate (i) Synthesis of 3-(4-dibenzothiophenyl)phenol Similar to Example 1-(i), 1.5 g of 4-dibenzothiopheneboric acid, 0.22 g of tetrakis(triphenylphosphine)palladium and 1.21 g of 3-iodobenzene are placed; after adding 50 mL of dimethoxyethane, the mixture is stirred; 7.5 mL of 1M sodium bicarbonate water is further added thereto; and the flask is put in an oil bath at 80° C. and heated for 6 hours. After cooling to room temperature, the reaction mixture is concentrated by an evaporator until it is separated into two layers; and 30 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=70/30 (volume ratio)) to concentrate a component having an Rf of 0.40, thereby obtaining 1.03 g (yield: 68%) of the foregoing white solid. $^1$H NMR (CDCl$_3$, 400 MHz): δ (ppm) 5.6 (s, 1H), 7.20 to 7.24 (m, 1H), 7.44 to 7.55 (m, 6H), 7.62 to 7.65 (m, 1H), 7.82 to 7.85 (m, 1H), 8.14 to 8.19 (m, 2H)

(ii) Synthesis of 3-(4-dibenzothiophenyl)phenyl acrylate 1.03 g of the thus obtained 3-(4-dibenzothiophenyl)phenol is placed in a round bottom flask and suspended in 15 mL of methylene chloride; after ice cooling the flask, 0.45 g of triethylamine is added; 0.40 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and ethyl acetate, respectively and then gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.50, thereby obtaining 0.90 g (yield: 73%) of the foregoing white solid. $^1$H NMR (CDCl$_3$, 400 MHz): δ (ppm) 6.03 (dd=1.2 & 10.4 Hz, 1H), 6.36 (dd=10.4 & 17.2 Hz, 1H), 6.64 (dd=

1.2 & 17.2 Hz, 1H), 7.20 to 7.24 (m, 1H), 7.44 to 7.55 (m, 6H), 7.62 to 7.65 (m, 1H), 7.82 to 7.85 (m, 1H), 8.14 to 8.19 (m, 2H)

Synthesis Example 6

Synthesis of 2,4-bis(4-dibenzothiophenyl)phenyl acrylate (i) Synthesis of 2,4-bis(4-dibenzothiophenyl)phenol Similar to Example 1-(i), 3.0 g of 4-dibenzothiopheneboric acid, 0.41 g of tetrakis(triphenylphosphine)palladium and 1.58 g of 2,4-dibromophenol are placed; after adding 40 mL of dimethoxyethane, the mixture is stirred; 15 mL of 1M sodium bicarbonate water is further added thereto; and the flask is put in an oil bath at 80° C. and heated for 3 hours. After cooling to room temperature, the reaction mixture is concentrated by an evaporator until it is separated into two layers; and 50 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.27, thereby obtaining 1.02 g (yield: 35%) of the foregoing white solid. $^1$H NMR (CDCl$_3$, 400 MHz): δ (ppm) 5.6 (s, 1H), 7.16 to 8.25 (m, 17H)

(ii) Synthesis of 2,4-bis(4-dibenzothiophenyl)phenyl acrylate 1.02 g of the thus obtained 2,4-bis(4-dibenzothiophenyl) phenol is placed in a round bottom flask; 5 mL of methylene chloride is added to form a transparent solution; after ice cooling the flask, 0.27 g of triethylamine is added; 0.24 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and then gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.42, thereby obtaining 1.0 g (yield: 88%) of the foregoing white solid. $^1$H NMR (CDCl$_3$, 400 MHz): δ (ppm) 6.05 (dd=1.2 & 10.4 Hz, 1H), 6.37 (dd=10.4 & 17.2 Hz, 1H), 6.66 (dd=1.2 & 17.2 Hz, 1H), 7.30 to 8.25 (m, 17H)

Synthesis Example 7

Synthesis of 2,6-bis(4-dibenzothiophenyl)-4-methylphenyl acrylate (i) Synthesis of 2,6-bis(4-dibenzothiophenyl)-4-methylphenol Similar to Example 1-(i), 2.5 g of 4-dibenzothiopheneboric acid, 0.38 g of tetrakis(triphenylphosphine)palladium and 1.16 g of 2,6-dibromo-4-methylphenol are placed; after adding 70 mL of dimethoxyethane and 10 mL of tetrahydrofuran, the mixture is stirred in a heterogeneous state; 12.4 mL of 1M sodium bicarbonate water is further added thereto; and the flask is put in an oil bath at 80° C. and heated for 8 hours. Following heating, the solution increases a feeling of transparency step by step. After cooling to room temperature, the reaction mixture is concentrated by an evaporator until it is separated into two layers; and 50 mL of methylene chloride is added, followed by separation from an aqueous layer. The aqueous layer is washed with methylene chloride and gathered with the preceding methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.27, thereby obtaining 1.35 g (yield: 60%) of the foregoing white solid. $^1$H NMR (CDCl$_3$, 400 MHz): δ (ppm) 2.43 (s, 3H), 5.05 (s, 1H), 7.38 (s, 2H), 7.43 to 7.50 (m, 4H), 7.55 to 7.60 (m, 4H), 7.80 (m, 2H), 8.20 (m, 4H)

(ii) Synthesis of 2,6-bis(4-dibenzothiophenyl)-4-methylphenyl acrylate 1.35 g of the thus obtained 2,6-bis(4-dibenzothiophenyl)-4-methylphenol is placed in a round bottom flask; 20 mL of methylene chloride is added; after ice cooling the flask, 0.33 g of triethylamine is added; 0.30 g of acryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and then gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=80/20 (volume ratio)) to concentrate a component having an Rf of 0.42, thereby obtaining 0.85 g (yield: 57%) of the foregoing white solid. $^1$H NMR (CDCl$_3$, 400 MHz): δ (ppm) 2.57 (s, 3H), 5.41 (dd=1.2 & 10.4 Hz, 1H), 5.64 (dd=10.4 & 17.2 Hz, 1H), 5.97 (dd=1.2 & 17.2 Hz, 1H), 7.49 to 7.59 (m, 10H), 7.90 (m, 2H), 8.16 to 8.21 (m, 4H)

Synthesis Example 8

Synthesis of 2-(4-dibenzothiophenyl)phenyl methacrylate 0.65 g of 3-(4-dibenzothiophenyl)phenol obtained in Synthesis Example 5-(i) is placed and dissolved in 20 mL of methylene chloride; after ice cooling the flask, 0.28 g of triethylamine is added; 0.29 g of methacryloyl chloride is then added dropwise; after adding the whole, the temperature is returned to room temperature; and the mixture is stirred for 30 minutes. 10 mL of water is added; the mixture is vigorously stirred; an aqueous layer is then removed; the aqueous layer is washed with methylene chloride and then gathered with the original methylene chloride solution; and the mixture is dried upon application of magnesium sulfate. The resulting mixture is concentrated by filtration with a filter paper; and the concentrate is separated by a silica gel column (eluate: hexane/ethyl acetate=80/10 (volume ratio)) to concentrate a component having an Rf of 0.50, thereby obtaining 0.63 g (yield: 78%) of the foregoing white solid. $^1$H NMR (CDCl$_3$, 400 MHz): δ (ppm) 2.09 (s, 3H), 5.77 (dd=1.6 Hz, 1H), 6.39 (s, 1H), 7.21 (m, 1H), 7.45 to 7.55 (m, 6H), 7.62 to 7.64 (m, 1H), 7.82 to 7.85 (m, 1H), 8.14 to 8.19 (m, 2H)

Synthesis Example 9

Synthesis of 2,4,6-tris(4-dibenzothiophenyl)phenyl acrylate (i) Synthesis of 2,4,6-tris(4-dibenzothiophenyl)phenol Similar to Example 1-(i), 4.2 g of 4-dibenzothiopheneboric acid, 1.5 g of 2,4,6-tribromophenol and 0.33 g of tetrakis(triphenylphosphine)palladium are placed; after adding 30 mL of toluene and 30 mL of ethanol, the mixture is stirred; 20 mL of a 1M sodium carbonate aqueous solution is further added thereto; and the flask is put in an oil bath at 60° C. and heated for 5 hours. After cooling to room temperature, 50 mL of THF is added; the mixture is thoroughly stirred; an insoluble matter is removed by filtration; and the filtrate is separated from an aqueous phase. An organic phase is washed with saturated salt water and then dried upon application of magnesium sulfate. The magnesium sulfate is removed by filtration; the residue is concentrated by an evaporator; and 200 mL of dichloromethane is added to the obtained deeply brown oily residue to form a suspension. A pale brown oily solid is obtained by filtration and further washed with 100 mL of ethanol, followed by drying to obtain 1.9 g (yield: 66%) of the foregoing pale brown solid.

(ii) Synthesis of 2,4,6-tris(4-dibenzothiophenyl)phenyl acrylate 1.5 g of the thus obtained 2,4,6-tris(4-dibenzothiophenyl)phenol is placed in a round bottom flask; 30 mL of THF is added to form a transparent solution; after ice cooling the flask, 0.4 g of triethylamine is added; 0.30 g of acryloyl chloride is then added dropwise; after adding the whole, the temperature is returned to room temperature; and the mixture is stirred for 30 minutes. 30 mL of water is added; the mixture is vigorously stirred; and 100 mL of dichloromethane is then added, thereby separating an aqueous solution. The aqueous layer is washed with dichloromethane and then gathered with the original dichloromethane solution; and the mixture is dried upon application of magnesium sulfate. The resulting mixture is concentrated by filtration with a filter paper; and the concentrate is separated by a silica gel column (eluate: hexane/dichloromethane mixture), thereby obtaining 0.9 g (yield: 59%) of the foregoing white solid. $^1$H NMR (CDCl$_3$, 400 MHz): δ (ppm) 5.44 (dd=1.2 & 10.4 Hz, 1H), 5.63 (dd=10.4 & 17.2 Hz, 1H), 5.96 (dd=1.2 & 17.2 Hz, 1H), 7.43 to 7.69 (m, 12H), 7.82 to 7.91 (m, 3H), 8.12 (s, 2H), 8.14 to 8.21 (m, 6H)

Synthesis Example 10

Synthesis of 2,4-bis(4-dibenzothiophenyl)-6-[4-(N-carbazole)phenyl]phenyl acrylate (i) Synthesis of 2,4-bis(4-dibenzothiophenyl)-6-bromophenol 3.8 g of 2,4-bis(4-dibenzothiophenyl)phenol obtained in Synthesis Example 6-(i) is placed in a round bottom flask; 24 mL of DMF is added to form a transparent solution; after ice cooling the flask, a solution of 1.5 g of N-succinic acid imide dissolved in 7 mL of DMF is added dropwise; and after adding the whole, the mixture is stirred under ice cooling for 2 hours. The reaction solution is thrown into 300 mL of water to form a suspension; the suspension is subjected to separation by filtration; and a pale purple solid is washed with 10 mL of cooled dichloromethane, followed by drying to obtain 3.2 g (yield: 71%) of the foregoing pale purple solid. $^1$H NMR (CDCl$_3$, 400 MHz): δ (ppm) 5.75 (s, 1H), 7.44 to 7.63 (m, 8H), 7.82 to 7.87 (m, 3H), 8.00 (d=2.4 Hz, 1H), 8.13 to 8.24 (m, 4H)

(ii) Synthesis of 2,4-bis(4-dibenzothiophenyl)-6-[4-(N-carbazole)phenyl]phenol

Similar to Synthesis Example 1-(i), 1.5 g of 4-(N-carbazole)phenylboric acid, 1.8 g of the thus obtained 2,4-bis(4-dibenzothiophenyl)-6-bromophenol and 0.2 g of tetrakis(triphenylphosphine)palladium are placed; after adding 40 mL of toluene and 30 mL of ethanol, the mixture is stirred; 5.4 mL of a 1M sodium carbonate aqueous solution is further added thereto; and the flask is put in an oil bath at 80° C. and heated for 6 hours. After cooling to room temperature, an insoluble matter is removed by filtration, and the insoluble solid is thoroughly washed with THF. The filtrate and the washing liquid are gathered, and 30 mL of ethyl acetate and 30 mL of saturated salt water are added, thereby separating an aqueous phase. An organic layer is washed with saturated salt water and then dried upon application of magnesium sulfate. The magnesium sulfate is removed by filtration; the residue is concentrated by an evaporator; and a major product is separated by a silica gel column (eluate: hexane/dichloromethane mixture), thereby obtaining 1.7 g (yield: 73%) of the foregoing white solid. $^1$H NMR (CDCl$_3$, 400 MHz): δ (ppm) 5.53 (s, 1H), 7.27 to 7.32 (m, 2H), 7.40 to 7.73 (m, 14H), 7.84 to 7.90 (m, 3H), 7.97 to 8.02 (m, 2H), 8.14 to 8.30 (m, 6H)

(iii) Synthesis of 2,4-bis(4-dibenzothiophenyl)-6-[4-(N-carbazole)phenyl]phenyl acrylate 1.7 g of the thus obtained 2,4-bis(4-dibenzothiophenyl)-6-[4-(N-carbazole)phenyl]phenol is placed in a round bottom flask; 30 mL of THF is added to form a transparent solution; after ice cooling the flask, 0.4 g of triethylamine is added; 0.32 g of acryloyl chloride is then added dropwise; after adding the whole, the temperature is returned to room temperature; and the mixture is stirred for 30 minutes. 15 mL of water is added; the mixture is vigorously stirred; and 30 mL of ethyl acetate and 15 mL of saturated salt water are then added, thereby separating an aqueous solution. An organic phase is washed with saturated salt water and dried upon application of magnesium sulfate. The resulting mixture is concentrated by filtration with a filter paper; and the concentrate is separated by a silica gel column (eluate: hexane/dichloromethane mixture), thereby obtaining 1.6 g (yield: 90%) of the foregoing white solid. $^1$H NMR (CDCl$_3$, 400 MHz): δ (ppm) 5.67 (dd=1.2 & 10.4 Hz, 1H), 5.89 (dd=10.4 & 17.2 Hz, 1H), 6.20 (dd=1.2 & 17.2 Hz, 1H), 7.26 to 7.32 (m, 2H), 7.38 to 7.69 (m, 14H), 7.83 to 7.89 (m, 4H), 8.04 to 8.22 (m, 8H)

Synthesis Example 11

Synthesis of 2,4-bis(4-dibenzothiophenyl)-6-btomophenyl acrylate 1.0 g of 2,4-bis(4-dibenzothiophenyl)-6-bromophenol obtained in Synthesis Example 10-(i) is placed in a round bottom flask; 20 mL of THF is added to form a transparent solution; after ice cooling the flask, 0.29 g of triethylamine is added; 0.22 g of acryloyl chloride is then added dropwise; after adding the whole, the temperature is returned to room temperature; and the mixture is stirred for 30 minutes. 10 mL of water is added; the mixture is vigorously stirred; and 30 mL of ethyl acetate and 15 mL of saturated salt water are then added, thereby separating an aqueous solution. An organic phase is washed with saturated salt water and dried upon application of magnesium sulfate. The resulting mixture is concentrated by filtration with a filter paper; and the concentrate is separated by a silica gel column (eluate: hexane/dichloromethane mixture), thereby obtaining 1.0 g (yield: 91%) of the foregoing white solid. $^1$H NMR (CDCl$_3$, 400 MHz): δ (ppm) 5.82 (dd=1.2 & 10.4 Hz, 1H), 6.05 (dd= 10.4 & 17.2 Hz, 1H), 6.39 (dd=1.2 & 17.2 Hz, 1H), 7.44 to 7.53 (m, 6H), 7.55 to 7.60 (m, 2H), 7.81 to 7.87 (m, 2H), 7.96 (d=2.0 Hz, 1H), 8.12 (d=2.0 Hz, 1H), 8.14 to 8.21 (m, 4H)

Synthesis Example 12

Synthesis of 1,6-bis(4-dibenzothiophenyl)-2-naphthyl acrylate (i) Synthesis of 1,6-bis(4-dibenzothiophenyl)-2-naphthol Similar to Synthesis Example 1-(i), 3.4 g of 4-dibenzothiopheneboric acid, 1.5 g of 1,6-dibromo-2-naphthol and 0.35 g of tetrakis(triphenylphosphine)palladium are placed; after adding 30 mL of toluene and 30 mL of ethanol, the mixture is stirred; 17 mL of a 1M sodium carbonate aqueous solution is further added thereto; and the flask is put in an oil bath at 50° C. and heated for 3 hours. After cooling to room temperature, 50 mL of THF is added; the mixture is thoroughly stirred; an insoluble matter is removed by filtration; and 30 mL of ethyl acetate and 15 mL of saturated salt water are added to the filtrate, thereby separating an aqueous phase. An organic layer is washed with saturated salt water and then dried upon application of magnesium sulfate. The magnesium sulfate is removed by filtration; the residue is concentrated by an evaporator; and a major product is separated by a silica gel column (eluate: hexane/dichloromethane mixture), thereby obtaining 1.8 g (yield: 70%) of the foregoing white solid. $^1$H NMR (CDCl$_3$, 400 MHz): δ (ppm) 5.11 (s, 1H), 7.38 to 7.53 (m, 6H), 7.55 to 7.60 (m, 3H), 7.66 to 7.84 (m, 4H), 8.00 (d=8.8 Hz, 1H), 8.14 to 8.22 (m, 2H), 8.24 to 8.28 (m, 2H), 8.34 (dd=1.2 & 8.0 Hz, 1H)

(ii) Synthesis of 1,6-bis(4-dibenzothiophenyl)-2-naphthyl acrylate 1.8 g of the thus obtained 1,6-bis(4-dibenzothiophenyl)-2-naphthol is placed in a round bottom flask; 30 mL of THF is added to form a transparent solution; after ice cooling the flask, 0.58 g of triethylamine is added; 0.48 g of acryloyl chloride is then added dropwise; after adding the whole, the temperature is returned to room temperature; and the mixture is stirred for 30 minutes. 15 mL of water is added; the mixture is vigorously stirred; and 30 mL of ethyl acetate and 15 mL of saturated salt water are then added, thereby separating an aqueous solution. An organic phase is washed with saturated salt water and dried upon application of magnesium sulfate. The resulting mixture is concentrated by filtration with a filter paper; and a major product is separated by a silica gel column (eluate: hexane/dichloromethane mixture), thereby obtaining 1.8 g (yield: 90%) of the foregoing white solid. $^1$H NMR (CDCl$_3$, 400 MHz): δ (ppm) 5.66 (dd=1.2 & 10.4 Hz, 1H), 5.94 (dd=10.4 & 17.2 Hz, 1H), 6.18 (dd=1.2 & 17.2 Hz, 1H), 7.37 to 7.60 (m, 10H), 7.67 to 7.74 (m, 2H), 7.77 to 7.82 (m, 1H), 8.07 (d=8.8 Hz, 1H), 8.10 to 8.24 (m, 4H), 8.15 (d=1.6 Hz, 1H)

Synthesis Example 13

Synthesis of 1,3-bis(4-dibenzothiophenyl)-4-dibenzothiophenyl acrylate (i) Synthesis of 4-hydroxydibenzothiophene 4.0 g of 4-dibenzothiopheneboric acid is placed in a round bottom flask; after adding 80 mL of ethanol and 20 mL of water, the mixture is stirred; 2.2 mL of a 30% hydrogen peroxide aqueous solution is further added thereto; and the flask is put in an oil bath at 60° C. and heated for 1 hour. After cooling to room temperature, the reaction mixture is concentrated by an evaporator; 100 mL of water is added to the residue; and the mixture is stirred to form a suspension. The suspension is subjected to separation by filtration, and after drying, 2.4 g (yield: 66%) of the foregoing solid is obtained. $^1$H NMR (DMSOd-6, 400 MHz): δ (ppm) 6.95 (dd=0.8 & 8 Hz, 1H), 7.34 (t=8 Hz, 1H), 7.46 to 7.53 (m, 2H), 7.81 (dd=0.8 & 8 Hz, 1H), 7.98 to 8.04 (m, 1H), 8.25 to 8.31 (m, 1H), 10.43 (s, 1H)

(ii) Synthesis of 1,3-dibromo-4-hydroxydibenzothiophene 2.4 g of the thus obtained 4-hydroxydibenzothiophene is placed in a round bottom flask; 27 mL of DMF is added to form a transparent solution; after ice cooling the flask, a solution of 4.4 g of N-succinic acid imide dissolved in 20 mL of DMF is added dropwise; and after adding the whole, the mixture is stirred under ice cooling for 2 hours. The reaction solution is thrown into 350 mL of water to form a suspension; the suspension is subjected to separation by filtration; and a brown solid is suspended and washed with 100 mL of cooled dichloromethane, followed by drying to obtain 1.3 g (yield: 31%) of the foregoing brown solid. $^1$H NMR (CDCl$_3$, 400 MHz): δ (ppm) 5.75 to 6.20 (br, 1H), 7.48 to 7.57 (m, 2H), 7.74 (s, 1H), 7.86 to 7.89 (m, 1H), 9.11 to 9.14 (m, 1H)

(iii) Synthesis of 1,3-bis(4-dibenzothiophenyl)-4-hydroxydibenzothiophene

Similar to Example 1-(i), 2.1 g of 4-dibenzothiopheneboric acid, 1.3 g of thus obtained 1,3-dibromo-4-hydroxydibenzothiophene and 0.26 g of tetrakis(triphenylphosphine)palladium are placed; after adding 25 mL of toluene and 25 mL of ethanol, the mixture is stirred; 10 mL of a 1M sodium carbonate aqueous solution is further added thereto; and the flask is put in an oil bath at 60° C. and heated for 5 hours. After cooling to room temperature, an insoluble matter is removed by filtration, and the solid is thoroughly washed with ethyl acetate. 30 mL of ethyl acetate and 15 mL of saturated salt water are added to a solution obtained by combining the filtrate and the washing liquid, thereby separating an aqueous phase. An organic phase is washed with saturated salt water and then dried upon application of magnesium sulfate. The magnesium sulfate is removed by filtration; the residue is concentrated by an evaporator; and a major product is separated by a silica gel column (eluate: hexane/dichloromethane mixture), thereby obtaining 1.6 g (yield: 76%) of the foregoing white solid. $^1$H NMR (CDCl$_3$, 400 MHz): δ (ppm) 5.76 (s, 1H), 6.90 to 6.99 (m, 2H), 7.30 to 7.35 (m, 1H), 7.40 to 7.51 (m, 4H), 7.57 to 7.61 (m, 5H), 7.41 (d=8 Hz, 1H), 7.81 to 7.85 (m, 1H), 7.80 (d=8 Hz, 1H), 8.18 to 8.26 (m, 3H), 8.29 (dd=1.2 & 7.6 Hz, 1H)

(iv) Synthesis of 1,3-bis(4-dibenzothiophenyl)-4-dibenzothiophenyl acrylate 1.6 g of the thus obtained 1,3-bis(4-dibenzothiophenyl)-4-hydroxydibenzothiophene is placed in a round bottom flask; 35 mL of THF is added to form a transparent solution; after ice cooling the flask, 0.47 g of triethylamine is added; 0.38 g of acryloyl chloride is then added dropwise; after adding the whole, the temperature is returned to room temperature; and the mixture is stirred for 30 minutes. 15 mL of water is added; the mixture is vigorously stirred; and 30 mL of ethyl acetate and 15 mL of saturated salt water are then added, thereby separating an aqueous solution. An organic phase is washed with saturated salt water and dried upon application of magnesium sulfate. The resulting mixture is concentrated by filtration with a filter paper; and a major product is separated by a silica gel column (eluate: hexane/dichloromethane mixture), thereby obtaining the foregoing brown solid. This is washed with a mixed solvent of 20 mL of dichloromethane and 60 mL of hexane and then dried to obtain 1.1 g (yield: 63%) of the foregoing pale brown solid. $^1$H NMR (CDCl$_3$, 400 MHz): δ (ppm) 5.90 (dd=1.2 & 10.4 Hz, 1H), 6.16 (dd=10.4 & 17.2 Hz, 1H), 6.47 (dd=1.2 & 17.2 Hz, 1H), 6.89 (d=7.6 Hz, 1H), 6.98 (dt=1.2 & 7.6 Hz, 1H), 7.30 to 7.35 (m, 1H), 7.40 to 7.58 (m, 6H), 7.62 to 7.68 (m, 2H), 7.73 to 7.84 (m, 4H), 8.12 to 8.18 (m, 2H), 8.25 (dd=0.8 & 7.6 Hz, 1H), 8.31 (dd=1.2 & 7.6 Hz, 1H)

Examples 1 to 8

Apparent Refractive Index of Compound

With respect to each of the compounds obtained in Synthesis Examples 3, 6, 7, 8, 9, 10, 11 and 12, an apparent refractive index was determined according to the following procedures.

In view of the fact that each of the obtained compounds is a solid, it is impossible to measure a refractive index in a state as it stands. Also, when a temperature is applied, polymerization occurs in a part thereof to cause liquefaction, so that the refractive index cannot be measured. Then, the compound was dissolved in an appropriate solvent, and extrapolation was performed from a relation of a refractive index of the solution vs. a volume ratio of the present compound, thereby defining an apparent refractive index of the present compound. For the measurement, an Abbe refractometer DR-M2, manufactured by Atago Co., Ltd. was used, and the temperature was controlled at 25° C. at a wavelength of 589 nm. In this way, in the case of a substrate which is solid and rich in reactivity, it is difficult to measure its refractive index; and therefore, a volume fraction obtained through calculation by measuring a specific gravity of a solution obtained by dissolving the compound in a solvent and a refractive index of the subject solution are measured using the foregoing apparatus, followed by extrapolation into 100% of a substrate to define the refractive index. In that case, 1-bromonaphthalene was used as the solvent, and a substrate concentration was regulated to 20% by weight.

Though this method does not apply unless a total sum of a volume of the solvent and a volume of the substrate conforms with a volume of the solution, the calculation was made on the assumption that the foregoing relation applies through use of a solution in which a concentration of a solute was made low as not more than 20% by weight.

Example 9

Figure 2:
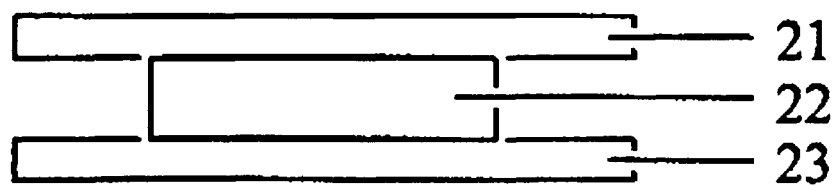
FIG. 2 is a schematic view showing a configuration of a medium for measurement fabricated in the Examples.

A solution A obtained by dissolving 0.216 g of 3-(1-thianthrenyl)phenyl acrylate obtained in Synthesis Example 1 and 0.022 g of TPO (2,4,6-trimethylbenzoyldiphenylphosphine oxide, manufactured by Ciba Specialty Chemicals) in 1.950 g of hexamethylene diisocyanate, followed by deaeration and a solution B obtained by mixing and dissolving 4.545 g of T5650J (polycarbonate diol having an average molecular weight of 760, manufactured by Asahi Kasei Chemicals Corporation), 0.505 g of trimethylolpropane and 0.0014 g of dioctyltin dilaurate, followed by deaeration were prepared; and the both solutions were added and well stirred, followed by deaeration. The preceding deaerated liquid was cast on a slide glass in which a 500 μm-thick TEFLON (a registered trademark) sheet was placed as a spacer on both ends thereof; a slide glass was further covered thereon; the periphery was fixed by a grip; and the assembly was heated at 60° C. for 15 hours to prepare a recording layer, thereby fabricating an optical medium for measurement as a whole. As shown in FIG. 2, this holographic recording medium for measurement is one in which a 500 μm-thickness recording layer 22 is formed between slide glasses as cover layers 21 and 23.

Example 10

A holographic recording medium for measurement was fabricated in the same manner as in Example 9, except that in Example 9, 5.590 g of NEW POLE GP-1000 (trifunctional polypropylene glycol having an average molecular weight of 1,000, manufactured by Sanyo Chemical Industries, Ltd.) was used in place of 4.545 g of T5650J (polycarbonate diol having an average molecular weight of 760, manufactured by Asahi Kasei Chemicals Corporation) and 0.505 g of trimethylolpropane; and that 1.410 g of hexamethylene diisocyanate was used.

Example 11

An optical medium for measurement was obtained in the same manner as in Example 10, except that 2,4-bis(2-benzothiophenyl)phenyl acrylate obtained in Synthesis Example 2 was used in place of 3-(1-thianthrenyl)phenyl acrylate obtained in Synthesis Example 1.

Example 12

An optical medium for measurement was obtained in the same manner as in Example 9, except that 2,4-bis(4-dibenzothiophenyl)phenyl acrylate obtained in Synthesis Example 6 was used in place of 3-(1-thianthrenyl)phenyl acrylate obtained in Synthesis Example 1.

Example 13

An optical medium for measurement was obtained in the same manner as in Example 10, except that 2,4-bis(4-dibenzothiophenyl)phenyl acrylate obtained in Synthesis Example 6 was used in place of 3-(1-thianthrenyl)phenyl acrylate obtained in Synthesis Example 1.

Example 14

An optical medium for measurement was obtained in the same manner as in Example 10, except that 2,6-bis(4-dibenzothiophenyl)-4-methylphenyl acrylate obtained in Synthesis Example 7 was used in place of 3-(1-thianthrenyl)phenyl acrylate obtained in Synthesis Example 1.

Example 15

An optical medium for measurement was obtained in the same manner as in Example 10, except that in Example 10, the amount of TPO (2,4,6-trimethylbenzoyldiphenylphosphine oxide, manufactured by Ciba Specialty Chemicals) was changed to 0.011 g; and that 1,6-bis(4-dibenzothiophenyl)-2-naphthyl acrylate obtained in Synthesis Example 12 was used in place of 3-(1-thianthrenyl)phenyl acrylate obtained in Synthesis Example 1.

Example 16

A solution A obtained by dissolving 0.0928 g of 1,6-bis(4-dibenzothiophenyl)-2-naphthyl acrylate obtained in Synthesis Example 12 and 0.0046 g of TPO in 0.7219 g of trimethylhexamethylene diisocyanate, followed by deaeration and a solution B obtained by mixing and dissolving 2.1641 g of PTMG1000 (diol of PTMG having an average molecular weight of 1,000), 0.1139 g of trimethylolpropane and 0.0006 g of dioctyltin dilaurate, followed by deaeration were prepared; and the both solutions were added and well stirred, followed by deaeration. The preceding deaerated liquid was cast on a slide glass in which a 500 μm-thick TEFLON (a registered trademark) sheet was placed as a spacer on both ends thereof; a slide glass was further covered thereon; the periphery was fixed by a grip; and the assembly was heated at 60° C. for 15 hours to prepare a recording layer, thereby fabricating a holographic recording medium for measurement as a whole.

Example 17

An optical medium for measurement was obtained in the same manner as in Example 15, except that 2,4-bis(4-dibenzothiophenyl)-6-bromophenyl acrylate obtained in Synthesis Example 11 was used in place of 1,6-bis(4-dibenzothiophenyl)-2-naphthyl acrylate obtained in Synthesis Example 12.

Example 18

An optical medium for measurement was obtained in the same manner as in Example 16, except that 2,4,6-tris(4-dibenzothiophenyl)phenyl acrylate obtained in Synthesis Example 9 was used in place of 1,6-bis(4-dibenzothiophenyl)-2-naphthyl acrylate obtained in Synthesis Example 12.

Example 19

An optical medium for measurement was obtained in the same manner as in Example 16, except that 2,4-bis(4-dibenzothiophenyl)-6-[4-(N-carbazole)phenyl]phenyl acrylate obtained in Synthesis Example 10 was used in place of 1,6-bis(4-dibenzothiophenyl)-2-naphthyl acrylate obtained in Synthesis Example 12.

Example 20

An optical medium for measurement was obtained in the same manner as in Example 15, except that 2,4-bis(2-dibenzothiophenyl)phenyl acrylate obtained in Synthesis Example 6 was used in place of 1,6-bis(4-dibenzothiophenyl)-2-naphthyl acrylate obtained in Synthesis Example 12.

Comparative Example 1

A holographic recording medium for measurement was fabricated in the same procedures as in Example 10, except that 0.186 g of BR30 (2,4,6-tribromophenyl acrylate, manufactured by Dai-ichi Kogyo Seiyaku Co., Ltd.) was used in place of 0.216 g 3-(1-thianthrenyl)phenyl acrylate obtained in Synthesis Example 1; and that 0.019 g of TPO (2,4,6-trimethylbenzoyldiphenylphosphine oxide, manufactured by Ciba Specialty Chemicals), 1.209 g of hexamethylene diisocyanate, 4.791 g of NEW POLE GP-1000 (trifunctional polypropylene glycol having an average molecular weight of 1,000, manufactured by Sanyo Chemical Industries, Ltd.) and 0.0012 g of dioctyltin dilaurate were used.

Constituent components of the recording layer of each of the holographic recording media manufactured by the foregoing Examples 9 to 20 and Comparative Example 1 were summarized in Table 2.

[Holographic Recording]

By using each of the holographic recording media, holographic recording was carried out in the following procedures.

By using a semiconductor laser having a wavelength of 405 nm, two-beam plane wave holographic recording was carried out using an exposure apparatus having an exposure power density of 6.0 mW/cm$^2$ per beam as shown in FIG. 1. The medium was subjected to multiplex recording of 61 times in the same place at intervals of 1° from −30° to 30°. At that time, a total sum of square roots of diffraction efficiency is defined as M/# (M number). Also, a light transmittance at the recording wavelength before and after recording was measured. Details are described below.

FIG. 1(a) is a configuration view showing an outline of an apparatus used for the holographic recording; FIG. 1(b) is a configuration view showing the surface of an LED unit; and FIG. 1(c) is a configuration view showing an arrangement of LED of the LED unit surface.

In FIG. 1, S denotes a sample of a holographic recording medium; each of M1 to M3 denotes a mirror; PBS denotes a polarizing beam splitter; L1 denotes a laser light source for recording light capable of emitting light having a wavelength of 405 nm (a Sony's single mode laser diode from which light in the vicinity of 405 nm is obtainable was used ("L1" in FIG. 1)); L2 denotes a laser light source for reproducing light capable of emitting light having a wavelength of 633 nm; and each of PD1 and PD2 denotes a photodetector. Also, 1 denotes an LED unit; 2 denotes an arm; and 3 denotes a support.

In the case of usual recording/reproduction, the LED unit is located as shown by solid lines. In the case of uniform exposure, as shown by broken lines, the support 3 is rotated; the installed arm 2 and LED of the LED unit 1 move to the front side of the recorded area of the sample S; and LED then turns on a light for a fixed period of time. As shown in FIG. 1(c), LED 1B is arranged in a state of five spots on the dice on an LED unit surface 1A. A power source is connected with each of the light sources L1 and L2, the photodetectors PD1 and PD2 and the LED unit 1.

As shown in FIG. 1, light of 405 nm was divided by the polarizing beam splitter ("PBS" in the drawing), thereby allowing two beams to intersect with each other at an angle of 50.00° on the recording surface. At that time, the light was irradiated in such a manner that a dissector of the angle formed by the two beams was vertical against the recording surface; and that an oscillation surface of the electric field spectrum of the two beams obtained by division was vertical against the plane surface including the intersecting two beams.

After the holographic recording, an He—Ne laser from which light of 633 nm is obtainable (V05-LHP151, manufactured by Melles Griot; "L2" in the drawing) was used; the light was irradiated at an angle of 30.19° against the recording surface; and the diffracted light was detected using a power meter and detectors (2930-C, 918-SL, manufactured by Newport; "PD1" and "PD2" in the drawing), thereby deciding whether or not the holographic recording was correctly performed. The diffraction efficiency of a hologram is given as a ratio to the total sum of transmitted light intensity and diffracted light intensity of the intensity of the diffracted light.

<Measurement of M/#, Rate of Shrinkage and (M/#)/(Rate of Shrinkage)>

Since M/# is a value of a standard of multiplex recording, it is preferable that M/# is not excessively large regarding the diffraction efficiency at every one-time recording, and if it is too small, the recording cannot be performed. Accordingly, when M/# obtained by regulating the diffraction efficiency at every one-time recording to about several % and performing the recording with a large multiplicity as far as possible is determined, a standard of proper multiplex recording is revealed. Though the multiplexing mode includes an angle, a shift and so forth, it may be said that since angle multiplexing is said to be simple and easy, it is a suitable mode in knowing the capability of a material. When recording is performed by moving an angle of a sample relative to an optical axis (an angle formed between a bisector of an interior angle in an intersecting point of two beams, namely incident lights from the mirrors M1 and M2 of FIG. 1 and a normal line from the sample) at intervals of 1° from −20° to 20°, multiplex recording of 41 times can be achieved, and when recording is performed at intervals of 0.5° from −30° to 30°, multiplex recording of 121 times can be achieved. The diffraction efficiency includes two expressions of a ratio of incident light to diffracted light (also called an external diffraction efficiency) and a ratio of a total sum of transmitted light and diffracted light to diffracted light (also called an internal diffraction efficiency). In the invention, the internal diffraction efficiency in which reflection of the sample surface and diffusion in the inside of the sample can be neglected, and the recording performance of a material can be examined is employed. Here, a value obtained by performing multiplex recording of 61 times at intervals of 1° from −30° to 30° and totaling square roots of the obtained diffraction efficiency over the entirety of multiplex recording was employed as M/#.

Specifically, in each of the Examples, first of all, using one of plurally prepared optical recording media, two beams, namely incident lights of 405 nm are irradiated from each of the mirrors M1 and M2 in FIG. 1 until the diffraction efficiency becomes constant in a state where an angle formed between a bisector of an interior angle in an intersecting point of the two beams and a normal line of the medium, and minimum energy which has become constant is measured (on that occasion, the diffraction efficiency is evaluated using light of 633 nm from the mirror M3).

Subsequently, with respect to another medium, multiplex recording is performed while making the previously determined minimum energy value as a standard for total irradiation energy during the multiplex recording of 61 times. On that occasion, the diffraction efficiency at every recording is kept at several % by exponentially increasing the irradiation energy in conformity with the recording number. After multiplex recording of 61 times, light (405 nm) is subsequently irradiated from the mirror M1 in FIG. 1, the diffraction efficiency is measured at an angle of from −30° to 30°, and a total sum of square roots of diffraction efficiency at each angle is defined as M/#.

Here, when the amount of the total irradiation energy is excessively small, the monomer remains, whereas when the irradiation energy is excessively large at a stage of a low recording number, the multiplex recording cannot be achieved. Therefore, in any of these cases, there may be a possibility that M/# is underestimated. For that reason, the evaluation was performed plural times while changing the sample and varying the irradiation energy condition of, for example, increase and decrease of the irradiation energy at the initial stage of recording, increase and decrease of the total irradiation energy, etc., and a condition under which the contained monomer was substantially completely consumed until recording of 61 times (M/# reached substantially an equilibrium until the recording of 61 times) while keeping the diffraction efficiency of every one-time recording at several % or more, thereby obtaining a maximum value as M/#. Then, the obtained maximum value was defined as M/# of the subject medium. Incidentally, the M/# value is separately influenced by the thickness or configuration of the sample. The thickness can be freely varied from the standpoint of experimental works. Here, the comparison is made using an actually measured value at the time when the thickness of the recording layer is 500 μm.

The rate of shrinkage is brought by the fact that the reactive compound is polymerized upon recording to increase the molecular weight, and as a result, the volume becomes small. Though it is preferable that the rate of shrinkage can be actually measured from the thickness of the recording layer or the whole of the sample, in the case where the amount of the reactive compound is small, and the recording layer is not sufficiently thick, it is difficult to perform accurate measurement. Accordingly, in view of the fact that a diffraction surface is formed by recording, volumetric shrinkage is defined with a deviation of the angle of this diffraction surface, thereby expressing it as a rate of shrinkage. The deviation of the angle of the diffraction surface is calculated from a difference between a difference in the angle between recording and reproduction of the diffracted light and a deviation of the diffracted light generated at the time when a change in the average refractive index before and after the recording layer by the chemical reaction is defined as 0.001. The shrinkage is complexly generated in not only the thickness direction but the plane vertical to the thickness. However, since the inside of the plane is restrained by the protective layers before and after the recording layer, it may be estimated that the influence against the diffraction surface is small. Incidentally, when multiplex recording is performed in the same procedures as in the case of determining M/#, the reactive compound is consumed with a high degree of conversion, and many diffraction surfaces are formed. At the same time, since the influence of shrinkage leaves step-by-step in the record, the result becomes complicated, and analysis becomes difficult depending upon what diffraction surface is to be used. Accordingly, the multiplex recording was performed 15 times; two beams, namely incident lights (wavelength: 405 nm) from the mirror M1 and M2 of FIG. 1 were irradiated for recording under a condition of an M/# consumed amount of from 1 to 3%; incoherent light including a wavelength region of 405 nm the same as the recording wavelength was then irradiated over the entire surface of an area of the sample provided for recording by the LED unit shown in FIG. 1, thereby completely consuming the remaining reactive compound; and thereafter, the angle of the recorded diffraction surface was again measured using light having a wavelength of 405 nm (incident light from the mirror M1, thereby determining the rate of shrinkage.

Specifically, recording was performed by rotating the sample relative to the optical axis and moving an angle formed between a bisector of an interior angle in an intersecting point of two beams and a normal line from the sample at intervals of 4° from −28° to 28°, thereby achieving multiplex recording of 15 times at a one-time diffraction efficiency of not more than 0.1%, and uniform exposure by the LED unit was performed at 6 mW/cm$^2$ for 5 minutes. With respect to the medium after the multiplex recording, angle selectivity of the diffraction efficiency is plotted, and each of the recorded angles is measured for a deviation from the original recorded angle position. The determined angle deviation value (=deviation of diffraction lattice space) was substituted into a relation regarding the angle deviation and the rate of shrinkage as described in *Applied Physics Letters*, Vol. 73, No. 10, pages 1337 to 1339 (1998), etc., from which was then introduced a value of rate of shrinkage satisfying the subject relation through trial and error.

On that occasion, as a value of the average refractive index before shrinkage, 1.51 which is an actually measured value of polyurethane was employed; and as a value of the average refractive index after shrinkage, 1.511 which is a value obtained by assuming a change of the average refractive index before and after recording by the chemical reaction as 0.001 and multiplying the foregoing value by 0.001 was employed.

Incidentally, it would be better that a temperature difference before and after recording is as small as possible, and preferably, the evaluation is performed under a condition that the temperature difference before and after recording is not more than 0.5° C. A temperature change of 1° C. produces a scattering of the rate of shrinkage of about ±0.05%.

The results obtained by evaluating the holographic recording media of Examples 9 to 20 and Comparative Example 1 were summarized in Table 3. All of the holographic recording media of Examples 9 to 20 attain M/# of 10 or more, a rate of shrinkage of less than 0.15% and (M/#)/(rate of shrinkage) of 100 or more. On the other hand, in the holographic recording medium of Comparative Example 1, though the rate of shrinkage is less than 0.15%, M/# is small as less than 10, and (M/#)/(rate of shrinkage) is merely 66.7.

<Light Transmittance Before Recording and Light Transmittance after Recording>

When the sample or recording layer is thick, there may be the case where light is absorbed and scattered in the inside, and the intensity of light is insufficient, so that the performance of recording is inferior. Also, the photoinitiator is chemically changed by light irradiation, so that the absorption intensity is largely changed at the wavelength of recording light; and therefore, the degree of transmission is measured before and after recording. With respect to the light transmittance, after the intensity of light was measured in a state where no sample was present, the sample was placed such that its plate surface was vertical to an optical path, and the intensity of light was again measured for a short period of time to an extend that no chemical change occurred, thereby defining a ratio therebetween as the light transmittance. In the case after recording, the measurement was performed by placing the sample vertical to the optical path and at an angle at which no diffraction occurred, in such a manner that light passed through the recorded area. The wavelength was 405 nm the same as the wavelength of recording, the intensive was 6 mW/cm$^2$, and the thickness of the recording layer was 500 μm.

The results obtained by evaluating Examples 9 to 11 and 14 to 20 and Comparative Example 1 were summarized in Table 4. All of the holographic recording media of Examples 9 to 11 and 14 to 20 and Comparative Example 1 attained a light transmittance before recording of 60% or more and a light transmittance after recording of 60% or more.

TABLE 1

|  | Example | | | | | | | |
| --- | --- | --- | --- | --- | --- | --- | --- | --- |
|  | 1 | 2 | 3 | 4 | 5 | 6 | 7 | 8 |
| Synthesis Example | 3 | 6 | 7 | 8 | 9 | 10 | 11 | 12 |
| Apparent refractive index | 1.711 | 1.738 | 1.730 | 1.664 | 1.781 | 1.719 | 1.748 | 1.766 |

TABLE 2

|  |  | Example | | | | | |
| --- | --- | --- | --- | --- | --- | --- | --- |
|  |  | Example 9 | Example 10 | Example 11 | Example 12 | Example 13 | Example 14 |
| Matrix resin | Polyisocyanate | HMDI | HMDI | HMDI | HMDI | HMDI | HMDI |
|  | Polyol 1 | T5650 | GP1000 | GP1000 | T5650 | GP1000 | GP1000 |
|  | Polyol 2 | TMP |  |  | TMP |  |  |
| Reactive compound | Synthesis Example | Synthesis Example 1 | Synthesis Example 1 | Synthesis Example 2 | Synthesis Example 6 | Synthesis Example 6 | Synthesis Example 7 |
| Photoinitiator | TPO | TPO | TPO | TPO | TPO | TPO | TPO |

|  |  | Example | | | | | | Comparative Example |
| --- | --- | --- | --- | --- | --- | --- | --- | --- |
|  |  | Example 15 | Example 16 | Example 17 | Example 18 | Example 19 | Example 20 |  |
| Matrix resin | Polyisocyanate | HMDI | TMHMDI | HMDI | TMHMDI | TMHMDI | HMDI | HMDI |
|  | Polyol 1 | GP1000 | PTMG1000 | GP1000 | PTMG1000 | PTMG1000 | GP1000 | GP1000 |
|  | Polyol 2 |  | TMP |  | TMP | TMP |  |  |
| Reactive compound | Synthesis Example | Synthesis Example 12 | Synthesis Example 12 | Synthesis Example 11 | Synthesis Example 9 | Synthesis Example 10 | Synthesis Example 6 | TBPA |
| Photoinitiator | TPO | TPO | TPO | TPO | TPO | TPO | TPO | TPO |

TABLE 3

| | Example | | | | | |
|---|---|---|---|---|---|---|
| | Example 9 | Example 10 | Example 11 | Example 12 | Example 13 | Example 14 |
| M/# | 15.5 | 18.1 | 10.3 | 13.1 | 19.9 | 15.6 |
| Rate of shrinkage | 0.13 | 0.11 | 0.02 | 0.04 | 0.03 | 0.04 |
| (M/#)/(Rate of shrinkage) | 119 | 165 | 515 | 328 | 663 | 390 |
| Evaluation decision | Good | Good | Good | Good | Good | Good |

| | Example | | | | | | Comparative Example |
|---|---|---|---|---|---|---|---|
| | Example 15 | Example 16 | Example 17 | Example 18 | Example 19 | Example 20 | |
| M/# | 23.3 | 19.1 | 16.9 | 17.3 | 20.2 | 20.7 | 8 |
| Rate of shrinkage | 0.11 | 0.13 | 0.10 | 0.10 | 0.09 | 0.13 | 0.12 |
| (M/#)/(Rate of shrinkage) | 212 | 147 | 169 | 173 | 224 | 159 | 66.7 |
| Evaluation decision | Good | Good | Good | Good | Good | Good | |

TABLE 4

| | Example | | | |
|---|---|---|---|---|
| | Example 9 | Example 10 | Example 11 | Example 14 |
| Transmittance before recording (%) | 68 | 66 | 70 | 61 |
| Transmittance after recording (%) | 88 | 63 | 88 | 77 |

| | Example | | | | | | Comparative Example |
|---|---|---|---|---|---|---|---|
| | Example 15 | Example 16 | Example 17 | Example 18 | Example 19 | Example 20 | |
| Transmittance before recording (%) | 76 | 77 | 76 | 76 | 74 | 76 | 63 |
| Transmittance after recording (%) | 70 | 68 | 89 | 83 | 82 | 81 | 89 |

While the invention has been described in detail and with reference to specific embodiments thereof, it will be apparent to one skilled in the art that various changes and modifications can be made therein without departing from the spirit and scope thereof.

Incidentally, this application is based on a Japanese patent application (Japanese Patent Application No. 2008-152095), filed Jun. 10, 2008, the entire contents of which are hereby incorporated by reference.

INDUSTRIAL APPLICABILITY

The composition for forming a holographic recording layer and the holographic recording material using the same according to the invention have excellent characteristics from the standpoints of high diffraction efficiency, high light transmittance and small rate of shrinkage and can be suitably used for applications of recording layer formation in a holographic recording medium and so forth.

Also, the novel compound which is provided by the invention can be used in an arbitrary field in industry and is applicable to various optical products. The novel compound, the photoreactive composition and the optical material and holographic recording material using the same, all of which are provided by the invention, have excellent characteristics from the standpoints of high diffraction efficiency and low rate of shrinkage and can be suitably used for lens, optical recording, photofabrication, optical relief printing and so forth. Above all, they can be especially suitably used for applications of recording layer formation in the holographic recording medium described previously and so forth.

DESCRIPTION OF REFERENCE NUMERALS AND SIGNS

1: LED unit
1A: LED unit surface
1B: LED
2: Arm
3: Support
S: Sample
M1, M2, M3: Mirror PBS: Polarizing beam splitter
L1: Laser light source for recording light
L2: Laser light source for reproducing light
PD1, PD2: Photodetector
21: Cover layer
22: Recording layer
23: Cover layer

The invention claimed is:

1. A mono(meth)acrylate compound represented by the following formula (1):

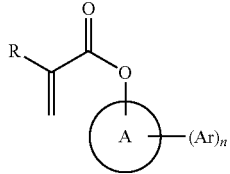

Formula (1)

wherein
A is an optionally substituted ring having a ring number of 1 or 2,
Ar is an optionally substituted (hetero)aryl group formed by condensation of two or more rings, and when Ar is an optionally substituted heteroaryl group, the number of heteroatoms is 1 or 2,
R is hydrogen or a methyl group,
n is an integer of from 2 to 7, wherein plural Ars may be the same as or different from each other, and
when A is an aromatic heterocyclic ring, and Ar is an optionally substituted (hetero)aryl group formed by condensation of two or more rings, then in the structure in which A and Ar are connected with each other, those partial structures that are in the structure of each of A and Ar, and are connected directly with each other, do not contain a heteroatom.

2. The mono(meth)acrylate compound according to claim 1, wherein Ar is an optionally substituted heteroaryl group.

3. The mono(meth)acrylate compound according to claim 1, wherein a refractive index of Ar estimated according to the Lorentz-Lorenz equation is 1.60 or more.

4. The mono(meth)acrylate compound according to claim 1, wherein a refractive index of A estimated according to the Lorentz-Lorenz equation is 1.43 or more.

5. A photoreactive composition comprising the mono(meth)acrylate compound according to claim 1.

6. The photoreactive composition according to claim 5, which further comprises a matrix resin and a photoinitiator.

7. The photoreactive composition according to claim 6, wherein the matrix resin is obtained by a reaction of an isocyanate and a polyol.

8. An optical material comprising the photoreactive composition according to claim 5.

9. A holographic recording material comprising the optical material according to claim 8.

10. A holographic recording medium comprising a layer containing the holographic recording material according to claim 9 as a recording layer.

* * * * *